(12) United States Patent
Young et al.

(10) Patent No.: US 11,965,161 B2
(45) Date of Patent: Apr. 23, 2024

(54) METHODS AND COMPOSITIONS FOR SENSITIZATION OF TUMOR CELLS TO IMMUNE THERAPY

(71) Applicant: Regeneron Pharmaceuticals, Inc., Tarrytown, NY (US)

(72) Inventors: Tara Young, Belleville, NJ (US); Christopher Daly, New York, NY (US); Gavin Thurston, Briarcliff Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/191,466

(22) Filed: Mar. 3, 2021

(65) Prior Publication Data

US 2021/0277396 A1  Sep. 9, 2021

Related U.S. Application Data

(60) Provisional application No. 62/985,004, filed on Mar. 4, 2020.

(51) Int. Cl.
| | |
|---|---|
| *C12N 15/113* | (2010.01) |
| *A61K 45/06* | (2006.01) |
| *C12N 9/22* | (2006.01) |
| *C12Q 1/68* | (2018.01) |

(52) U.S. Cl.
CPC ........... *C12N 15/113* (2013.01); *A61K 45/06* (2013.01); *C12N 9/22* (2013.01); *C12N 2310/11* (2013.01); *C12N 2310/141* (2013.01); *C12N 2310/531* (2013.01)

(58) Field of Classification Search
None
See application file for complete search history.

(56) References Cited

FOREIGN PATENT DOCUMENTS

| WO | WO-2013/021384 A1 | 2/2013 |
|---|---|---|
| WO | WO-2021/178556 A1 | 9/2021 |

OTHER PUBLICATIONS

Zhou et al., Acta Biochim Biopys Sin vol. 48(1):60-74, Dec. 5, 2015.*
Li et al., Signal Transduction and Targeted Therapy vol. 5(1), Jan. 3, 2020.*
Boya et al., "Inhibition of Macroautophagy Triggers Apoptosis," Mol Cell Bio, 25(3): 1025-1040 (2005).
Giampietri et al., "Autophagy modulators sensitize prostate epithelial cancer cell lines to TNF-alpha-dependent apoptosis," Apoptosis: An International Journal of Programmed Cell Death, 17(11): 1210-1222 (2012).
Gozuacik et al., "Autophagy as a cell death and tumor suppressor mechanism," Oncogene, 23(16): 2891-2906 (2004).
Invitation to Pay Additional Fees for International Application No. PCT/US2021/020697 dated Jun. 11, 2021.
Lawson et al., "Functional genomic landscape of cancer-intrinsic evasion of killing by T Cells," Nature, 586(7827): 120-126 (2020).
Levy et al., "Modulation of pediatric brain tumor autophagy and chemosensitivity," J Neurooncol, 106(2): 281-290 (2011).
Li et al., "Efficient Cross-presentation Depends of Autophagy in Tumor Cells," Cancer Res, 68(17): 6889-6895 (2008).
Sivaprasad et al., "Inhibition of ERK attenuates autophagy and potentiates tumour necrosis factor-[alpha]-induced cell death in MCF-7 cells," J Cell Mol Med, 12(4): 1265-1271 (2008).
Ye et al., "Negatively-regulated necroptosis by autophagy required caspase-6 activation in TNF[alpha]-treated murine fibrosarcoma L929 c," International Hnmunopharmacology, 17(3): 548-555 (2013).
Zhou et al., "Autophagy in tumorigenesis and cancer therapy: Dr. Jekyll or Mr. Hyde?" Cancer Lett, 323(2): 115-127 (2012).
International Search Report and Written Opinion for International Application No. PCT/US2021/020697 dated Aug. 4, 2021.

* cited by examiner

*Primary Examiner* — Sean McGarry
(74) *Attorney, Agent, or Firm* — Foley Hoag LLP; Brendan T. Jones; David E. Shore

(57) ABSTRACT

Provided herein are methods and compositions related to the treatment or prevention of cancer (e.g., by targeting a tumor in a subject with cancer) by administering to a subject an agent that inhibits autophagy. In certain aspects, provided herein are methods of compositions related to methods of sensitizing cancer cells to tumor necrosis factor-alpha (TNF-α) mediated killing by contacting the cells or administering the agent that inhibits autophagy.

45 Claims, 56 Drawing Sheets

Specification includes a Sequence Listing.

B.

C.

D.

E.

F.

G.

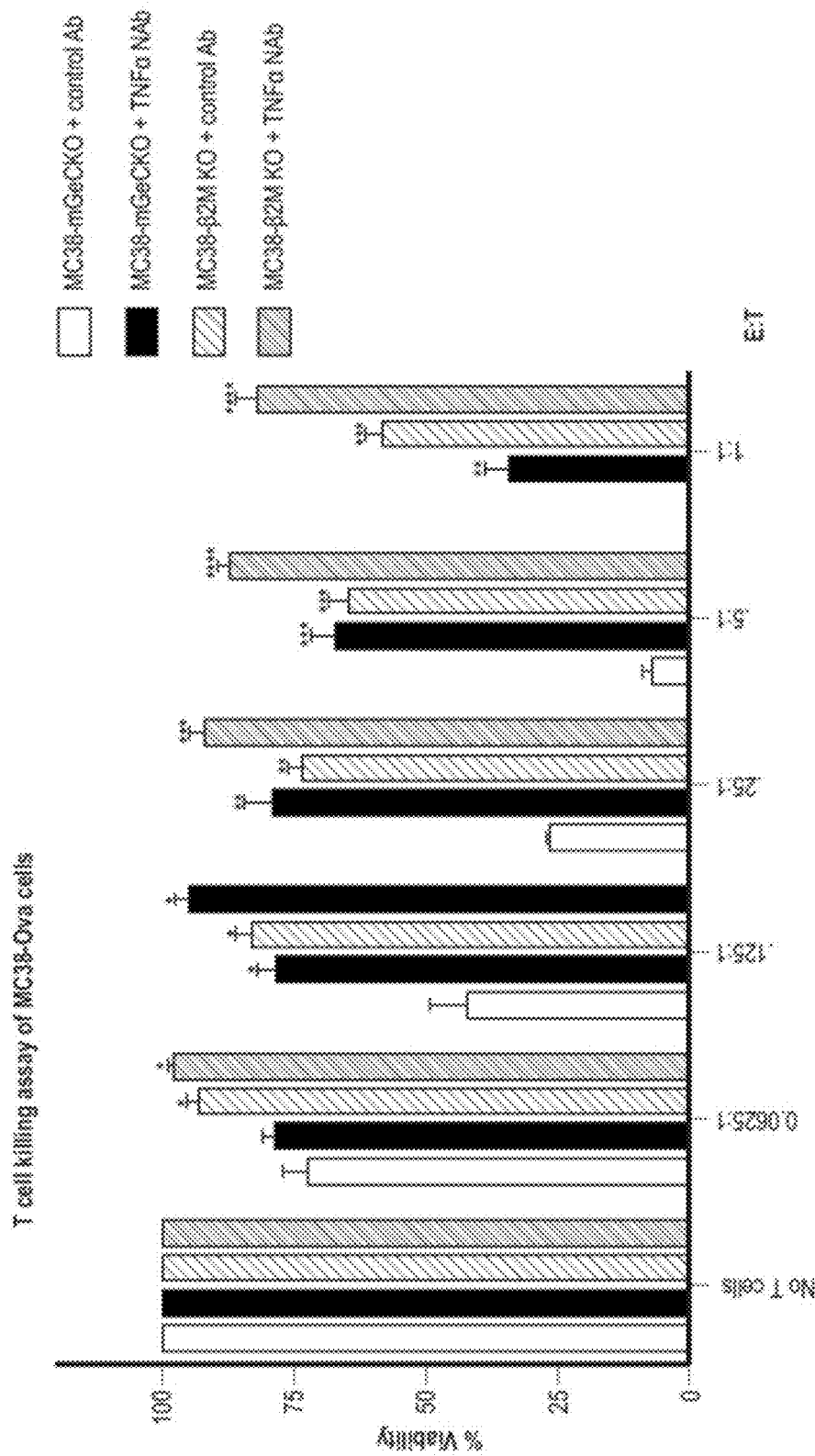

C.

E.

D.

F.

G.

A.

B.

C.

A.

B.

C.

D.

E.

F.

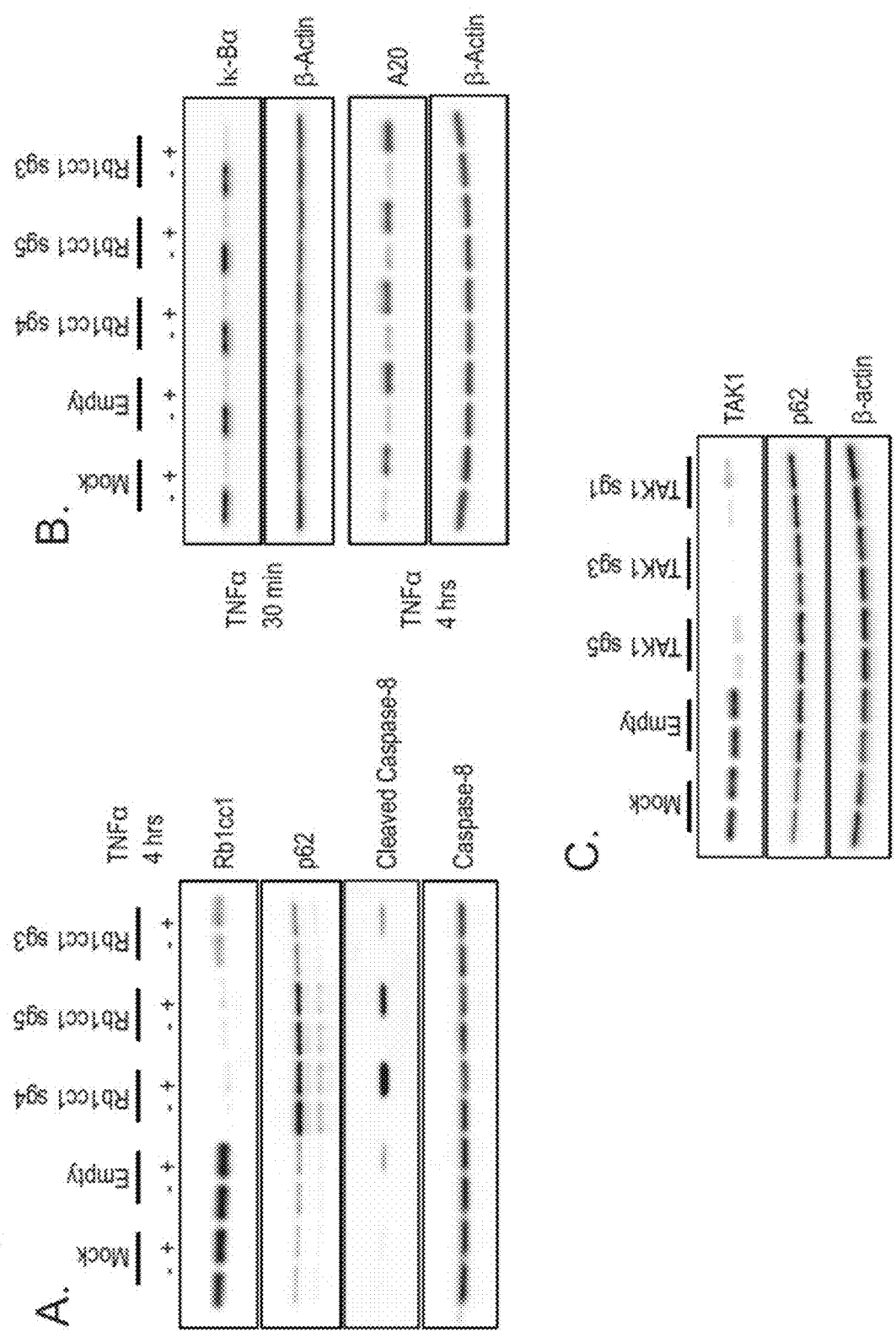

D.

E.

C.

D.

A.

B.

C.

D.

E.

F.

B. Human cell lines

_US 11,965,161 B2_

METHODS AND COMPOSITIONS FOR SENSITIZATION OF TUMOR CELLS TO IMMUNE THERAPY

CROSS-REFERENCE TO RELATED APPLICATION

This application claims the benefit of the following U.S. Provisional Application No. 62/985,004, filed Mar. 4, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Mar. 3, 2021, is named RPB-02001_SL.txt and is 14,383 bytes in size.

BACKGROUND

Cancer is the second most common cause of death in the United States. While immunotherapies have transformed the treatment of cancer, tumor cell resistance to these treatments poses a substantial challenge. For example, loss-of-function mutations in beta-2-microglobulin (B2M) or JAK1/JAK2 in tumor cells are associated with clinical resistance to checkpoint blockade. Importantly, the molecular mechanisms that control tumor cell sensitivity to T cell killing remain to be fully characterized. Thus, there remains a need to for new and effective treatments for cancer, including treatments that increase cancer cell sensitivity to T cell killing.

SUMMARY

Provided herein are methods and compositions for increasing cancer cell sensitivity to T cell killing (e.g., tumor necrosis factor-alpha (TNF-α) mediated killing) through the inhibition of autophagy and/or the NF-κB pathway. Also provided herein are methods and compositions for treating and/or preventing cancer in a subject (e.g., a subject in need thereof) by increasing the sensitivity of cancer cells in the subject to T cell killing (e.g., TNF-α mediated killing) by inhibiting autophagy and/or the NF-κB pathway in the cancer cells. In some embodiments, the methods provided herein further comprise administering a cancer therapy (e.g., a cancer immunotherapy) to the subject.

In some aspects, provided herein are methods of sensitizing cancer cells to TNF-α mediated killing by contacting the cancer cells with an agent (e.g., at least one agent disclosed herein) that inhibits autophagy and/or the NF-κB pathway in the cancer cells. In certain aspects, provided herein are methods of increasing TNF-α mediated killing of cancer cells in a subject by administering to the subject at least one agent (e.g., an agent disclosed herein) that inhibits autophagy and/or the NF-κB pathway in the cancer cells. In some embodiments, the cancer cells are in a subject. In some embodiments, the cancer cells are in a tumor (e.g., a solid tumor in a subject). In certain embodiments, the method further comprises administering a cancer therapy (e.g., a cancer immunotherapy) to the subject.

In some embodiments, the agent that inhibits autophagy by inhibiting the expression or activity of an autophagy gene (i.e., a gene that encodes a product that when inhibited results in reduced levels of autophagy in a cell). In some embodiments, the agent targets the autophagy gene (e.g., the agent modifies the sequence of the autophagy gene). In certain embodiments, the agent targets a product of the autophagy gene (e.g., an RNA or protein encoded by the autophagy gene). In some embodiments, the autophagy gene may be selected from ATG12, WIPI2, RB1CC1, PIK3C3, ATG9A, ATG2A, ATG5, ATG14, EI24, NRBF2, ATG13, TAX1BP1, and ATG10.

In some embodiments, the agent inhibits the NF-κB pathway by inhibiting the expression or activity of an NF-κB pathway gene. In some embodiments, the agent targets the NF-κB pathway gene itself (e.g., the agent modifies the sequence of the NF-κB pathway gene). In certain embodiments, the agent targets a product of the NF-κB pathway gene (e.g., an RNA or protein encoded by the NF-κB pathway gene). In certain embodiments, the NF-κB gene may be selected from CFLAR, UBE2L3, RNF31, IKBKB, MAP3K7, TAB1, RELA, IKKBKG, CHUK, TAB2, TBK1, MAPKAPK2, RBCK1, TRAF2, SHARPIN, and TNFAIP3.

Thus, in certain embodiments, the agent may modify at least one autophagy gene or NF-κB gene, wherein the modification of the at least one autophagy gene and/or NF-κB gene results in a decrease in the expression and/or activity of an autophagy gene product and/or NF-κB gene product. In certain embodiments, modification of the autophagy gene or NF-κB gene may comprise a deletion, an insertion, a replacement, or a combination thereof. In certain embodiments, the agent may be a CRISPR/Cas agent, a TALEN nuclease or a Zinc-finger nuclease.

In certain embodiments, the agent inhibits the activity and/or reduces the levels of an RNA or protein encoded by an autophagy gene or an NF-κB gene. In some embodiments, the agent may be an interfering nucleic acid e.g., an siRNA, an shRNA, a miRNA, or an antisense oligonucleotide) that targets a RNA (e.g., an mRNA) encoded by an autophagy gene or an NF-κB gene. In some embodiments, the agent is a small molecule inhibitor of autophagy or of the NF-κB pathway.

In certain embodiments, the methods provided herein further include administering an additional anti-cancer therapy to the subject. In some embodiments, the additional anti-cancer therapy is a cancer immunotherapy. In some embodiments, the cancer immunotherapy comprises administering an autologous or allogenic T cell therapy to the subject, administering an autologous or allogenic CAR T cell therapy, administering a cancer vaccine to the subject, administering TNF-α to the subject, and/or administering an immune checkpoint inhibitor to the subject. In some embodiments, the additional anti-cancer therapy comprises the administration of a Smac mimetic (e.g., LCL-161, APG-1387, TL32711, GDC-0917, HGS1029, AT-406) to the subject.

In certain aspects, provided herein are agents that inhibit autophagy in the cancer cells for use in sensitizing cancer cells in a subject to TNF-α mediated killing. Additionally, in some aspects, provided herein are agents that inhibit autophagy in the cancer cells for use in increasing TNF-α mediated killing of cancer cells in a subject. In some aspects, provided herein are combination therapies comprising an agent that inhibits autophagy in cancer cells and a cancer immunotherapy for use in treating cancer.

DETAILED DESCRIPTION

General

Figure 1A:
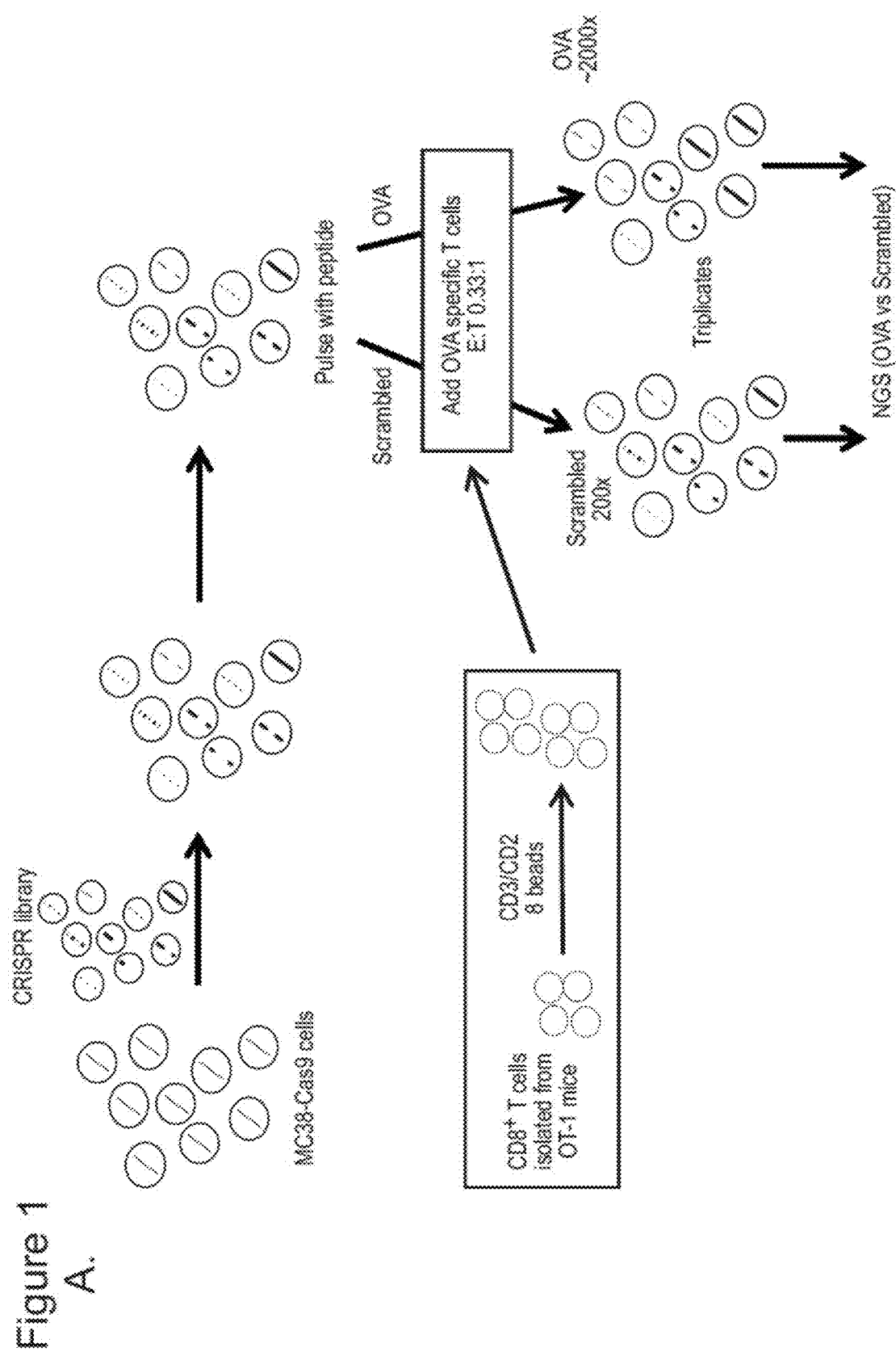
FIG. 1 has seven parts, A-G, and shows genome-wide CRISPR KO screen identifies tumor cell genes that modulate killing by cytotoxic T cells. Part A shows schematic of pooled CRISPR screen. MC38 cancer cells modified with the mouse GeCKO sgRNA library were pulsed with Ova or scrambled control peptides and then cultured with activated Ova-specific cytotoxic T cells. Following T cell killing, sgRNA representation in surviving tumor cells was assessed by Illumina sequencing. Biological triplicates were performed (Parts B, D, F). Volcano plots showing genes that either promote (enriched sgRNAs) or limit (depleted sgRNAs) tumor cell killing. Genes of interest that promote killing are highlighted in part B (e.g., antigen presentation, TNFα signaling, mTOR signaling). Genes of interest that limit killing are highlighted in part D and F (e.g., NF-κB pathway, autophagy). X-axes show the Z scores (calculated from the mean $log_2$ fold change for 6 sgRNAs targeting each gene in the Ova-pulsed cells compared to the scrambled peptide-pulsed cells). Y-axes show P-values calculated by MAGeCK (Parts C, E, G). Distrubution of $log_2$ fold change for all 129,209 sgRNAs in the library (frequency histograms). Individual sgRNAs targeting genes of interest are indicated by slashed lines in panel C and by slashed lines in part E and G.

The disclosure herein is based, in part, on the discovery that inhibition of the autophagy pathway, including inhibition of autophagy initiation, transfer of membrane material, or autophagosome expansion, sensitized cancer cells to TNFα-mediated killing (e.g., by T cells). Additionally, Applicant has shown herein that inhibition of the NF-κB pathway sensitizes cancer cells to TNF-α mediated killing. Notably, as shown herein, genetic inhibition of autophagy sensitizes tumor cells to T cell-mediated killing in vivo. Applicant shows herein that the autophagy pathway and NF-κB pathway are important modulators of immunotherapy responsiveness, and that inhibition of these pathways enhances the efficacy of cancer therapies, especially T cell-directed therapies.

Thus, in certain aspects, provided herein are methods of sensitizing cancer cells to TNF-α mediated killing by contacting the cancer cells with an agent (e.g., an agent disclosed herein) that inhibits autophagy and/or the NF-κB pathway in the cancer cells. In some aspects, provided herein are methods of sensitizing cancer cells in a subject to TNF-α mediated killing by administering to the subject an agent (e.g., an agent disclosed herein) that inhibits autophagy and/or the NF-κB pathway in the cancer cells.

In other aspects, provided herein are methods of increasing TNF-α mediated killing of cancer cells in a subject by administering to the subject at least one agent (e.g., an agent disclosed herein) that inhibits autophagy and/or the NF-κB pathway in the cancer cells.

In additional aspects, the methods described herein include methods of sensitizing a tumor in a subject to TNF-α mediated killing or increasing TNF-α mediated killing of a tumor in a subject by administering to the subject an agent (e.g., an agent disclosed herein) that inhibits autophagy and/or the NF-κB pathway in the tumor. Also provided herein are methods of treating cancer in a subject by administering to the subject an agent (e.g., an agent disclosed herein) that inhibits autophagy and/or the NF-κB pathway in cancer cells in the subject and administering to the subject a second agent that induces TNF-α mediated killing, such as a cancer immunotherapy.

DEFINITIONS

The articles "a" and "an" are used herein to refer to one or to more than one (i.e. to at least one) of the grammatical object of the article. By way of example, "an element" means one element or more than one element.

The term "agent" is used herein to denote a chemical compound, a small molecule, a mixture of chemical compounds, a biological macromolecule (such as a nucleic acid (e.g., an interfering nucleic acid), an antibody, an antibody fragment, a protein, a peptide), a mixture of biological macromolecules, and/or a combination thereof. In certain embodiments, the agent herein is a composition comprising the components of a CRISPR/Cas system. The activity of such agents may render them suitable as a "therapeutic agent" which is a biologically, physiologically, or pharmacologically active substance (or substances) that acts locally or systemically in a subject.

As used herein, an "autophagy gene" is gene that encodes a product that, when inhibited, results in reduced levels of autophagy in a cell.

As used herein, the term "cancer" includes, but is not limited to, solid tumors and blood borne tumors. The term cancer includes diseases of the skin, tissues, organs, bone, cartilage, blood and vessels. The term "cancer" further encompasses primary and metastatic cancers.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

As used herein, the phrase "conjoint administration" refers to any form of administration of two or more different therapeutic agents such that the second agent is administered while the previously administered therapeutic agent is still effective in the body (e.g., the two agents are simultaneously effective in the subject, which may include synergistic effects of the two agents).

The term "gene" refers to a DNA sequence in a chromosome that codes for a product (e.g., an RNA product and/or a polypeptide product) and includes the coding region, any non-coding introns interrupting the coding region, and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand.

The term "lipid particle" includes a lipid formulation that can be used to deliver a therapeutic nucleic acid (e.g., gRNA) to a target site of interest (e.g., cell, tissue, organ, and the like).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates), polyamide oligomers (e.g., *ATTA*-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain embodiments, non-ester containing linker moieties, such as amides or carbamates, are used.

As used herein, an "NF-κB gene" is a gene that encodes a product that, when inhibited, results in reduced levels of NF-κB signaling in a cell.

As used herein, a "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a non-natural arrangement.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The terms "prevent," "preventing," "prevention," and the like refer to reducing the probability of developing a disease, disorder, or condition in a subject, who does not have, but is at risk of or susceptible to developing a disease, disorder, or condition.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) Science 282:63), and natural product extract libraries.

A "small hairpin RNA" or "short hairpin RNA" or "shRNA" includes a short RNA sequence that makes a tight hairpin turn that can be used to silence gene expression via RNA interference. The shRNAs provided herein may be chemically synthesized or transcribed from a transcriptional cassette in a DNA plasmid. The shRNA hairpin structure is cleaved by the cellular machinery into siRNA, which is then bound to the RNA-induced silencing complex (RISC).

As used herein, the term "subject" means a human or non-human animal selected for treatment or therapy. In certain embodiments provided herein the subject is a human subject. In some embodiments provided herein, the subject is a subject in need of a method provided herein, such as a subject who has cancer.

The term "target sequence for a nuclease agent" includes a DNA sequence at which a nick or double-strand break is induced by a nuclease agent. Likewise, the term "target sequence for a DNA-binding protein" includes a DNA sequence to which a DNA-binding protein will bind. The target sequence can be endogenous (or native) to the cell or the target sequence can be exogenous to the cell.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

Autophagy and NF-κB Pathways

As discussed above, the disclosure herein is based, in part, on the discovery that inhibition of the autophagy pathway, including inhibition of autophagy initiation, transfer of membrane material, or autophagosome expansion sensitized cancer cells to TNFα-mediated killing (e.g., by T cells). Applicant shows herein that the autophagy pathway and NF-κB pathway are important modulators of immunotherapy responsiveness, and that inhibition of these pathways enhances the efficacy of cancer therapies, especially T cell-directed therapies.

Therefore, provided herein are methods of sensitizing cancer cells to TNF-α mediated killing by administering to the subject or contacting the cancer cells an agent (e.g., at least one agent disclosed herein) that inhibits autophagy and/or the NF-κB pathway in the cancer cells. In some embodiments, the agent inhibits the expression or activity of an autophagy gene and/or the NF-κB gene. As used herein, and autophagy gene includes, but not limited to, a gene that encodes a product that when inhibited results in reduced levels of autophagy in a cell. The autophagy gene may be, for example, ATG12, WIPI2, RB1CC1, PIK3C3, ATG9A, ATG2A, ATG5, ATG14, EI24, NRBF2, ATG13, TAX1BP1, and ATG10. Exemplary NCBI sequence references to the mRNA, protein and genomic (GRCh38.p13 primary assembly) sequences of these exemplary autophagy genes are provided in Table 1.

RELA, IKKBKG, CHUK, TAB2, TBK1, MAPKAPK2, RBCK1, TRAF2, SHARPIN, or TNFAIP3. Exemplary NCBI sequence references to the mRNA, protein and genomic (GRCh38.p13 primary assembly) sequences of these exemplary NF-κB genes are provided in Table 1.

TABLE 1

Exemplary Gene Targets of the Autophagy Pathway

| Autophagy Gene | mRNA | Protein | Genomic |
|---|---|---|---|
| ATG12 | NM_001277783.2<br>NM_004707.4 | NP_001264712.1<br>NP_004698.3 | NC_000005.10 Range: 115828200 . . . 115841565 complement |
| RB1CC1 | NM_001083617.1<br>NM_014781.5 | NP_001077086.1<br>NP_055596.3 | NC_000008.11 Range: 52622458 . . . 52714466 complement |
| ATG9A | NM_001077198.3<br>NM_024085.5 | NP_001070666.1<br>NP_076990.4 | NC_000002.12 Range: 219219380 . . . 219229636 complement |
| ATG5 | NM_001286106.1<br>NM_001286107.1<br>NM_001286108.1<br>NM_001286111.1<br>NM_004849.4 | NP_001273035.1<br>NP_001273036.1<br>NP_001273037.1<br>NP_001273040.1<br>NP_004840.1 | NC_000006.12 Range: 106184476 . . . 106325820 complement |
| EI24 | NM_001290135.2<br>NM_001330419.2<br>NM_004879.5 | NP_001277064.1<br>NP_001317348.1<br>NP_004870.3 | NC_000011.10 Range: 125569216 . . . 125584684 |
| ATG13 | NM_001142673.2<br>NM_001205119.1<br>NM_001205121.1<br>NM_001205122.1<br>NM_001346317.1<br>NM_001346333.1<br>NM_001346338.1<br>NM_001346356.1<br>NM_001346357.1<br>NM_001346360.1 | NP_001136145.1<br>NP_001192048.1<br>NP_001192050.1<br>NP_001192051.1<br>NP_001333246.1<br>NP_001333262.1<br>NP_001333267.1<br>NP_001333285.1<br>NP_001333286.1<br>NP_001333289.1 | NC_000011.10 Range: 46617276 . . . 46676019 |
| TAX1BP1 | NM_001079864.2<br>NM_001206901.1<br>NM_001206902.1<br>NM_001362794.1<br>NM_001362795.1<br>NM_006024.6 | NP_001073333.1<br>NP_001193830.1<br>NP_001193831.1<br>NP_001349723.1<br>NP_001349724.1<br>NP_006015.4 | NC_000007.14 Range: 27739373 . . . 27829767 |
| ATG10 | NM_001131028.2<br>NM_031482.5 | NP_001124500.1<br>NP_113670.1 | NC_000005.10 Range: 81972021 . . . 82258502 |
| WIPI2 | NM_001033518.2<br>NM_001033519.2<br>NM_001033520.1<br>NM_001278299.2<br>NM_015610.4<br>NM_016003.4 | NP_001028690.1<br>NP_001028691.1<br>NP_001028692.1<br>NP_001265228.1<br>NP_056425.1<br>NP_057087.2 | NC_000007.14 Range: 5190233 . . . 5233855 |
| PIK3C3 | NM_001308020.2<br>NM_002647.4 | NP_001294949.1<br>NP_002638.2 | NC_000018.10 Range: 41955226 . . . 42087830 |
| ATG2A | NM_001367971.1<br>NM_001367972.1<br>NM_015104.3 | NP_001354900.1<br>NP_001354901.1<br>NP_055919.2 | NC_000011.10 Range: 64894546 . . . 64917241 complement |
| ATG14 | NM_014924.5 | NP_055739.2 | NC_000014.9 Range: 55366391 . . . 55411830 complement |
| NRBF2 | NM_001282405.1<br>NM_030759.5 | NP_001269334.1<br>NP_110386.2 | NC_000010.11 Range: 63133247 . . . 63155031 |

In some embodiments, the agent inhibits the expression or activity of an NF-κB gene. As used herein, and NF-κB gene includes, but not limited to, a gene that encodes a product that when inhibited results in reduced levels of NF-κB signaling in a cell. The NF-κB gene may be, for example, CFLAR, UBE2L3, RNF31, IKBKB, MAP3K7, TAB1,

TABLE 2

Exemplary Genes within the NF-κB pathway

| NF-κB gene | mRNA | Protein | Genomic |
|---|---|---|---|
| CFLAR | NM_001127183.4<br>NM_001127184.3<br>NM_001202515.1<br>NM_001202516.3<br>NM_001202517.3<br>NM_001202518.2<br>NM_001308042.3<br>NM_001308043.2 | NP_001120655.1<br>NP_001120656.1<br>NP_001189444.1<br>NP_001189445.1<br>NP_001189446.1<br>NP_001189447.1<br>NP_001294971.1<br>NP_001294972.1 | NC_000002.12 Range: 201116104 . . . 201176687 |
| RNF31 | NM_001310332.1<br>NM_017999.5 | NP_001297261.1<br>NP_060469.4 | NC_000014.9 Range: 24146875 . . . 24160661 |
| MAP3K7 | NM_003188.4<br>NM_145331.3<br>NM_145332.3<br>NM_145333.3 | NP_003179.1<br>NP_663304.1<br>NP_663305.1<br>NP_663306.1 | NC_000006.12 Range: 90513579 . . . 90587072 complement |
| RELA | NM_001145138.2<br>NM_001243984.2<br>NM_001243985.1<br>NM_021975.4 | NP_001138610.1<br>NP_001230913.1<br>NP_001230914.1<br>NP_068810.3 | NC_000011.10 Range: 65653596 . . . 65662972 complement |
| CHUK | NM_001278.5<br>NM_001320928.1 | NP_001269.3<br>NP_001307857.1 | NC_000010.11 Range: 100188298 . . . 100229610 complement |
| TBK1 | NM_013254.4 | NP_037386.1 | NC_000012.12 Range: 64452105 . . . 64502114 |
| RBCK1 | NM_001323956.1<br>NM_001323958.2<br>NM_001323960.1<br>NM_006462.6<br>NM_031229.4 | NP_001310885.1<br>NP_001310887.1<br>NP_001310889.1<br>NP_006453.1<br>NP_112506.2 | NC_000020.11 Range: 408050 . . . 432139 |
| SHARPIN | NM_030974.4 | NP_112236.3 | NC_000008.11 Range: 144098637 . . . 144104248 complement |
| UBE2L3 | NM_001256355.1<br>NM_001256356.1<br>NM_003347.4 | NP_001243284.1<br>NP_001243285.1<br>NP_003338.1 | NC_000022.11 Range: 21549447 . . . 21624034 |
| IKBKB | NM_001190720.2<br>NM_001242778.2<br>NM_001556.3 | NP_001177649.1<br>NP_001229707.1<br>NP_001547.1 | NC_000008.11 Range: 42270727 . . . 42332653 |
| TAB1 | NM_006116.3<br>NM_153497.3 | NP_006107.1<br>NP_705717.1 | NC_000022.11 Range: 39399780 . . . 39437132 |
| IKBKG | NM_001099856.5<br>NM_001099857.3<br>NM_001145255.3<br>NM_001321396.2<br>NM_001321397.2<br>NM_003639.4 | NP_001093326.2<br>NP_001093327.1<br>NP_001138727.1<br>NP_001308325.1<br>NP_001308326.1<br>NP_003630.1 | NC_000023.11 Range: 154542212 . . . 154565046 |
| TAB2 | NM_001292034.3<br>NM_001292035.3<br>NM_001369506.1<br>NM_015093.5 | NP_001278963.1<br>NP_001278964.1<br>NP_001356435.1<br>NP_055908.1 | NC_000006.12 Range: 149217924 . . . 149411613 |
| MAPKAPK2 | NM_004759.5<br>NM_032960.4 | NP_004750.1<br>NP_116584.2 | NC_000001.11 Range: 206684905 . . . 206734283 |

TABLE 2-continued

Exemplary Genes within the NF-κB pathway

| NF-κB gene | mRNA | Protein | Genomic |
|---|---|---|---|
| TRAF2 | NM_021138.4 | NP_066961.2 | NC_000009.12 Range: 136881933 . . . 136926615 |
| TNFAIP3 | NM_001270507.2 | NP_001257436.1 | NC_000006.12 Range: 137866317 . . . 137883312 |
|  | NM_001270508.2 | NP_001257437.1 |  |
|  | NM_006290.4 | NP_006281.1 |  |

In other aspects, provided herein are methods of increasing TNF-α mediated killing of cancer cells in a subject by administering to the subject at least one agent that inhibits autophagy and/or the NF-κB pathway in the cancer cells (e.g., at least one agent disclosed herein, such as an agent that modifies at least one autophagy gene or at least one NF-κB gene, such as a gene in Table 1 or 2). Also disclosed herein are methods of sensitizing a tumor in a subject to TNF-α mediated killing or increasing TNF-α mediated killing of a tumor in a subject by administering to the subject an agent that inhibits autophagy and/or the NF-κB pathway in the tumor (e.g., at least one agent disclosed herein, such as an agent that modifies at least one autophagy gene or at least one NF-κB gene, such as a gene in Table 1 or 2). Also provided herein are methods of treating cancer in a subject by administering to the subject an agent that inhibits autophagy and/or the NF-κB pathway (e.g., at least one agent disclosed herein, such as an agent that modifies at least one autophagy gene or at least one NF-κB gene, such as a gene in Table 1 or 2) in cancer cells in the subject and a cancer therapy (e.g., a cancer immunotherapy). In some embodiments, modifying the at least one autophagy or NF-κB gene results in a decrease in the expression and/or activity of the gene. In some embodiments, modifying the at least one autophagy or NF-κB gene results in the elimination of the expression and/or activity of the gene.

Modulators of Autophagy and NF-κB Pathways
CRISPR/Cas Systems

In some embodiments, provided herein are agents that inhibit the expression or activity of an autophagy gene (e.g., an autophagy gene of Table 1) or an NF-κB gene (e.g., an NF-κB gene of Table 2), and methods of use thereof. In certain embodiments, the agent may be an agent that modifies at least one autophagy gene or an NF-κB gene (e.g., wherein modifying the at least one gene results in a decrease and/or elimination in the expression or activity of the gene). In some embodiments, the modification of the gene comprises a deletion, an insertion, a replacement, or a combination thereof. In some embodiments, the modification process comprises the binding of a Cas protein to the gene.

In certain embodiments, the agent that inhibits the expression or activity of an autophagy gene (e.g., an autophagy gene listed in Table 1) or an NF-κB gene (e.g., an NF-κB gene listed in Table 2) is a composition comprising a guide RNA. In some embodiments, the agent is a composition comprising a nucleic acid that comprises a first nucleotide sequence that encodes a guide RNA. The guide RNA may be effective to direct a Cas enzyme to cleave or bind a sequence in the gene, wherein the guide RNA comprises a DNA-targeting segment that targets a guide RNA target sequence within the gene. In some embodiments, the guide RNA is configured to provide a cleavage event selected from a double strand break and a single strand break within the gene. In some embodiments, the guide RNA target sequence includes or is proximate to the start codon of the gene. The guide RNA target sequence may be within about 1000, 500, 400, 300, 200, 100, 50, 45, 40, 35, 30, 25, 20, 15, 10, or 5 nucleotides of the start codon. In some embodiments, the gRNA target sequence is present in exon 1 of the targeted gene. In some embodiments, the gRNA target sequence is present in exon 2 of the targeted gene. In some embodiments, the agent that inhibits expression or activity of an autophagy gene is a composition that comprises a plurality of guide RNAs. For example, in some embodiments the composition comprises a first guide RNA targeting the 5' end of the targeted gene and a second guide RNA targeting the 3' end of the targeted gene (e.g., to induce collapse). In some embodiments the composition comprises dual gRNAs that are designed to modify or delete a functional domain of the targeted gene.

In certain embodiments, the guide RNA comprises at least 15 contiguous nucleotides that hybridize to an autophagy gene (e.g., an autophagy gene listed in Table 1) or an NF-κB gene (e.g., an NF-κB gene listed in Table 2). As one example, the at least 15 contiguous nucleotides can hybridize to a segment of an autophagy gene listed in Table 1 or an NF-κB gene listed in Table 2 that is at least 90%, at least 95%, at least 96%, at least 97%, at least 98%, or at least 99% identical to a gene sequence provided in Table 1 or Table 2, respectively. Optionally, guide RNA comprises a sequence that can hybridize to at least 15 contiguous nucleotides of a gene sequence provided in Table 1 or Table 2.

For example, in certain embodiments a targeted genetic modifications to an autophagy gene (e.g., an autophagy gene listed in Table 1) or an NF-κB gene (e.g., an NF-κB gene listed in Table 2) in a genome of a cell can be generated by contacting a cell or the genome of a cell with a Cas protein and one or more guide RNAs that hybridize to one or more guide RNA recognition sequences within a target genomic locus in the autophagy gene (e.g., an autophagy gene listed in Table 1) or the NF-κB gene (e.g., an NF-κB gene listed in Table 2). That is, targeted genetic modifications to an autophagy gene (e.g., an autophagy gene listed in Table 1) or an NF-κB gene (e.g., an NF-κB gene listed in Table 2) in a genome of a cell can be generated by contacting the cell or the genome of a cell with a Cas protein and one or more guide RNAs that target one or more guide RNA target sequences within a target genomic locus in the autophagy gene (e.g., an autophagy gene listed in Table 1) or the NF-κB gene (e.g., an NF-κB gene listed in Table 2). For example, such methods can comprise contacting a cell with a Cas protein and a guide RNA that target a guide RNA target sequence within the autophagy gene (e.g., an autophagy gene listed in Table 1) or NF-κB gene (e.g., an NF-κB gene listed in Table 2). For example, the guide RNA target sequence can include or be proximate to the start codon of an autophagy gene (e.g., an autophagy gene listed in Table 1) or an NF-κB gene (e.g., an NF-κB gene listed in Table 2) or the stop codon of an autophagy gene (e.g., an autophagy gene listed in Table 1) or an NF-κB gene (e.g., an NF-κB gene listed in Table 2). For example, the guide RNA target sequence can be within about 10, 20, 30, 40, 50, 100, 200, 300, 400, 500, or 1,000 nucleotides of the start codon or the stop codon. In some embodiments, the gRNA target sequence is in exon 1 of the targeted gene. In some embodiments, the gRNA target sequence is present in exon 2 of the targeted gene. In some embodiments, the agent that inhibits expression or activity of an autophagy gene is a composition that comprises a plurality of guide RNAs. For example, in some embodiments the composition comprises a first guide RNA targeting the 5' end of the targeted gene and a second guide RNA targeting the 3' end of the targeted gene (e.g., to induce collapse). In some embodiments the composition comprises dual gRNAs that are designed to modify or delete a functional domain of the targeted gene.

In some methods, two or more nuclease agents can be used. For example, two or more nuclease agents can be used, each targeting a nuclease target sequence including or proximate to the start codon. As another example, two nuclease agents can be used, one targeting a nuclease target sequence including or proximate to the start codon, and one targeting a nuclease target sequence including or proximate to the stop codon, wherein cleavage by the nuclease agents can result in deletion of the coding region between the two nuclease target sequences. As yet another example, three or more nuclease agents can be used, with one or more (e.g., two) targeting nuclease target sequences including or proximate to the start codon, and one or more (e.g., two) targeting nuclease target sequences including or proximate to the stop codon, wherein cleavage by the nuclease agents can result in deletion of the coding region between the nuclease target sequences including or proximate to the start codon and the nuclease target sequence including or proximate to the stop codon.

Exemplary sgRNA sequences (gene name, sgRNA ID, sgRNA number when applicable and sequence) useful for targeting exemplary autophagy genes include, but are not limited to:

```
Rb1cc1, MGLibA_44688, 1,
                                            (SEQ ID NO: 38)
AGAGTGTGTACTTACAGCGC;

Rb1cc1, MGLibA_44689, 2,
                                            (SEQ ID NO: 39)
CTGAACGTGGCAAAGAACTT;

Rb1cc1, MGLibA_44690, 3,
                                            (SEQ ID NO: 40)
TCAAGATAGACCCAATGATG;

Rb1cc1, MGLibB_44675, 4,
                                            (SEQ ID NO: 41)
CTCCATTGACCACCAGAACC;

Rb1cc1, MGLibB_44676, 5,
                                            (SEQ ID NO: 42)
ATTTGAACAGTCCTCCAGAT;

Rb1cc1, MGLibB_44677, 6,
                                            (SEQ ID NO: 43)
CTTTAGGAATAGCAGGTGCA;

Atg9a, MGLibA_05661, 1,
                                            (SEQ ID NO: 44)
CATAGTCCACACAGCTAACC;

Atg9a, MGLibA_05662, 2,
                                            (SEQ ID NO: 45)
TTGGGATCCGAAGAGCATGT;

Atg9a, MGLibA05663, 3,
                                            (SEQ ID NO: 46)
CTGCCCAAGTCTGTAGTGCC;

Atg9a, MGLibB_05661, 4,
                                            (SEQ ID NO: 47)
TCTATAACATTTGCTGCTAT;

Atg9a, MGLibB_05662, 5,
                                            (SEQ ID NO: 48)
TACATGTGAAGCCATTCTTC;

Atg9a, MGLibB_05663, 6,
                                            (SEQ ID NO: 49)
AGGATATTCGAGAGAAGAAG;

Atg12, MGLibA_05619, 1,
                                            (SEQ ID NO: 50)
TGCAGTTTCGCCCGGAACGG;

Atg12, MGLibA_05620, 2,
                                            (SEQ ID NO: 51)
CTCTGGAAGGCTCTCGCCGC;

Atg12, MGLibA_05621, 3,
                                            (SEQ ID NO: 52)
GAGCGAACCCGGACCATCCA;

Atg12, MGLibB_05619, 4,
                                            (SEQ ID NO: 53)
TCATCATACCAACTGTTCCG;

Atg12, MGLibB_05620, 5,
                                            (SEQ ID NO: 54)
CCTGCATTACTGCAAATCCC;
and Atg12, MGLibB_05621, 6,
                                            (SEQ ID NO: 55)
TTCTGGCTCATCCCCATGCC.
```

Exemplary sgRNA sequences (gene name, sgRNA ID, sgRNA number when applicable and sequence) useful for targeting exemplary NF-κB genes include, but are not limited to:

```
Map3k7, MGLibA_30286, 1,
                                            (SEQ ID NO: 16)
GATGATCGAAGCGCCGTCGC;

Map3k7, MGLibA_30287, 2,
                                            (SEQ ID NO: 17)
CGGCGCTTCGATCATCTCAC;

Map3k7, MGLibA_30288, 3,
                                            (SEQ ID NO: 18)
GGGACTTACTGGATTCAGGC;

Map3k7, MGLibB_30277, 4,
                                            (SEQ ID NO: 19)
GAGTAGTTTGCAAAGCTAAG;

Map3k7, MGLibB_30278, 5,
                                            (SEQ ID NO: 20)
TTAACTCAGGTTGTCGGAAG;

Map3k7, MGLibB_30279, 6,
                                            (SEQ ID NO: 21)
GAGGGGGGCTCATTGTATAA;

Rbck1, MGLibA_44718, 1,
                                            (SEQ ID NO: 22)
AGTACGCCCGGATATGACAG;

Rbck1, MGLibA_44719, 2,
                                            (SEQ ID NO: 23)
ACGTGTTGCGGGCTGACAGC;

Rbck1, MGLibA_44720, 3,
                                            (SEQ ID NO: 24)
CAGCTTACCGGTGGTGACTC;

Rbck1, MGLibB_44705, 4,
                                            (SEQ ID NO: 25)
AACCTGTCCTTCCGAAGCCC;

Rbck1, MGLibB_44706, 5,
                                            (SEQ ID NO: 26)
CGGGCGTACTGTGAGCCAAA;
```

```
Rbck1, MGLibB_44707, 6,
                                  (SEQ ID NO: 27)
CTGCTATCAAGTATGCCACC;

Rela, MGLibA_45072, 1,
                                  (SEQ ID NO: 28)
GCGATTCCGCTATAAATGCG;

Rela, MGLibA_45073, 2,
                                  (SEQ ID NO: 29)
TCATCGAACAGCCGAAGCAA;

Rela, MGLibA_45074, 3,
                                  (SEQ ID NO: 30)
GCCCAGACCGCAGTATCCAT;

Rela, MGLibB_45059, 4,
                                  (SEQ ID NO: 31)
CTGCCGGGATGGCTACTATG;

Rela, MGLibB_45060, 5,
                                  (SEQ ID NO: 32)
ACCGTGAAAGGGGTTATTGT;
and Rela, MGLibB_45061, 6,
                                  (SEQ ID NO: 33)
ACTTACCTGAGGGAAAGATG.
```

In some embodiments, the guide RNA may comprise a Clustered Regularly Interspaced Short Palindromic Repeats (CRISPR) RNA (crRNA) comprising the DNA-targeting segment and a trans-activating CRISPR RNA (tracrRNA). The guide RNA may be a modular guide RNA in which the crRNA and the tracrRNA are separate molecules that hybridize to each other.

In some embodiments, the composition further comprises a Cas protein or a nucleic acid sequence encoding a Cas protein (e.g., a nuclease-active Cas protein or a nuclease-inactive Cas protein fused to a transcriptional repressor domain). The Cas protein may be a Cas9 protein. The Cas9 molecule may be a S. aureus Cas9 protein, an S. pyogenes Cas9 protein, or a N. meningitidis Cas9 protein.

In certain embodiments, the methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). The methods and compositions disclosed herein can employ CRISPR/Cas systems by utilizing CRISPR complexes (comprising a guide RNA (gRNA) complexed with a Cas protein) for site-directed binding or cleavage of nucleic acids. In some embodiments, CRISPR/Cas systems used in the compositions and methods disclosed herein can be non-naturally occurring.

A. Cas Proteins

In some embodiments, Cas proteins generally comprise at least one RNA recognition or binding domain that can interact with guide RNAs. Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicellulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni.* Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Commun.* 8:14500, herein incorporated by reference in its entirety for all purposes. SaCas9 is smaller than SpCas9, and CjCas9 is smaller than both SaCas9 and SpCas9.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida*, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum*, *Eubacterium eligens*, *Moraxella bovoculi* 237, *Leptospira inadai*, Lachnospiraceae bacterium ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) Science 351(6268):84-88, herein incorporated by reference in its entirety for all purposes. Other SpCas9 variants include K855A and K810A/K1003A/R1060A.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of or a property of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337(6096): 816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Res.* 39(21):9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of *Staphylococcus aureus* Cas9 proteins are also known. For example, the *Staphyloccocus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), Lachnospiraceae bacterium ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. Examples of transcriptional activation domains include a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. Other examples include activation domains from Oct1, Oct-2A, SP1, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, TRAB1PC4, and HSF1. See, e.g., US 2016/0237456, EP3045537, and WO 2011/146121, each of which is incorporated by reference in its entirety for all purposes. In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) *Nature* 517(7536):583-588, herein incorporated by reference in its entirety for all purposes. Examples of transcriptional repressor domains include inducible cAMP early repressor (ICER) domains, Kruppel-associated box A (KRAB-A) repressor domains, YY1 glycine rich repressor domains, Sp1-like repressors, E(sp1) repressors, IκB repressor, and MeCP2. Other examples include transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., EP3045537 and WO 2011/146121, each of which is incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282(8):5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10):1328-1332; Goodman et al. (2009) *Chembiochem.* 10(9):1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the Cas protein. In one example, the labeled nucleic acid is tethered to the C-terminus or the N-terminus of the Cas protein. Likewise, the Cas protein can be tethered to the 5' end, the 3' end, or to an internal region within the labeled nucleic acid. That is, the labeled nucleic acid can be tethered in any orientation and polarity. For example, the Cas protein can be tethered to the 5' end or the 3' end of the labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methylpseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of a cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding a gRNA. Alternatively, it can be in a vector or plasmid that is separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

B. Guide RNAs

A guide RNA is an RNA molecule that binds to a Cas protein (e.g., Cas9 protein) and targets the Cas protein to a specific location within a target DNA. An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUA-GAGCUAUGCU (SEQ ID NO: 1). Any of the DNA-targeting segments disclosed herein can be joined to the 5' end of SEQ ID NO: 2 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. Examples of tracrRNA sequences comprise, consist essentially of, or consist of any one of

```
                                            (SEQ ID NO: 3)
AGCAUAGCAAGUUAAAAUAAGGCUAGUCCGUUAUCAACUUGAAAAAGUGG

CACCGAGUCGGUGCUUU,
                                            (SEQ ID NO: 4)
AAACAGCAUAGCAAGUUAAAAUAAGGCUAGUCCGUUAUCAACUUGAAAAA

GUGGCACCGAGUCGGUGCUUUU,
or
                                            (SEQ ID NO: 5)
GUUGGAACCAUUCAAAACAGCAUAGCAAGUUAAAAUAAGGCUAGUCCGUU

AUCAACUUGAAAAAGUGGCACCGAGUCGGUGC.
```

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339(6121):823-826; Jinek et al. (2012) *Science* 337(6096): 816-821; Hwang et al. (2013) *Nat. Biotechnol.* 31(3):227-229; Jiang et al. (2013) *Nat. Biotechnol.* 31(3):233-239; and Cong et al. (2013) *Science* 339(6121):819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471(7340):602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of:

```
                              (version 1; SEQ ID NO: 6)
GUUUUAGAGCUAGAAAUAGCAAGUUAAAAUAAGGCUAGUCCGUUAUCAAC

UUGAAAAAGUGGCACCGAGUCGGUGCU;

(version 2; SEQ ID NO: 7)
GUUGGAACCAUUCAAAACAGCAUAGCAAGUUAAAAUAAGGCUAGUCCGUU

AUCAACUUGAAAAAGUGGCACCGAGUCGGUGC;

(version 3; SEQ ID NO: 8)
GUUUUAGAGCUAGAAAUAGCAAGUUAAAAUAAGGCUAGUCCGUUAUCAAC

UUGAAAAAGUGGCACCGAGUCGGUGC;
and (version 4; SEQ ID NO: 9)
GUUUAAGAGCUAUGCUGGAAACAGCAUAGCAAGUUUAAAUAAGGCUAGUC

CGUUAUCAACUUGAAAAAGUGGCACCGAGUCGGUGC;
```

-continued (version 5; SEQ ID NO: 10)
GUUUUAGAGCUAGAAAUAGCAAGUUAAAAUAAGGCUAGUCCGUUAUCAAC

UUGAAAAAGUGGCACCGAGUCGGUGCUUUUUUU;

(version 6; SEQ ID NO: 11)
GUUUUAGAGCUAGAAAUAGCAAGUUAAAAUAAGGCUAGUCCGUUAUCAAC

UUGAAAAAGUGGCACCGAGUCGGUGCUUUU;
or (version 7; SEQ ID NO: 12)
GUUUAAGAGCUAUGCUGGAAACAGCAUAGCAAGUUUAAAUAAGGCUAGUC

CGUUAUCAACUUGAAAAAGUGGCACCGAGUCGGUGCUUUUUU

Guide RNAs targeting any of the guide RNA target sequences disclosed herein can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of the above scaffold sequences to form a single guide RNA (chimeric guide RNA).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) Nature 517(7536):583-588, herein incorporated by reference in its entirety for all purposes.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) Cell Rep. 22(9):2227-2235, each of which is herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-cogly-colic-acid) (PLGA) micro spheres, liposomes, micelles, inverse micelles, lipid cochleates, and lipid microtubules. Such compositions can further comprise a Cas protein, such as a Cas9 protein, or a nucleic acid encoding a Cas protein.

C. Guide RNA Target Sequences

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

The target sequence (e.g., guide RNA target sequence) for the DNA-binding protein can be anywhere within an autophagy gene (e.g., an autophagy gene listed in Table 1) or an NF-κB gene (e.g., an NF-κB gene listed in Table 2) that is suitable for altering expression of the targeted gene. As one example, the target sequence can be within a regulatory element, such as an enhancer or promoter, or can be in proximity to a regulatory element. For example, the target sequence can include or be proximate to the start codon of an autophagy gene (e.g., an autophagy gene listed in Table 1) or an NF-κB gene (e.g., an NF-κB gene listed in Table 2). For example, the target sequence can be within about 10, 20, 30, 40, 50, 100, 200, 300, 400, 500, or 1,000 nucleotides of the start codon.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CC$N_2$-3', where $N_2$ is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can be A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are $GN_{19}NGG$ (SEQ ID NO: 13) or $N_{20}NGG$ (SEQ ID NO: 14). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., $GGN_{20}NGG$; SEQ ID NO: 15) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length, including the 5' G or GG and the 3' GG or NGG. Yet other guide RNA target sequences plus PAMs can have between 14 and 20 nucleotides in length. Exemplary sgRNA sequences include, but are not limited to SEQ ID NOs: 17-38, 40-41, 43, 48 and 50-55.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

Additional Gene Modifying Agents

In some embodiments, the agent disclosed herein is an agent for genome editing other than a CRISPR/Cas system. Deletion of DNA may be performed using gene therapy to knock-out or disrupt the target gene. A knock-out can be a gene knock-down or the gene can be knocked out by a mutation such as, a point mutation, an insertion, a deletion, a frameshift, or a missense mutation by techniques known in the art, including, but not limited to, retroviral gene transfer. In some embodiments, the agent is a nuclease (e.g., Zinc-finger nucleases or a TALEN) effective to bind and modify at least one of the genes disclosed herein (e.g., an autophagy gene, such as an autophagy gene disclosed herein, or an NF-κB gene, such as an NF-κB gene disclosed herein).

Any nuclease agent that induces a nick or double-strand break into a desired target sequence or any DNA-binding protein that binds to a desired target sequence can be used in the methods and compositions disclosed herein. A naturally occurring or native nuclease agent can be employed so long as the nuclease agent induces a nick or double-strand break in a desired target sequence. Likewise, a naturally occurring or native DNA-binding protein can be employed so long as the DNA-binding protein binds to the desired target sequence. Alternatively, a modified or engineered nuclease agent or DNA-binding protein can be employed. An "engineered nuclease agent or DNA-binding protein" includes a nuclease agent or DNA-binding protein that is engineered (modified or derived) from its native form to specifically recognize a desired target sequence. Thus, an engineered nuclease agent or DNA-binding protein can be derived from a native, naturally occurring nuclease agent or DNA-binding protein or it can be artificially created or synthesized. The engineered nuclease agent or DNA-binding protein can recognize a target sequence, for example, wherein the target sequence is not a sequence that would have been recognized by a native (non-engineered or non-modified) nuclease agent or DNA-binding protein. The modification of the nuclease agent or DNA-binding protein can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of nuclease agents or DNA-binding proteins (i.e., an engineered nuclease agent or DNA-binding protein) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent or DNA-binding protein, wherein the active variants retain the ability to cut at a desired target sequence and hence retain nick or double-strand-break-inducing activity or retain the ability to bind a desired target sequence. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence. The target sequence can be endogenous (or native) to the cell or the target sequence can be exogenous to the cell. A target sequence that is exogenous to the cell is not naturally occurring in the genome of the cell. The target sequence can also exogenous to the polynucleotides of interest that one desires to be positioned at the target locus. In some cases, the target sequence is present only once in the genome of the host cell.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are known (e.g., TAQMAN® qPCR assay, Frendewey et al. (2010) *Methods in Enzymology* 476:295-307, herein incorporated by reference in its entirety for all purposes).

The length of the target sequence can vary, and includes, for example, target sequences that are about 30-36 bp for a zinc finger protein or zinc finger nuclease (ZFN) pair (i.e., about 15-18 bp for each ZFN), about 36 bp for a Transcription Activator-Like Effector (TALE) protein or Transcription Activator-Like Effector Nuclease (TALEN), or about 20 bp for a CRISPR/Cas9 guide RNA.

The target sequence of the DNA-binding protein or nuclease agent can be positioned anywhere in or near the target genomic locus. The target sequence can be located within a coding region of a gene, or within regulatory regions that influence the expression of the gene. A target sequence of the DNA-binding protein or nuclease agent can be located in an intron, an exon, a promoter, an enhancer, a regulatory region, or any non-protein coding region.

One type of DNA-binding protein that can be employed in the various methods and compositions disclosed herein is a Transcription Activator-Like Effector (TALE). A TALE can be fused or linked to, for example, an epigenetic modification domain, a transcriptional activation domain, or a transcriptional repressor domain. Examples of such domains are described with respect to Cas proteins, below, and can also be found, for example, in WO 2011/145121, herein incorporated by reference in its entirety for all purposes. Correspondingly, one type of nuclease agent that can be employed in the various methods and compositions disclosed herein is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease such as FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *Proc. Natl. Acad. Sci. U.S.A.* 107(50:21617-21622; Scholze & Boch (2010) *Virulence* 1:428-432; Christian et al. (2010) *Genetics* 186:757-761; Li et al. (2011) *Nucleic Acids Res.* 39(1):359-372; and Miller et al. (2011) *Nature Biotechnology* 29:143-148, each of which is herein incorporated by reference in its entirety for all purposes.

The non-specific DNA cleavage domain from the end of the FokI endonuclease can be used to construct hybrid nucleases that are active in a yeast assay. These reagents are also active in plant cells and in animal cells. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. The number of amino acid residues between the TALEN DNA binding domain and the FokI cleavage domain may be modified by introduction of a spacer (distinct from the spacer sequence) between the plurality of TAL effector repeat sequences and the FokI endonuclease domain. The spacer sequence may be 12 to 30 nucleotides.

The relationship between amino acid sequence and DNA recognition of the TALEN binding domain allows for designable proteins. In this case artificial gene synthesis is problematic because of improper annealing of the repetitive sequence found in the TALE binding domain. One solution to this is to use a publicly available software program (DNAWorks) to calculate oligonucleotides suitable for assembly in a two-step PCR; oligonucleotide assembly followed by whole gene amplification. A number of modular assembly schemes for generating engineered TALE constructs have also been reported. Both methods offer a systematic approach to engineering DNA binding domains that is conceptually similar to the modular assembly method for generating zinc finger DNA recognition domains.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB), which cells respond to with repair mechanisms.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety for all purposes. In various embodiments, TAL effector nucleases are engineered that cut in or near a target nucleic acid sequence in, for example, a genomic locus of interest, wherein the target nucleic acid sequence is at or near a sequence to be modified.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

Transcription Activator-Like Effector Nucleases (TALENs) are artificial restriction enzymes generated by fusing the TAL effector DNA binding domain to a DNA cleavage domain. These reagents enable efficient, programmable, and specific DNA cleavage and represent powerful tools for genome editing in situ. Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA. See U.S. Ser. No. 12/965,590; U.S. Ser. No. 13/426,991 (U.S. Pat. No. 8,450,471); U.S. Ser. No. 13/427,040 (U.S. Pat. No. 8,440,431); U.S. Ser. No. 13/427,137 (U.S. Pat. No. 8,440,432); and U.S. Ser. No. 13/738,381, all of which are incorporated by reference herein in their entirety.

Another example of a DNA-binding protein is a zinc finger protein. Such zinc finger proteins can be linked or fused to, for example, an epigenetic modification domain, a transcriptional activation domain, or a transcriptional repressor domain. Examples of such domains are described with respect to Cas proteins, below, and can also be found, for example, in WO 2011/145121, herein incorporated by reference in its entirety for all purposes. Correspondingly, another example of a nuclease agent that can be employed in the various methods and compositions disclosed herein is a zinc-finger nuclease (ZFN). In some ZFNs, each monomer of the ZFN comprises three or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US 2006/0246567; US 2008/0182332; US 2002/0081614; US 2003/0021776; WO 2002/057308 A2; US 2013/0123484; US 2010/0291048; WO 2011/017293 A2; and Gaj et al. (2013) *Trends in Biotechnology* 31(7):397-405, each of which is herein incorporated by reference in its entirety for all purposes.

Interfering Nucleic Acid Agents

In certain embodiments, interfering nucleic acid molecules that selectively target and inhibit the activity or expression of a product (e.g., an mRNA product) of an autophagy or NF-κB gene (e.g., a gene listed in Table 1 or Table 2) are provided herein and/or used in methods described herein. In some embodiments, the interfering nucleic acid induces cytotoxicity in cells that express a product of at least one autophagy gene or at least one NF-κB gene (e.g., a gene listed in Table 1 or Table 2). An agent may inhibit the expression or activity of a product (e.g., an mRNA product) of at least one autophagy gene or at least one NF-κB gene by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100%. An agent disclosed herein may comprise at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100% complementarity to a product (e.g., an mRNA product) of at least one autophagy gene or at least one NF-κB gene.

In some embodiments, the inhibiting nucleic acid is a siRNA, a shRNA, a PNA, or a miRNA molecule. Interfering nucleic acids generally include a sequence of cyclic subunits, each bearing a base-pairing moiety, linked by inter-subunit linkages that allow the base-pairing moieties to hybridize to a target sequence in a nucleic acid (typically an RNA) by Watson-Crick base pairing, to form a nucleic acid:oligomer heteroduplex within the target sequence. Interfering RNA molecules include, but are not limited to, antisense molecules, siRNA molecules, single-stranded siRNA molecules, miRNA molecules and shRNA molecules.

Typically at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acid molecule is double-stranded RNA. The double-stranded RNA molecule may have a 2 nucleotide 3' overhang. In some embodiments, the two RNA strands are connected via a hairpin structure, forming a shRNA molecule. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues.

Interfering nucleic acid molecules provided herein can contain RNA bases, non-RNA bases or a mixture of RNA bases and non-RNA bases. For example, interfering nucleic acid molecules provided herein can be primarily composed of RNA bases but also contain DNA bases or non-naturally occurring nucleotides.

The interfering nucleic acids can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, incorporated by reference in their entireties.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA containing compound where each LNA subunit is separated by a DNA subunit. Certain compounds are composed of alternating LNA and DNA subunits where the intersubunit linker is phosphorothioate.

"Phosphorothioates" (or S-oligos) are a variant of normal DNA in which one of the nonbridging oxygens is replaced by a sulfur. The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990). The latter methods avoid the problem of elemental sulfur's insolubility in most organic solvents and the toxicity of carbon disulfide. The TETD and BDTD methods also yield higher purity phosphorothioates.

"2'O-Me oligonucleotides" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphothioate oligonucleotides (PTOs) for further stabilization. 2'O-Me oligonucleotides (phosphodiester or phosphothioate) can be synthesized according to routine techniques in the art (see, e.g., Yoo et al., Nucleic Acids Res. 32:2008-16, 2004).

The interfering nucleic acids described herein may be contacted with a cell or administered to an organism (e.g., a human). Alternatively, constructs and/or vectors encoding the interfering RNA molecules may be contacted with or introduced into a cell or organism. In certain embodiments, a viral, retroviral or lentiviral vector is used. In some embodiments, the vector has a tropism for cardiac tissue. In some embodiments the vector is an adeno-associated virus.

In some embodiments, the interfering nucleic acid molecule is a siRNA molecule. Such siRNA molecules should include a region of sufficient homology to the target region, and be of sufficient length in terms of nucleotides, such that the siRNA molecule down-regulate target RNA. The term "ribonucleotide" or "nucleotide" can, in the case of a modified RNA or nucleotide surrogate, also refer to a modified nucleotide, or surrogate replacement moiety at one or more positions. It is not necessary that there be perfect complementarity between the siRNA molecule and the target, but the correspondence must be sufficient to enable the siRNA molecule to direct sequence-specific silencing, such as by RNAi cleavage of the target RNA. In some embodiments, the sense strand need only be sufficiently complementary with the antisense strand to maintain the overall double-strand character of the molecule.

In addition, an siRNA molecule may be modified or include nucleoside surrogates. Single stranded regions of an siRNA molecule may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA molecule, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

Non-limiting examples of shRNAs include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In some embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional embodiments related to the shRNAs, as well as methods of designing and synthesizing such shRNAs, are described in U.S. patent application publication number 2011/0071208, the disclosure of which is herein incorporated by reference in its entirety for all purposes.

In some embodiments, provided herein are micro RNAs (miRNAs). miRNAs represent a large group of small RNAs produced naturally in organisms, some of which regulate the expression of target genes. miRNAs are formed from an approximately 70 nucleotide single-stranded hairpin precursor transcript by Dicer. miRNAs are not translated into proteins, but instead bind to specific messenger RNAs, thereby blocking translation. In some instances, miRNAs base-pair imprecisely with their targets to inhibit translation.

In certain embodiments, antisense oligonucleotides may be 100% complementary to the target sequence, or may include mismatches, e.g., to improve selective targeting of allele containing the disease-associated mutation, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence. Oligonucleotide backbones that are less susceptible to cleavage by nucleases are discussed herein. Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability.

Interfering nucleic acid molecules can be prepared, for example, by chemical synthesis, in vitro transcription, or digestion of long dsRNA by Rnase III or Dicer. These can be introduced into cells by transfection, electroporation, or other methods known in the art. See Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052.

In the present methods, an interfering nucleic acid molecule or an interfering nucleic acid encoding polynucleotide can be administered to the subject, for example, as naked nucleic acid, in combination with a delivery reagent, and/or as a nucleic acid comprising sequences that express an interfering nucleic acid molecule. In some embodiment, the interfering nucleic acid is administered directly to a tumor in a subject. In some embodiments, the nucleic acid comprising sequences that express the interfering nucleic acid molecules are delivered within vectors, e.g. plasmid, viral and bacterial vectors. Any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Res., 32(13): e109 (2004); Hanai et al. Ann NY Acad Sci., 1082:9-17 (2006); and Kawata et al. Mol Cancer Ther., 7(9):2904-12 (2008); each of which is incorporated herein in their entirety. Exemplary interfering nucleic acid delivery systems are provided in U.S. Pat. Nos. 8,283,461, 8,313,772, 8,501,930, 8,426,554, 8,268,798 and 8,324,366, each of which is hereby incorporated by reference in its entirety.

In some embodiments of the methods described herein, liposomes are used to deliver an inhibitory oligonucleotide to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Small Molecule Agents

Certain embodiments of the methods and compositions disclosed herein relate to the use of small molecule agents e.g., small molecule agents that inhibit the expression or activity of a product of a an autophagy gene (e.g., an autophagy gene disclosed herein) or an NF-κB gene (e.g., an NF-κB gene disclosed herein) in a cancer cell. In some embodiments, the small molecule induces cytotoxicity in cells that express a product of a an autophagy gene (e.g., an autophagy gene disclosed herein) or an NF-κB gene (e.g., an NF-κB gene disclosed herein). Such agents include those known in the art and those identified using the screening assays described herein. A small molecule provided herein may have at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100% specificity for a product of an autophagy gene (e.g., an autophagy gene disclosed herein) or an NF-κB gene (e.g., an NF-κB gene disclosed herein).

In certain embodiments, the agent may be a small molecule autophagy inhibitor such as a PI3-kinase inhibitor, a phosphoinositide3-kinase (PI3) inhibitor, an Unc-51-like kinase 1 (ULK1) inhibitor, a vacuolar protein sorting protein 18 (Vps18) inhibitor, a vacuolar protein sorting protein 34 (Vps34) inhibitor, a ubiquitin-specific peptidases (USP10 or USP13) inhibitor, a thioxanthone-based autophagy inhibitor, an ATG4 inhibitor, autophinib, 3-methyladenine, Wortmannin, ammonium chloride, bafilomycin A1, eflornithine, leupeptin, betulinic acid, CA074, colchicine, thapsigargin, vacuolin-1, vinblastine, desmethyl clomipramine, LY294002, PT210, GSK-2126458, Spautin-1, SAR405, Compound 31, VPS34-IN1, PIK-III, Compound 6, MRT68921, SBI-0206965, pepstatin A, E64d, clomipramine, lucanthone, chloroquine, hydroxychlorquine, monensin, Lys05, ARN5187, Compound 30, MPT0L145, ROC325, Verteporfin, NSC185058, and NSC377071. Additional autophagy inhibitors and details regarding autophagy inhibitors can be found in Waleska K. Martins and Mauricio S. Baptista (Nov. 10, 2016). Autophagy Modulation for Organelle-Targeting Therapy, Autophagy in Current Trends in Cellular Physiology and Pathology, Nikolai V. Gorbunov and Marion Schneider, IntechOpen, DOI: 10.5772/63976 (available from: https://www.intechopen.com/books/autophagy-in-current-trends-in-cellular-physiology-and-pathology/autophagy-modulation-for-organelle-targeting-therapy); Pasquier, Benoit. "Autophagy inhibitors." Cellular and Molecular Life Sciences 73 (2015): 985-1001; U.S. Pat. Nos. 8,524,762 and 9,926,326; and WIPO publication WO2011011522, each of which is hereby incorporated by reference in its entirety.

In some embodiments, the agent may be an inhibitor of the NF-κB pathway. Small molecule autophagy inhibitors include IKK and IκB phosphorylation inhibitors, IκB degradation inhibitors, proteasome and protease inhibitors, IκBα upregulation, NF-κB nuclear translocation, and NF-κB expression inhibitors, NF-κB DNA-binding inhibitors, NF-κB transactivation inhibitors, antioxidants, or upstream target inhibitors. A list of NF-κB inhibitors can be found in Gilmore, T., Herscovitch, M. "Inhibitors of NF-κB signaling: 785 and counting." Oncogene 25, 6887-6899 (2006), which is hereby incorporated by reference in its entirety.

Agents useful in the methods disclosed herein may be obtained from any available source, including systematic libraries of natural and/or synthetic compounds. Agents may also be obtained by any of the numerous approaches in combinatorial library methods known in the art, including:

biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

Agents useful in the methods disclosed herein may be identified, for example, using assays for screening candidate or test agents e.g., agents that decrease the activity or expression of a product of an autophagy gene (e.g., an autophagy gene disclosed herein) or an NF-κB gene (e.g., an NF-κB gene disclosed herein).

Agent Delivery

The nucleic acid and protein agents disclosed herein (e.g., CRISPR/Cas agents, TALEN agents, ZFN agents, interfering nucleic acid agents) can be introduced into a cell (e.g., a cancer cell) by any available means. "Introducing" includes presenting to the cell the nucleic acid or protein in such a manner that the sequence gains access to the interior of the cell. The introducing can be accomplished by any means, and one or more of the components (e.g., two of the components, or all of the components) can be introduced into the cell simultaneously or sequentially in any combination. Contacting the genome of a cell with a nuclease agent can comprise introducing one or more nuclease agents or nucleic acids encoding nuclease agents (e.g., one or more Cas proteins or nucleic acids encoding one or more Cas proteins, and one or more guide RNAs or nucleic acids encoding one or more guide RNAs (i.e., one or more CRISPR RNAs and one or more tracrRNAs)) into the cell. Contacting the genome of cell (i.e., contacting a cell) can comprise introducing only one of the above components, one or more of the components, or all of the components into the cell.

In some embodiments, suitable delivery methods for nucleic acid and protein agents provided herein include, but are not limited to electroporation, iTOP, lipid nanoparticles, polymer nanoparticles, CPP delivery, DNA nanostructure, or gold nanoparticles.

Suitable delivery methods for nucleic acid agents disclosed herein (e.g., plasmid based gRNA-Cas, Ca9 mRNA, sgRNA, interfering nucleic acid agents) include, but are not limited to electroporation, hydrodynamic injection, microinjection, mechanical cell deformation, lipid nanoparticles, AAV, or lentivirus.

A nuclease agent can be introduced into the cell in the form of a protein or in the form of a nucleic acid encoding the nuclease agent, such as an RNA (e.g., messenger RNA (mRNA)) or DNA. When introduced in the form of a DNA, the DNA can be operably linked to a promoter active in the cell. Such DNAs can be in one or more expression constructs.

For example, a Cas protein can be introduced into the cell in the form of a protein, such as a Cas protein complexed with a gRNA, or in the form of a nucleic acid encoding the Cas protein, such as an RNA (e.g., messenger RNA (mRNA)) or DNA. A guide RNA can be introduced into the cell in the form of an RNA or in the form of a DNA encoding the guide RNA. When introduced in the form of a DNA, the DNA encoding the Cas protein and/or the guide RNA can be operably linked to a promoter active in the cell. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs, DNAs encoding one or more tracrRNAs, and DNA encoding a Cas protein can be components of separate nucleic acid molecules).

The disclosure herein also provides a pharmaceutical composition comprising one or a cocktail of gRNA molecules that target autophagy or NF-kB gene expression, and a pharmaceutically acceptable carrier. For example, the present invention provides pharmaceutical compositions that each include one, two, three, or more gRNA molecules that target autophagy or NF-kB genes.

Agents provided herein may include gRNAs encapsulated within lipid particles. With respect to formulations that include a cocktail of gRNAs encapsulated within lipid particles, the different gRNA molecules may be co-encapsulated in the same lipid particle, or each type of gRNA species present in the cocktail may be encapsulated in separate particles, or some gRNA species may be coencapsulated in the same particle while other gRNA species are encapsulated in different particles within the formulation. In certain embodiments, the lipid particles comprise both gRNA and an mRNA encoding a Cas protein. In certain embodiments, one population lipid particles comprises the gRNA and another population of lipid particles comprises Cas protein(s) or mRNA encoding Cas protein(s), which lipid particles may be in the same composition or in different compositions, and may be administered concurrently or sequentially.

In some embodiments, the lipid particle is formed from a cationic lipid, a non-cationic lipid, and optionally a conjugated lipid that prevents aggregation of the particle. A lipid particle that includes a nucleic acid molecule (e.g., gRNA molecule) is referred to as a nucleic acid-lipid particle. The nucleic acid may be fully encapsulated within the lipid particle, thereby protecting the nucleic acid from enzymatic degradation. In some embodiments, the nucleic acid-lipid particle has a total lipid:gRNA mass ratio of from about 5:1 to about 15:1. In certain embodiments, the nucleic acid-lipid particle has a total lipid:gRNA mass ratio of from about 5:1 to about 15:1, or about 5:1, 6:1, 7:1, 8:1, 9:1, 10:1, 11:1, 12:1, 13:1, 14:1, or 15:1, or any fraction thereof or range therein. In certain embodiments, the nucleic acid-lipid particle has a total lipid:gRNA mass ratio of about 9:1 (e.g., a lipid:drug ratio of from 8.5:1 to 10:1, or from 8.9:1 to 10:1, or from 9:1 to 9.9:1, including 9.1:1, 9.2:1, 9.3:1, 9.4:1, 9.5:1, 9.6:1, 9.7:1, and 9.8:1). Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal. In particular embodiments, the nucleic acid-lipid particle is administered systemically, e.g., via enteral or parenteral routes of administration. The nucleic acid may be complexed with a condensing agent and encapsulated within a lipid particle as set forth in PCT Publication No. WO 00/03683, the disclosure of which is herein incorporated by reference in its entirety for all purposes.

The lipid particles provided herein may have a mean diameter of from about 30 nm to about 150 nm, from about 40 nm to about 150 nm, from about 50 rim to about 150 nm, from about 60 nm to about 130 nm, from about 70 rim to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 rim, 95 nm, 100 nm, 105 nm, 110 nm, 115 nm, 120 nm, 125 nm, 130 nm, 135 nm, 140 nm, 145 rim, or 150 nm. Nucleic acid-lipid particles and their method of preparation are disclosed in, e.g., U.S. Patent Publication Nos. 20040142025 and 20070042031, the disclosures of which are herein incorporated by reference in their entirety for all purposes.

The nucleic acid-lipid particles may comprise a lipid conjugate. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain embodiments, non-ester containing linker moieties, such as amides or carbamates, are used.

In some embodiments, the lipid conjugate in the nucleic acid-lipid particles inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-lipid conjugate is selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof. In certain embodiments, the PEG-lipid conjugate is a PEG-DAA conjugate. In certain embodiments, the PEG-DAA conjugate in the lipid particle may comprise a PEG-didecyloxypropyl (C10) conjugate, a PEG-dilauryloxypropyl (C12) conjugate, a PEG-dimyristyloxypropyl (C14) conjugate, a PEG-dipalmityloxypropyl (C16) conjugate, a PEG-distearyloxypropyl (C18) conjugate, or mixtures thereof. In certain embodiments, wherein the PEG-DAA conjugate is a PEG-dimyristyloxypropyl (C14) conjugate. In another embodiment, the PEG-DAA conjugate is a compound (66) (PEG-C-DMA) conjugate. In another embodiment, the lipid conjugate comprises a POZ-lipid conjugate such as a POZ-DAA conjugate.

In certain embodiments, the conjugated lipid that inhibits aggregation of particles comprises from about 0.5 mol % to about 3 mol % of the total lipid present in the particle.

Additional embodiments of useful formulations are described in published US patent application publication number US 2011/0076335 A1 and US 2018/0245074 A1, the disclosure of which is herein incorporated by reference in its entirety for all purposes.

In certain embodiments, the nucleic acid agents provided herein (e.g., Cas protein-encoding and/or gRNA-encoding DNA) is delivered by a vector (e.g., viral vector/virus or plasmid).

Vectors can comprise a sequence that encodes a Cas protein and/or a gRNA molecule, and/or a donor template with high homology to the region (e.g., target sequence) being targeted. In certain embodiments, the donor template comprises all or part of a target sequence. Exemplary donor templates are a repair template, e.g., a gene correction template, or a gene mutation template, e.g., point mutation (e.g., single nucleotide (nt) substitution) template). A vector can also comprise a sequence encoding a signal peptide (e.g., for nuclear localization, nucleolar localization, or mitochondrial localization), fused, e.g., to a Cas molecule sequence. For example, the vectors can comprise a nuclear localization sequence (e.g., from SV40) fused to the sequence encoding the Cas molecule.

One or more regulatory/control elements, e.g., promoters, enhancers, introns, polyadenylation signals, a Kozak consensus sequences, internal ribosome entry sites (IRES), a 2A sequence, and splice acceptor or donor can be included in the vectors. In certain embodiments, the promoter is recognized by RNA polymerase II. In other embodiments, the promoter is recognized by RNA polymerase III (e.g., a U6 promoter). In certain embodiments, the promoter is a regulated promoter (e.g., inducible promoter). In certain embodiments, the promoter is a constitutive promoter. In certain embodiments, the promoter is a tissue specific promoter. In certain embodiments, the promoter is a viral promoter. In certain embodiments, the promoter is a non-viral promoter.

In certain embodiments, the vector or delivery vehicle is a viral vector (e.g., for generation of recombinant viruses). In certain embodiments, the virus is a DNA virus (e.g., dsDNA or ssDNA virus). In certain embodiments, the virus is an RNA virus (e.g., an ssRNA virus). In certain embodiments, the virus infects dividing cells. In other embodiments, the virus infects non-dividing cells. Exemplary viral vectors/viruses include, e.g., retroviruses, lentiviruses, adenovirus, adeno-associated virus (AAV), vaccinia viruses, poxviruses, and herpes simplex viruses.

In certain embodiments, the virus infects dividing cells. In other embodiments, the virus infects non-dividing cells. In certain embodiments, the virus infects both dividing and non-dividing cells. In certain embodiments, the virus can integrate into the host genome. In certain embodiments, the virus is engineered to have reduced immunity, e.g., in human. In certain embodiments, the virus is replication-competent. In other embodiments, the virus is replication-defective, e.g., having one or more coding regions for the genes necessary for additional rounds of virion replication and/or packaging replaced with other genes or deleted. In certain embodiments, the virus causes transient expression of the Cas molecule or molecules and/or the gRNA molecule or molecules. In other embodiments, the virus causes long-lasting, e.g., at least 1 week, 2 weeks, 1 month, 2 months, 3 months, 6 months, 9 months, 1 year, 2 years, or permanent expression, of the Cas molecule or molecules and/or the gRNA molecule or molecules. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In certain embodiments, the viral vector recognizes a specific cell type or tissue. For example, the viral vector can be pseudotyped with a different/alternative viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

Exemplary viral vectors/viruses include, e.g., retroviruses, lentiviruses, adenovirus, adeno-associated virus (AAV), vaccinia viruses, poxviruses, and herpes simplex viruses.

In certain embodiments, the Cas- and/or gRNA-encoding sequence is delivered by a recombinant retrovirus. In certain embodiments, the retrovirus (e.g., Moloney murine leukemia virus) comprises a reverse transcriptase, e.g., that allows integration into the host genome. In certain embodiments, the retrovirus is replication-competent.

In certain embodiments, the retrovirus is replication-defective, e.g., having one of more coding regions for the genes necessary for additional rounds of virion replication and packaging replaced with other genes, or deleted.

In certain embodiments, the Cas- and/or gRNA-encoding nucleic acid sequence (optionally the donor template nucleic acid) is delivered by a recombinant lentivirus. For example, the lentivirus is replication-defective, e.g., does not comprise one or more genes required for viral replication.

In certain embodiments, the Cas- and/or gRNA-encoding nucleic acid sequence (optionally the donor template nucleic acid) is delivered by a recombinant adenovirus.

In certain embodiments, the adenovirus is engineered to have reduced immunity in human. In certain embodiments, the Cas- and/or gRNA-encoding nucleic acid sequence (optionally the donor template nucleic acid) is delivered by a recombinant AAV. In certain embodiments, the AAV does not incorporate its genome into that of a host cell, e.g., a target cell as describe herein. In certain embodiments, the AAV can incorporate at least part of its genome into that of a host cell, e.g., a target cell as described herein. In certain embodiments, the AAV is a self-complementary adeno-associated virus (scAAV), e.g., a scAAV that packages both strands which anneal together to form double stranded DNA. AAV serotypes that may be used in the disclosed methods, include AAV1, AAV2, modified AAV2 (e.g., modifications at Y444F, Y500F, Y730F and/or S662V), AAV3, modified AAV3 (e.g., modifications at Y705F, Y73 IF and/or T492V), AAV4, AAV5, AAV6, modified AAV6 (e.g., modifications at S663 V and/or T492V), AAV8, AAV 8.2, AAV9, AAV rhlO, and pseudotyped AAV, such as AAV2/8, AAV2/5 and AAV2/6 can also be used in the disclosed methods. In certain embodiments, an AAV capsid that can be used in the methods described herein is a capsid sequence from serotype AAV1, AAV2, AAV3, AAV4, AAV5, AAV6, AAV7, AAV8, AAV9, AAV.rh8, AAV.rhlO, AAV.rh32/33, AAV.rh43, AAV.rh64R1, or AAV7m8.

In certain embodiments, the Cas- and/or gRNA-encoding nucleic acid sequence (optionally the donor template nucleic acid) is delivered in a re-engineered AAV capsid, e.g., with about 50% or greater, e.g., about 60% or greater, about 70% or greater, about 80%) or greater, about 90% or greater, or about 95% or greater, sequence homology with a capsid sequence from serotypes AAV1, AAV2, AAV3, AAV4, AAV5, AAV6, AAV7, AAV8, AAV9, AAV.rh8, AAV.rhlO, AAV.rh32/33, AAV.rh43, or AAV.rh64R1.

In certain embodiments, the Cas- and/or gRNA-encoding nucleic acid sequence (optionally the donor template nucleic acid) is delivered by a chimeric AAV capsid. Exemplary chimeric AAV capsids include, but are not limited to, AAV9i1, AAV2i8, AAV-DJ, AAV2G9, AAV2i8G9, or AAV8G9.

In certain embodiments, the AAV is a self-complementary adeno-associated virus (scAAV), e.g., a scAAV that packages both strands which anneal together to form double stranded DNA.

In certain embodiments, the Cas9- and/or gRNA-encoding DNA (optionally the donor template nucleic acid) is delivered by a hybrid virus, e.g., a hybrid of one or more of the viruses described herein. In certain embodiments, the hybrid virus is hybrid of an AAV (e.g., of any AAV serotype), with a Bocavirus, B 19 virus, porcine AAV, goose AAV, feline AAV, canine AAV, or MVM. Additional information on viral vector delivery of agents can be found in WIPO publication WO2018081504 A1, incorporated by referenced in its entirety.

In certain embodiments, the delivery vehicle is a non-viral vector. In certain embodiments, the non-viral vector is an inorganic nanoparticle. Exemplary inorganic nanoparticles include, e.g., magnetic nanoparticles (e.g., Fe3MnO2) and silica. The outer surface of the nanoparticle can be conjugated with a positively charged polymer (e.g., polyethylenimine, polylysine, polyserine) which allows for attachment (e.g., conjugation or entrapment) of payload.

In some methods, DNA encoding a nuclease agent (e.g., a Cas protein and a guide RNA) can be introduced into a cell via DNA minicircles. See, e.g., WO 2014/182700, herein incorporated by reference in its entirety for all purposes. DNA minicircles are supercoiled DNA molecules that can be used for non-viral gene transfer that have neither an origin of replication nor an antibiotic selection marker. Thus, DNA minicircles are typically smaller in size than plasmid vector. These DNAs are devoid of bacterial DNA, and thus lack the unmethylated CpG motifs found in bacterial DNA.

The methods provided herein do not depend on a particular method for introducing a nucleic acid or protein into the cell, only that the nucleic acid or protein gains access to the interior of a least one cell. Methods for introducing nucleic acids and proteins into various cell types are known and include, for example, stable transfection methods, transient transfection methods, and virus-mediated methods.

Transfection protocols as well as protocols for introducing nucleic acids or proteins into cells may vary. Non-limiting transfection methods include chemical-based transfection methods using liposomes; nanoparticles; calcium phosphate (Graham et al. (1973) Virology 52 (2): 456-67, Bacchetti et al. (1977) Proc. Natl. Acad. Sci. USA 74 (4): 1590-4, and Kriegler, M (1991). Transfer and Expression: A Laboratory Manual. New York: W.H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell can also be accomplished by microinjection. Microinjection of an mRNA is preferably into the cytoplasm (e.g., to deliver mRNA directly to the translation machinery), while microinjection of a protein or a DNA encoding a Cas protein is preferably into the nucleus. Alternatively, microinjection can be carried out by injection into both the nucleus and the cytoplasm: a needle can first be introduced into the nucleus and a first amount can be injected, and while removing the needle from the cell a second amount can be injected into the cytoplasm. If a nuclease agent protein is injected into the cytoplasm, the protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein.

Introduction of nucleic acids and proteins into cells can also be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule.

In some cases, the cells employed in the methods and compositions have a DNA construct stably incorporated into their genome. In such cases, the contacting can comprise providing a cell with the construct already stably incorporated into its genome. For example, a cell employed in the methods disclosed herein may have a preexisting Cas-encoding gene stably incorporated into its genome (i.e., a Cas-ready cell). "Stably incorporated" or "stably introduced" or "stably integrated" includes the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

The DNA-binding protein or nuclease agent may be introduced into the cell by any known means. A polypeptide encoding the DNA-binding protein or nuclease agent may be directly introduced into the cell. Alternatively, a polynucleotide encoding the DNA-binding protein or nuclease agent can be introduced into the cell. When a polynucleotide encoding the DNA-binding protein or nuclease agent is introduced into the cell, the DNA-binding protein or nuclease agent can be transiently, conditionally, or constitutively expressed within the cell. For example, the polynucleotide encoding the DNA-binding protein or nuclease agent can be contained in an expression cassette and be operably linked to a conditional promoter, an inducible promoter, a constitutive promoter, or a tissue-specific promoter. Such promoters are discussed in further detail elsewhere herein. Alternatively, the DNA-binding protein or nuclease agent can be introduced into the cell as an mRNA encoding a DNA-binding protein or a nuclease agent.

A polynucleotide encoding a DNA-binding protein or nuclease agent can be stably integrated in the genome of the cell and operably linked to a promoter active in the cell. Alternatively, a polynucleotide encoding a DNA-binding protein or nuclease agent can be in a targeting vector or in a vector or a plasmid that is separate from the targeting vector comprising the insert polynucleotide.

When the DNA-binding protein or nuclease agent is provided to the cell through the introduction of a polynucleotide encoding the DNA-binding protein or nuclease agent, such a polynucleotide encoding a DNA-binding protein or nuclease agent can be modified to substitute codons having a higher frequency of usage in the cell of interest, as compared to the naturally occurring polynucleotide sequence encoding the DNA-binding protein or nuclease agent. For example, the polynucleotide encoding the DNA-binding protein or nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

Therapeutic Methods

In some aspects, provided herein are methods of sensitizing cancer cells in a subject to TNF-α mediated killing by administering to the subject an agent (e.g., an agent disclosed herein) that inhibits autophagy and/or the NF-κB pathway in the cancer cells. In other aspects, provided herein are methods of increasing TNF-α mediated killing of cancer cells in a subject by administering to the subject at least one agent (e.g., an agent disclosed herein) that inhibits autophagy and/or the NF-κB pathway in the cancer cells. In additional aspects, the methods described herein include methods of sensitizing a tumor in a subject to TNF-α mediated killing or increasing TNF-α mediated killing of a tumor in a subject by administering to the subject an agent (e.g., an agent disclosed herein) that inhibits autophagy and/or the NF-κB pathway in the tumor.

Also provided herein are methods of treating cancer in a subject by administering to the subject an agent (e.g., an agent disclosed herein) that inhibits autophagy and/or the NF-κB pathway in cancer cells in the subject and an additional cancer therapy. In some embodiments the additional cancer therapy is a cancer immunotherapy. In certain embodiments, the additional therapy is a therapy that induces TNF-α mediated killing of cancer cells. In some embodiments, the additional therapy is a therapy that induces T cell killing of cancer cells (e.g., cytotoxic T cell killing of cancer cells). In some embodiments, the additional cancer therapy comprises immune checkpoint inhibition, TNF-α administration, T cell immunotherapy (e.g., CAR-T cell immunotherapy) and/or a cancer vaccine.

Thus, in certain embodiments, agents of the invention may be used alone or conjointly administered with another type of therapeutic agent. For example, the different therapeutic agents can be administered either in the same formulation or in separate formulations, either concomitantly or sequentially. In certain embodiments, the different therapeutic agents can be administered within about one hour, about 12 hours, about 24 hours, about 36 hours, about 48 hours, about 72 hours, or about a week of one another. Thus, a subject who receives such treatment can benefit from a combined effect of different therapeutic agents.

In certain embodiments, provided herein is a composition, e.g., a pharmaceutical composition, containing at least one agent described herein together with a pharmaceutically acceptable carrier. In one embodiment, the composition includes a combination of multiple (e.g., two or more, three or more, four or more, or five or more) agents described herein.

In some embodiments, the pharmaceutical composition is delivered locally or systemically. In some embodiments, the pharmaceutical composition may be administered locally to a tumor present in the subject or the tumor microenvironment. In some embodiments, the agent or pharmaceutical composition is administered with a second cancer therapeutic agent.

The agents described herein may be administered conjointly with any other cancer therapy, including immunotherapies. Additional cancer therapies include immune checkpoint inhibition. In some embodiments, the immune checkpoint inhibitor inhibits an immune checkpoint protein. Immune checkpoint inhibition broadly refers to inhibiting the checkpoints that cancer cells can produce to prevent or downregulate an immune response. Examples of immune checkpoint proteins are CTLA-4, PD-1, VISTA, B7-H2, B7-H3, PD-L1, B7-H4, B7-H6, ICO5, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, butyrophilins, A2aR, and combinations thereof. The immune checkpoint inhibitor may be cemiplimab (REGN2810), nivolumab (BMS-936558, MDX-1106, ONO-4538), pembrolizumab (MK-3475, SCH 900475), atezolizumab (MPDL3280A, RG7446, RO5541267), durvalumab (MEDI4736, MEDI-4736), avelumab (MSB0010718C), ipilimumab (BMS-734016, IBI310, MDX-010), SHR1210, sintilimab (MI308), spartalizumab (PDR001), tislelizumab (BGB-A317), pidilizumab, BCD-100, toripalimab (JS001), BAY 1905254, ASP 8374, PF-06801591, AMP-224, AB122, AK105, AMG 404, BCD-100, BI 754091, F520, HLX10, HX008, JTX-4014, LZMO09, MEDI0680, MGA012, Sym021, TSR-042, PSB205, MGD019, MGD013, AK104, XmAb20717, RO7121661, CX-188, INCB086550, FS118, BCD-135, BGB-A333, CBT-502, CK-301, CS1001, FAZ053, HLX20, KN035, MDX-1105, MSB2311, SHR-1316, TG-1501, ZKAB001, INBRX-105, MCLA-145, KN046, M7824, LY3415244, INCB086550, CA-170, CX-072, ADU-1604, AGEN1181, AGEN1884, MK-1308, REGN4659, XmAb22841, ATOR-1015, PSB205, MGD019, AK104, XmAb20717, BMS-986249, tremelimumab, BMS-986258, BGB-A425, INCAGN02390, Sym023, JNJ 61610588, BI 754111, LAG525, MK-4280, REGN3767, Sym022, TSR-033, relatlimab, JTX-2011, MGD009, BMS-986207, OMP-313M32, MK-7684 or TSR-022.

Additional cancer immunotherapies include adoptive immunotherapies such as autologous or allogenic T cell therapy or autologous or allogenic CAR T cell therapy. Adoptive immunotherapy is a treatment method designed to boost a patient's immune response against a tumor or cancer cells. The method involves the removal of immune cells from an individual, the forming of effector cells ex vivo, the expansion of the cells to clinically-relevant numbers and the re-infusion of the cells into the patient. Provided herein are methods that include conjoint administration of an agent disclosed herein and an allogeneic or autologous CTLs expressing a T cell receptor that specifically binds to an peptide (e.g., a cancer peptide or a subject-specific peptide) presented on a class I MHC. In some embodiments, the CTLs are from a cell bank or from the subject to which the CTLs are being administered. In some embodiments, the MHC is a class I MHC. In some embodiment, the class II MHC has an α chain polypeptide that is HLA-DMA, HLA-DOA, HLA-DPA, HLA-DQA or HLA-DRA. In some embodiments, the class II MHC has a β chain polypeptide that is HLA-DMB, HLA-DOB, HLA-DPB, HLA-DQB or HLA-DRB. In some embodiments, the CTLs are stored in a cell library or bank before they are administered to the subject.

In some embodiments, T cells are contacted with antigen presenting cells (APCs) that present a peptide specific to the cancer or tumor in the subject. In some embodiments the APCs are B cells, antigen presenting T-cells, dendritic cells, or artificial antigen-presenting cells (e.g., aK562 cells). Dendritic cells for use in the process may be prepared by taking PBMCs from a patient sample and adhering them to plastic. Generally, the monocyte population sticks and all other cells can be washed off. The adherent population is then differentiated with IL-4 and GM-CSF to produce monocyte derived dendritic cells. These cells may be matured by the addition of IL-1β, IL-6, PGE-1 and TNF-α (which upregulates the important co-stimulatory molecules on the surface of the dendritic cell) and are then transduced with one or more of the peptides provided herein. In some embodiments, the APC is an artificial antigen-presenting cell, such as an aK562 cell. In some embodiments, the artificial antigen-presenting cells are engineered to express CD80, CD83, 41BB-L, and/or CD86. Exemplary artificial antigen-presenting cells, including aK562 cells, are described U.S. Pat. Pub. No. 2003/0147869, which is hereby incorporated by reference. Exemplary methods of producing antigen presenting cells can be found in WO2013088114, hereby incorporated in its entirety.

Another exemplary adoptive immunotherapy protocol involves the administration of autologous tumor infiltrating lymphocytes (TIL). TIL cells are potent at killing. TIL cells are effector cells differentiated in vivo in solid tumors (see, U.S. Pat. No. 5,126,132, which describes a method for generating TIL cells for adoptive immunotherapy of cancer). TIL cells may be produced, for example, by removing a tumor sample from a patient, isolating lymphocytes that were infiltrating into 10 the tumor sample, growing these TIL cells ex vivo in the presence of IL-2 and reinfusing the cells to the patient along with IL-2.

The additional cancer therapy may be CAR-T cell therapy. Chimeric antigen receptors (CAR) are molecules combining antibody-based specificity for tumor-associated surface antigens with T cell receptor-activating intracellular domains with specific anti-tumor cellular immune activity (Eshhar, 1997, Cancer Immunol Immunother 45(3-4) 131-136; Eshhar et al., 1993, Proc Natl Acad Sci USA 90(2): 720-724; Brocker and Karjalainen, 1998, Adv Immunol 68:257-269). These CARs allow a T cell to achieve MHC-independent primary activation through single chain Fv (scFv) antigen-specific extracellular regions fused to intracellular domains that provide T cell activation and co-stimulatory signals. Second and third generation CARs also provide appropriate co-stimulatory signals via CD28 and/or CD137 (4-1BB) intracellular activation motifs, which augment cytokine secretion and anti-tumor activity in a variety of solid tumor and leukemia models (Pinthus, et al, 2004, J Clin Invest 114(12):1774-1781; Milone, et al., 2009, Mol Ther 17(8):1453-1464; Sadelain, et al., 2009, Curr Opin Immunol 21(2):215-223). Chimeric Antigen Receptor (CAR) T cell therapy involves genetic modification of patient's autologous T-cells to express a CAR specific for a tumor antigen, following by ex vivo cell expansion and re-infusion back to the patient. CARs are fusion proteins of a selected single-chain fragment variable from a specific monoclonal antibody and one or more T cell receptor intracellular signaling domains. This T cell genetic modification may occur either via viral-based gene transfer methods or nonviral methods, such as DNA-based transposons, CRISPR/Cas9 technology or direct transfer of in vitro transcribed-mRNA by electroporation.

Also provided herein are methods of treating cancer in a subject by obtaining a sample comprising T-cells from the subject, isolating the cytotoxic T lymphocytes (CTLs) from the sample, expanding the CTLs ex vivo, and administering to the subject the expanded CTLs conjointly with at least one agent (e.g., any agent disclosed herein). The cytotoxic T cells may be tumor-infiltrating lymphocytes. Expanding the CTLs may comprise contacting the CTLs with antigen presenting cells (APCs) expressing a cancer-specific or tumor-specific antigen to create antigen-specific CTLs. In some embodiments, the sample comprising T-cells or the isolated CTLs is irritated prior to administration to the subject. The method may further comprises contacting the CTLs with an anti-CD3 monoclonal antibody (OKT3) prior to administration to the subject. In other embodiments, the method further comprises contacting the CTLs with human interleukin (IL)-2 prior to administration to the subject.

In some embodiments, the subject has received a chemotherapy drug prior to administration of the agent. The subject may be refractory to a chemotherapy drug. The subject may receive a chemotherapeutic agent sequentially or simultaneously to receiving an agent of additional cancer therapy disclosed herein. Chemotherapeutic agents include alkylating agents such as thiotepa and cyclophosphamide (Cytoxan™); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide, and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin philI); dynemicin, including dynemicin A; bisphosphonates, such as clodronate; an esperamicin; as well as neocarzinostatin chromophore and related chromoprotein enediyne antibiotic chrommomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (Taxol™, Bristol Meyers Squibb Oncology, Princeton, N.J.) and docetaxel (Taxoteret™, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™) letrozole (Femara™), and anastrozole (Arimidex™); and anti-androgens such as flutamide, nilutamide, bicalutamide, leuprohde, and goserelin; and pharmaceutically acceptable salts, acids or derivatives of any of the above.

As described in detail below, the pharmaceutical compositions and/or agents disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous, intrathecal, intracerebral or epidural injection as, for example, a sterile solution or suspension, or sustained-release formulation. Methods of preparing pharmaceutical formulations or compositions include the step of bringing into association an agent described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Indications

In some embodiments, the methods described herein may be used to treat any cancer, including any cancerous or pre-cancerous tumor. Cancers that may be treated by methods and compositions provided herein include, but are not limited to, cancer of the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; bronchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometrioid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; mammary paget's disease; acinar cell carcinoma; adenosquamous carcinoma; adenocarcinoma w/squamous metaplasia; malignant thymoma; malignant ovarian stromal tumor; malignant thecoma; malignant granulosa cell tumor; and malignant roblastoma; sertoli cell carcinoma; malignant leydig cell tumor; malignant lipid cell tumor; malignant paraganglioma; malignant extra-mammary paraganglioma; pheochromocytoma; glomangiosarcoma; malignant melanoma; amelanotic melanoma; superficial spreading melanoma; malignant melanoma in giant pigmented nevus; epithelioid cell melanoma; malignant blue nevus; sarcoma; fibrosarcoma; malignant fibrous histiocytoma; myxosarcoma; liposarcoma; leiomyosarcoma; rhabdomyosarcoma; embryonal rhabdomyosarcoma; alveolar rhabdomyosarcoma; stromal sarcoma; malignant mixed tumor; mullerian mixed tumor; nephroblastoma; hepatoblastoma; carcinosarcoma; malignant mesenchymoma; malignant brenner tumor; malignant phyllodes tumor; synovial sarcoma; malignant mesothelioma; dysgerminoma; embryonal carcinoma; malignant teratoma; malignant struma ovarii; choriocarcinoma; malignant mesonephroma; hemangiosarcoma; malignant hemangioendothelioma; kaposi's sarcoma; malignant hemangiopericytoma; lymphangiosarcoma; osteosarcoma; juxtacortical osteosarcoma; chondrosarcoma; malignant chondroblastoma; mesenchymal chondrosarcoma; giant cell tumor of bone; ewing's sarcoma; malignant odontogenic tumor; ameloblastic odontosarcoma; malignant ameloblastoma; ameloblastic fibrosarcoma; malignant pinealoma; chordoma; malignant glioma; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; malignant meningioma; neurofibrosarcoma; malignant neurilemmoma; malignant granular cell tumor; malignant lymphoma; Hodgkin's disease; Hodgkin's lymphoma; paragranuloma; small lymphocytic malignant lymphoma; diffuse large cell malignant lymphoma; follicular malignant lymphoma; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the cancer comprises a solid tumor. In some embodiments, the tumor is an adenocarcinoma, an adrenal tumor, an anal tumor, a bile duct tumor, a bladder tumor, a bone tumor, a blood born tumor, a brain/CNS tumor, a breast tumor, a cervical tumor, a colorectal tumor, an endometrial tumor, an esophageal tumor, an Ewing tumor, an eye tumor, a gallbladder tumor, a gastrointestinal, a kidney tumor, a laryngeal or hypopharyngeal tumor, a liver tumor, a lung tumor, a mesothelioma tumor, a multiple myeloma tumor, a muscle tumor, a nasopharyngeal tumor, a neuroblastoma, an oral tumor, an osteosarcoma, an ovarian tumor, a pancreatic tumor, a penile tumor, a pituitary tumor, a primary tumor, a prostate tumor, a retinoblastoma, a Rhabdomyosarcoma, a salivary gland tumor, a soft tissue sarcoma, a melanoma, a metastatic tumor, a basal cell carcinoma, a Merkel cell tumor, a testicular tumor, a thymus tumor, a thyroid tumor, a uterine tumor, a vaginal tumor, a vulvar tumor, or a Wilms tumor.

In certain embodiments, the cancer is colon cancer, breast cancer, lung cancer, ovarian cancer, bladder cancer, renal cancer, or cervical cancer.

Additional Methods

In certain aspects, provided herein are methods of determining whether an agent (e.g., a test agent) is an anti-cancer therapeutic agent comprising determining whether the test agent inhibits the expression or activity of a product of at least one autophagy gene or NF-κB gene (e.g., a gene listed in Table 1 or Table 2), wherein the test agent is determined to be an anti-cancer therapeutic agent if the test agent inhibits the expression or activity of a product of at least one autophagy gene or NF-κB gene (e.g., a gene listed in Table 1 or Table 2). Also provided herein are methods of determining whether an a guide RNA agent is an anti-cancer therapeutic agent comprising determining whether the a guide RNA test agent is effective to direct a Cas enzyme to cleave or bind a sequence in an autophagy gene or an NF-κB gene (e.g., a gene listed in Table 1 or Table 2), wherein the guide RNA comprises a DNA-targeting segment that targets a guide RNA target sequence within the autophagy gene or an NF-κB gene, wherein the test agent is determined to be an anti-cancer therapeutic agent if the test agent is effective to direct a Cas enzyme to cleave or bind a sequence in the gene. A test agent disclosed herein may decreases expression of products of the at least one gene disclosed herein by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100% in a population of cells.

In some embodiments, the test agent is a member of a library of test agents. The test agent may be any agent disclosed herein, including a gRNA, a TALEN or Zinc-finger endonuclease, interfering nucleic acid or a small molecule. A test agent disclosed herein may inhibit the expression or activity of a product of at least one autophagy gene or NF-κB gene by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100%. A test agent disclosed herein may inhibit the expression or activity of a product of at least one gene in Table 1 or Table 2 by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or 100%.

Also provided herein are methods of determining whether a patient is a candidate for a cancer therapy provided herein. In some aspects, expression of a product of a gene listed in Table 1 or Table 2 by a cell in the tumor in the subject indicates that the subject is a candidate for therapy. In some embodiments, the gene product is an mRNA product. In some embodiments, the gene product is a protein product. The protein product can be detected using an antibody specific for a protein product, by IHC, or by flow cytometry (e.g., FACS). A gene product (e.g., an mRNA product) may be detected by nucleic acid amplification, a nucleic acid probe, or through sequencing.

In some embodiments, provided herein are methods of targeting and killing cancer or tumor cells by first measuring the expression level of at least one autophagy gene or NF-κB gene (e.g., at least one gene listed in Table 1 or Table 2), and, if the expression level is above a determined threshold, targeting and killing the cancer or tumor cell by administering an agent(s) disclosed herein. The threshold for a gene (e.g., a gene in Table 1 or Table 2) may be determined by a number of techniques, including, but not limited to, determining the expression of a gene or gene product in diseased tissues (e.g., tumor or cancerous tissues) versus healthy tissues (e.g., tissues not associated with a tumor or cancer). The threshold for a gene (e.g., a gene in Table 1 or Table 2) may be determined by comparing the expression of a product of the gene in the cancer cells or tumor at one time point with a later time point. Healthy and diseased tissues may be taken from the subject or from different individuals. In other embodiments, the expression threshold of a gene or gene product is determined by examining the gene or gene product expression in tissues from a tissue bank or third party source. For example, if the tumor or cancer cells from diseased tissue from the subject or a third party exhibit higher expression of a product of the gene, the subject is a candidate for therapy. If the tumor or cancer cells from a later time point exhibit higher expression of a product of the gene, the subject is a candidate for therapy.

EXEMPLIFICATION

While immune checkpoint inhibitors have transformed the treatment of cancer, the molecular determinants of tumor cell sensitivity to T cell-mediated killing remain to be fully elucidated. A genome-scale CRISPR knockout screen to identify tumor cell genes/pathways that modulate killing by T cells is described herein. The screen identified tumor cell antigen presentation and TNFα signaling as requirements for killing and conversely, identified NF-κB signaling and autophagy as major protective mechanisms. Knockout of individual autophagy genes or pharmacologic inhibition of autophagy sensitized tumor cells of various lineages to killing by T cells and/or TNFα. Conversely, inhibition of mTOR signaling, which results in increased autophagic activity, protected tumor cells from T cell killing. Mechanistically, enhanced T cell/TNFα-mediated killing in the context of impaired autophagy was not attributable to defective NF-κB signaling but was associated with increased caspase-8 activation, suggesting a role for autophagy at a relatively early step in the TNFα signaling pathway. Finally, genetic inactivation of tumor cell autophagy enhanced the efficacy of T cell checkpoint inhibitors in tumor models, suggesting that autophagy is an important modulator of antitumor immunity. These findings suggest that targeting the protective NF-κB or autophagy pathways could sensitize tumors to T cell-directed immunotherapies.

In an effort to systematically uncover genes/pathways that modulate tumor cell sensitivity to T cell killing, several groups have employed pooled CRISPR/Cas9 screens. These screens have confirmed the essential roles of antigen presentation and IFNγ signaling in tumor cell killing. In addition, these screens have identified novel modulators of killing, such as the tyrosine phosphatase Ptpn2, the apelin receptor APLNR, Pbrm1, and the SWI/SNF chromatin remodeling complex. Interestingly, some of these screens also suggested an important role for tumor cell TNFα or TRAIL signaling in the T cell killing process. While successful, for the most part these screens have identified tumor cell genes that are required for killing by T cells (i.e., single guide RNAs (sgRNAs) that are enriched in surviving tumor cells).

A pooled, genome-scale CRISPR/Cas9 knockout (KO) screen that was performed under carefully optimized conditions, enabling efficient identification of tumor cell genes that limit T cell killing. In addition to demonstrating an important role for TNFα/NF-κB signaling in modulating T cell-mediated tumor cell killing, the results uncover a previously unappreciated role for autophagy in protecting tumor cells from T cell-induced apoptosis. Herein, it is shown show that autophagy limits TNFα-dependent activation of caspase 8 without modulating NF-κB pathway activity and that genetic inhibition of autophagy sensitizes tumors to T cell checkpoint inhibitors. Thus, the autophagy pathway appears to be an important modulator of immunotherapy responsiveness, suggesting the possibility that inhibition of this pathway could enhance the efficacy of T cell-directed therapies.

Identification of Tumor Cell Genes that Modulate Sensitivity to T Cell Killing

Figure 1:
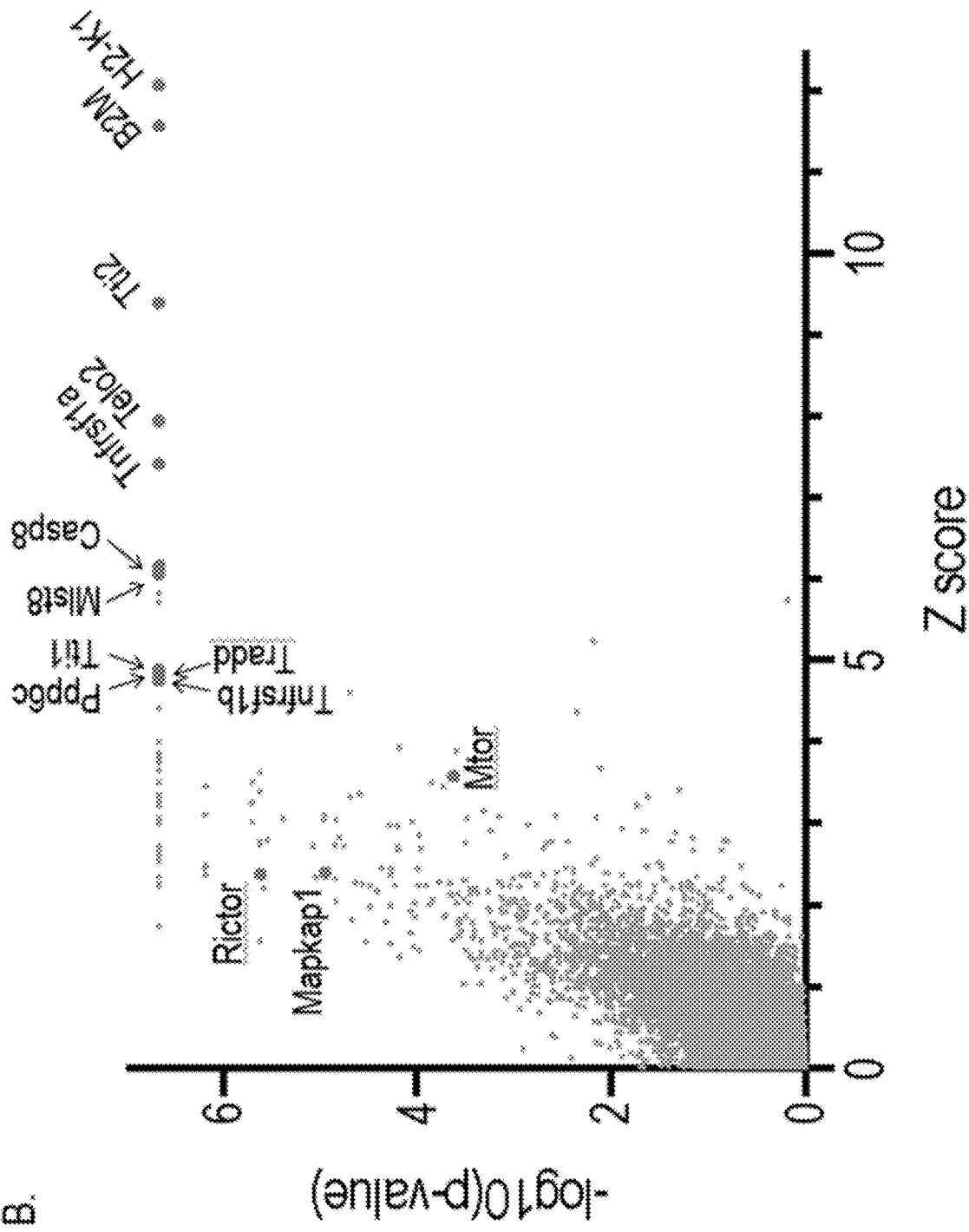
Figure 1:
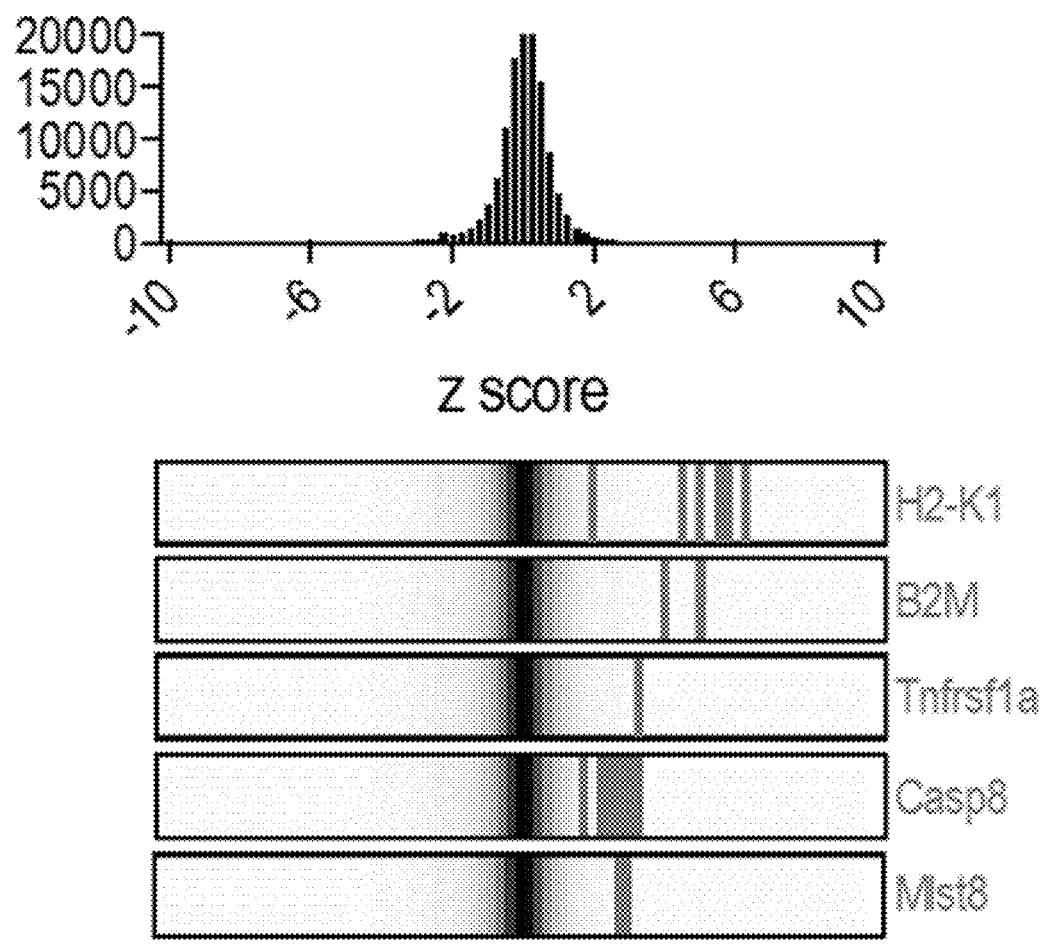
Figure 1:
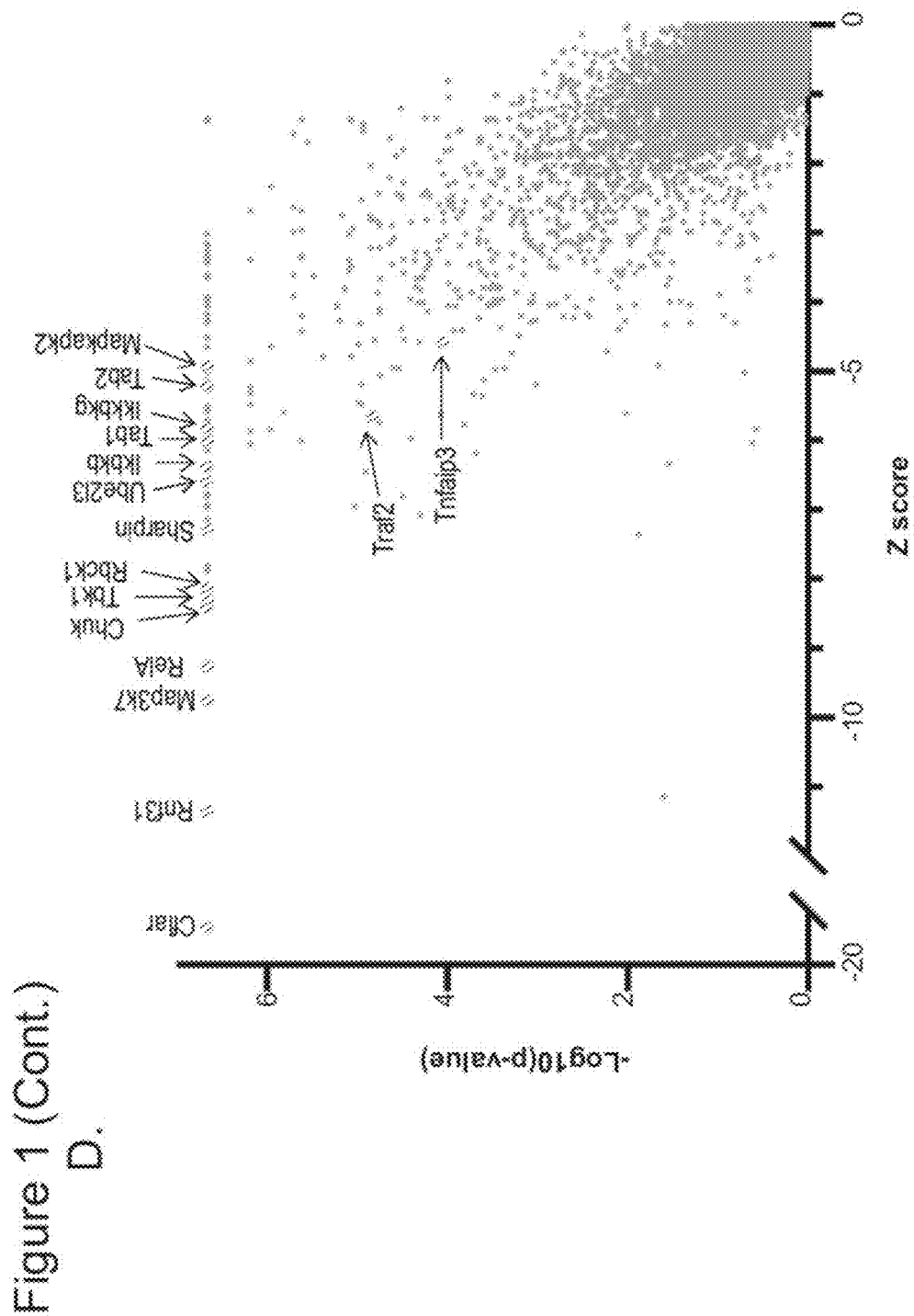
Figure 1:
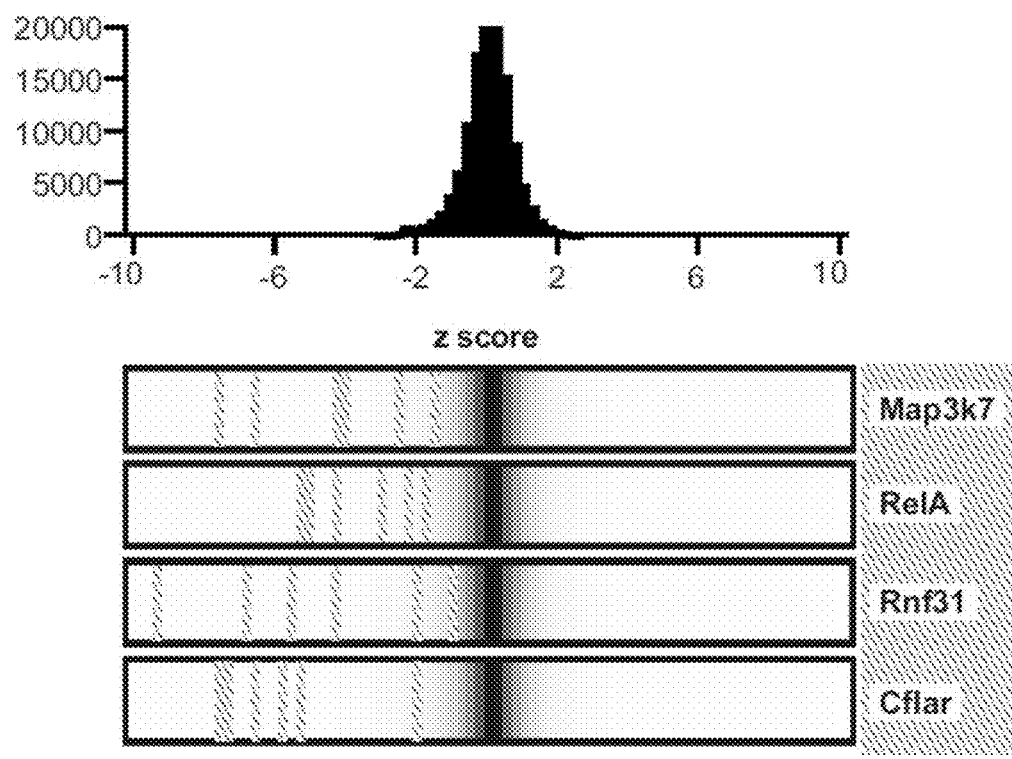
Figure 1:
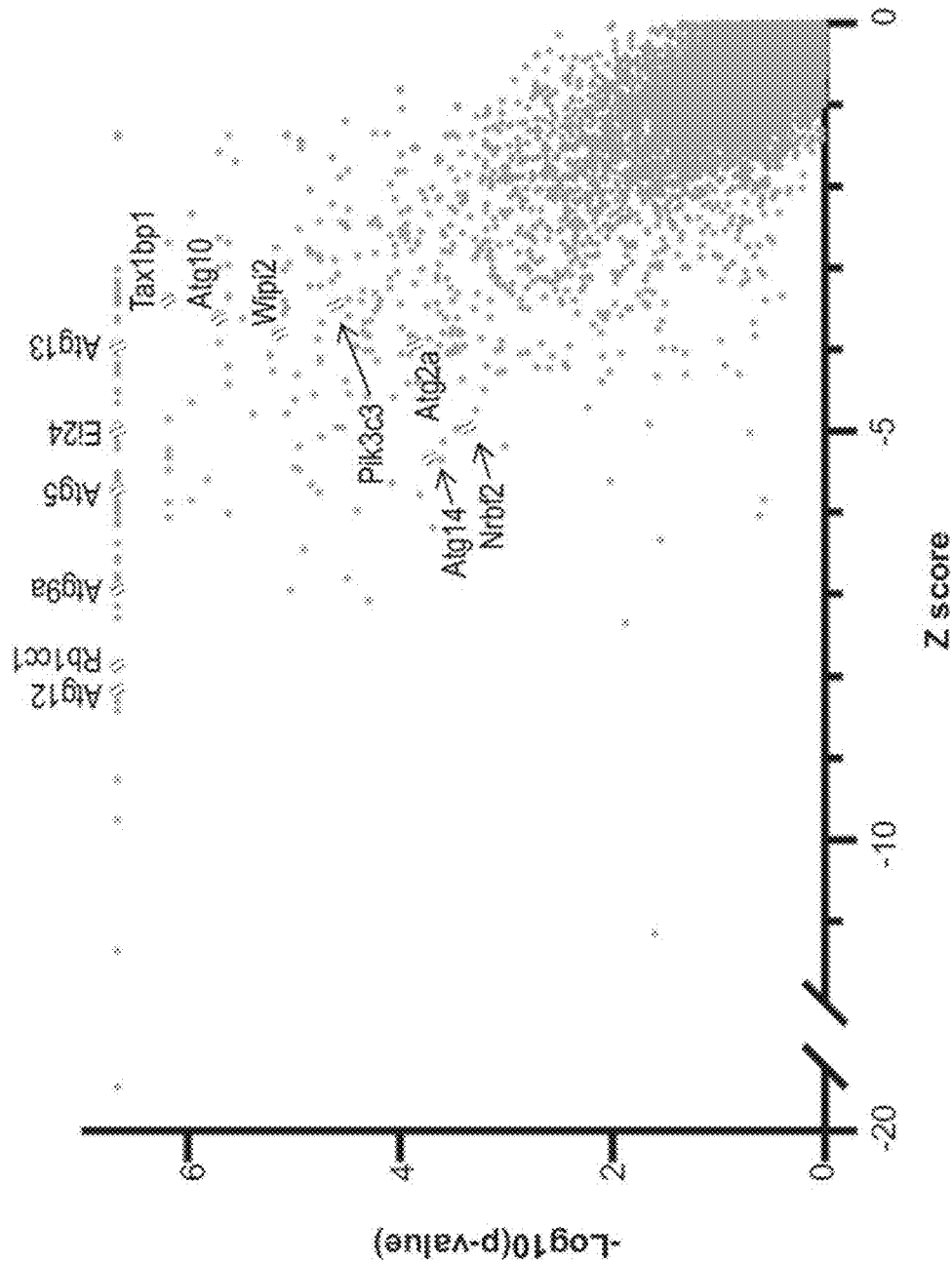
Figure 1:
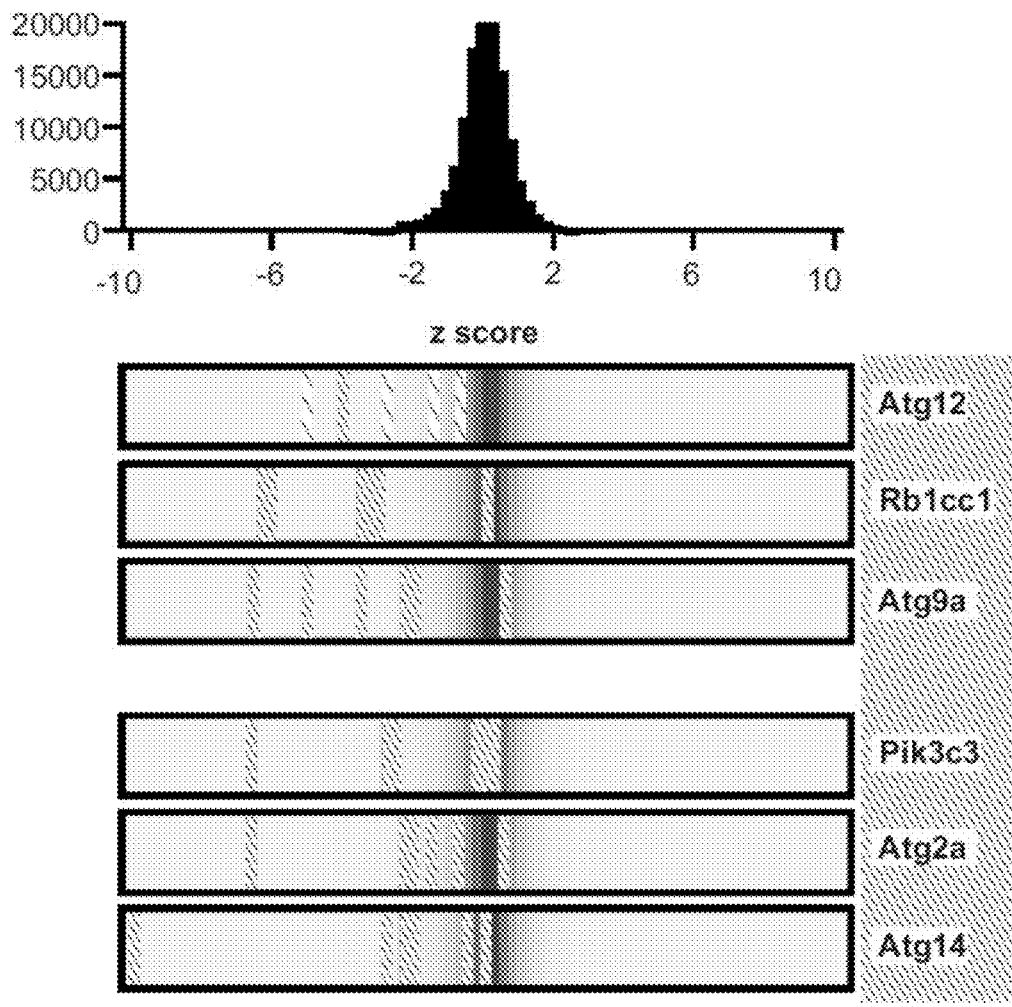
Figure 9:
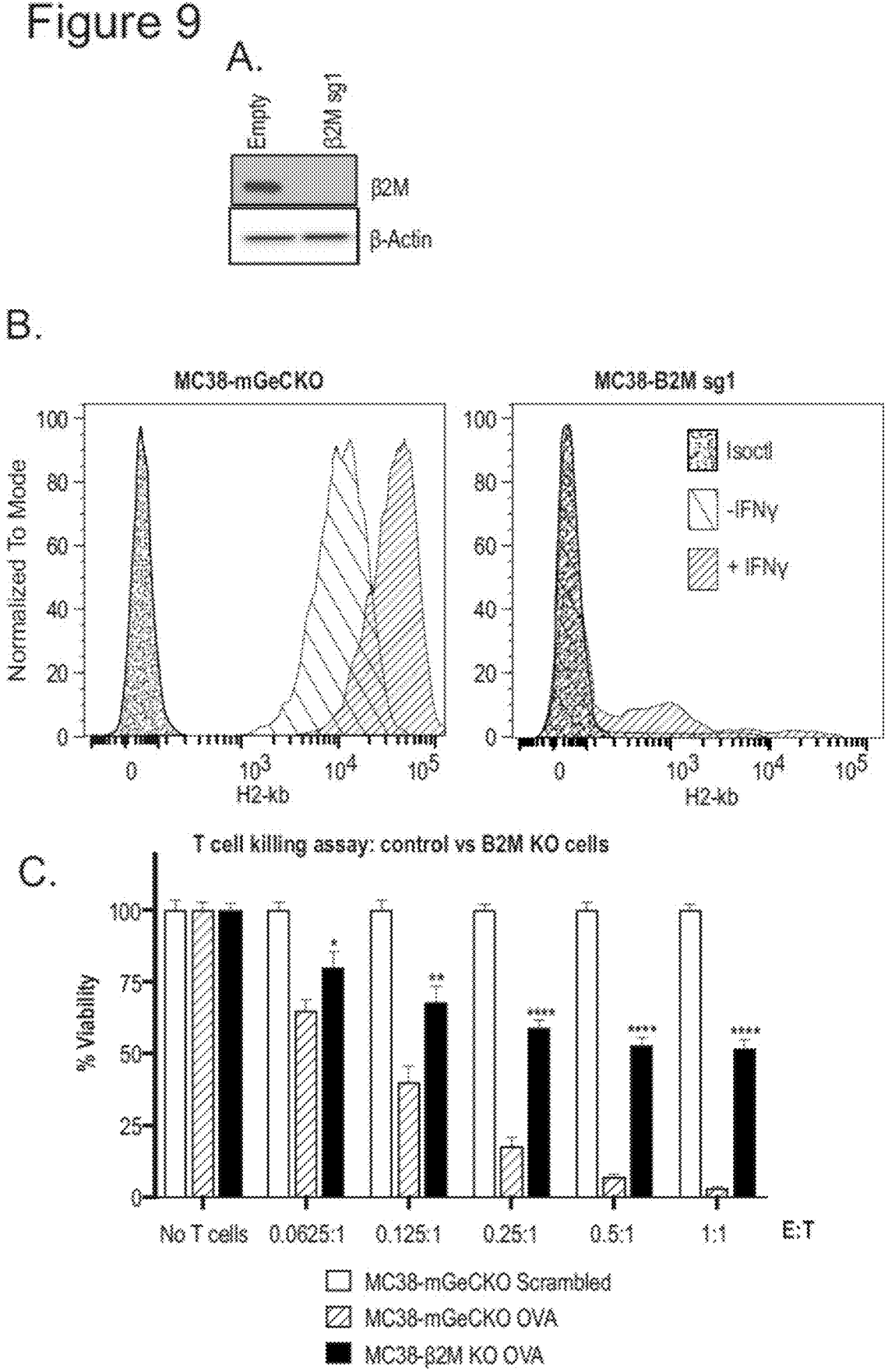
FIG. 9 has three parts, A-C, and relates to the use of B2M knockout cells used to optimize CRISPR KO screening conditions. Part A shows western blot showing B2M protein levels in MC38 cells infected with pLenti-Cas9-Blast and pLenti-guide-puro targeting B2M. Part B shows FACS analysis of H2-Kb cell surface expression in MC38 cells modified to express the mGeCKO library or b2M KO cells+/−10 ng/ml IFNg treatment for 24 hrs. Part C shows T cell killing assay of MC38-Cas9-mGeCKO cells pulsed with Ova or scrambled peptide and MC38-Cas9-B2M knockout cells pulsed with Ova peptide. CD8$^+$ T cells isolated from OT-1 mice were incubated with cells at indicated E:T ratios, viability was measured after 24 hrs.
Figure 10:
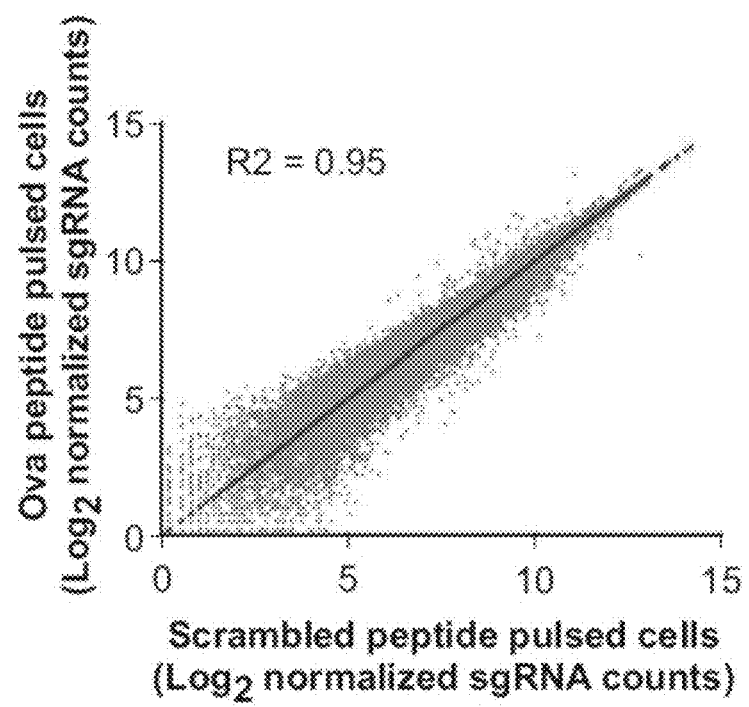
FIG. 10 shows that library representation is sufficiently maintained throughout the CRISPR KO screen, allowing detection of depleted as well as enriched sgRNAs. Log$_2$ normalized sgRNA counts in scrambled vs Ova pulsed tumor cells after T cell killing, R$^2$=0.95.
Figure 11:
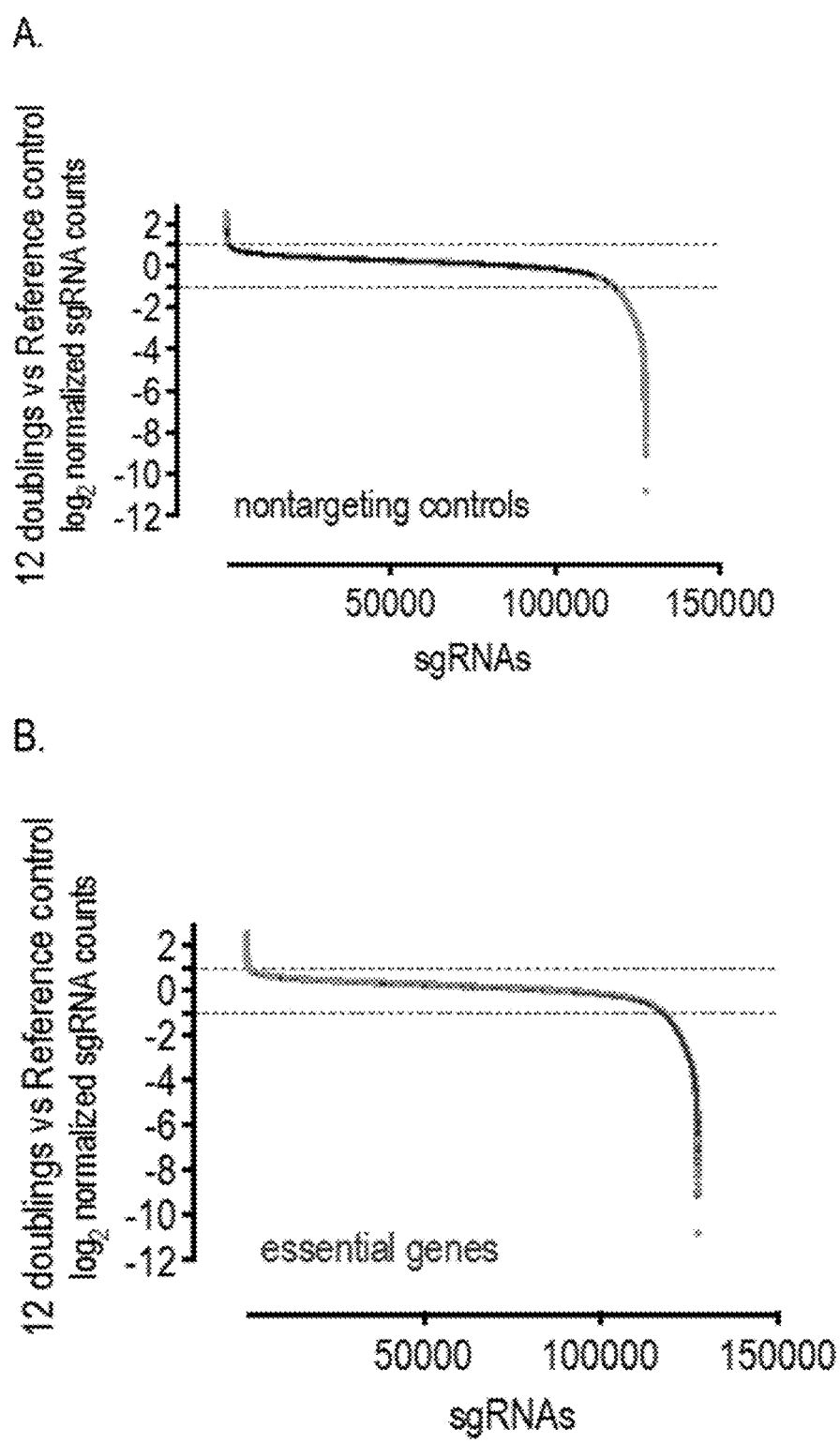
FIG. 11 has two parts, A-B, and shows CRISPR KO screen for growth modifiers in MC38 cells identifies a high proportion of core essential genes. Log 2 normalized sgRNA counts in MC38-mGeCKO cells passaged for 12 doublings compared to reference control cells (harvested immediately after selection of library-infected cells). Part A shows non-targeting sgRNAs are shown. Only 5/1000 non-targeting sgRNAs were significantly enriched or depleted more than 2-fold compared to reference controls. Part B shows sgRNAs that target core essential genes are shown in red. 96% of core essential genes (102/106) were identified as hits (defined as at least 2 sgRNAs depleted>2 fold). At least four sgRNAs were depleted for over 85% of core essential genes.

To identify genes that modulate tumor cell susceptibility to killing by cytotoxic T cells, a genome-wide CRISPR/Cas9 screen in MC38 colon adenocarcinoma cells was performed. Tumor cells transduced with a mouse single guide RNA (sgRNA) KO library were pulsed with the MHC class I-restricted Ova peptide or a scrambled control peptide and incubated with activated CD8$^+$ T cells isolated from OT-1 transgenic mice (which express a T cell receptor that recognizes the Ova peptide) (FIG. 1, Part A). Screen conditions were optimized and validated using B2m KO cells (which are protected from T cell killing) as a positive control; the goal was to achieve ~90% tumor cell kill in the screen (FIG. 9). After 24 hours exposure to T cells, viable tumor cells were harvested and sgRNA representation in Ova-pulsed versus control tumor cells was assessed by NGS. Due to a high initial library representation (~2000× coverage), sgRNA representation was maintained in the tumor cells even after killing, allowing us to efficiently detect depleted as well as enriched sgRNAs ($R^2$=0.95, Ova-versus control peptide-pulsed cells) (Table 3, FIG. 10). A parallel screen was performed with library-modified tumor cells passaged for 12 population doublings, without addition of T cells, to identify genes that modulate tumor cell growth/survival independent of T cell killing. A significant proportion of sgRNAs targeting known core essential genes were depleted in this parallel growth screen, while the representation of non-targeting sgRNAs was largely unchanged (FIG. 11), confirming the efficacy and specificity of CRISPR/Cas9-mediated gene modification in the MC38 cells.

Analysis of enriched sgRNAs identified antigen presentation and TNFα-induced apoptotic signaling as key pathways required for tumor cell killing by T cells (FIG. 1, Part B). As expected, multiple sgRNAs targeting B2m and the MHC class I molecule H2-K1 were significantly enriched, confirming that T cell killing is dependent on cell surface presentation of the Ova peptide. Recovery of all six sgRNAs targeting H2-K1 and B2m further highlights the effectiveness of CRISPR/Cas9-mediated gene modification in cells. Interestingly, multiple sgRNAs targeting Tnfrsf1a (TNF receptor 1; TNFR1), caspase-8 (required for TNFα-induced apoptosis) and Tradd (a key adaptor molecule in the TNFα signaling pathway) were also enriched (FIG. 1, Parts B and C), suggesting that T cell-derived TNFα plays an important role in tumor cell killing. Finally, sgRNAs targeting several genes in the mTOR signaling pathway were enriched (e.g., Mtor, Mlst8, Rictor, Mapkap1, Tti2, Telo2, Tti1). As shown below, inactivation of mTOR signaling protects tumor cells from T cell killing by causing increased autophagic activity.

Analysis of depleted sgRNAs identified NF-κB signaling and autophagy as two key pathways that limit tumor cell killing by T cells. Multiple sgRNAs targeting genes involved in NF-κB signaling were significantly depleted, including each member of the LUBAC (Sharpin, Rbck1 and Rnf31), TAK1 (Map3k7/Tak1, Tab1, Tab2) and Nemo complexes (Chuk, Ikbkb and Ikbkg). Furthermore, sgRNAs targeting additional NF-κB pathway or NF-κB target genes (Traf2, Tbk1, Mapkapk2, Rela, Cflar and Tnfaip3) were also depleted (FIG. 1, parts D and E). These findings are consistent with an important role for TNFα in T cell-mediated killing, since the NF-κB pathway has a well-established role in limiting TNFα-dependent apoptosis via the transcriptional induction of survival genes such as Cflar (c-Flip)).

Figure 12:
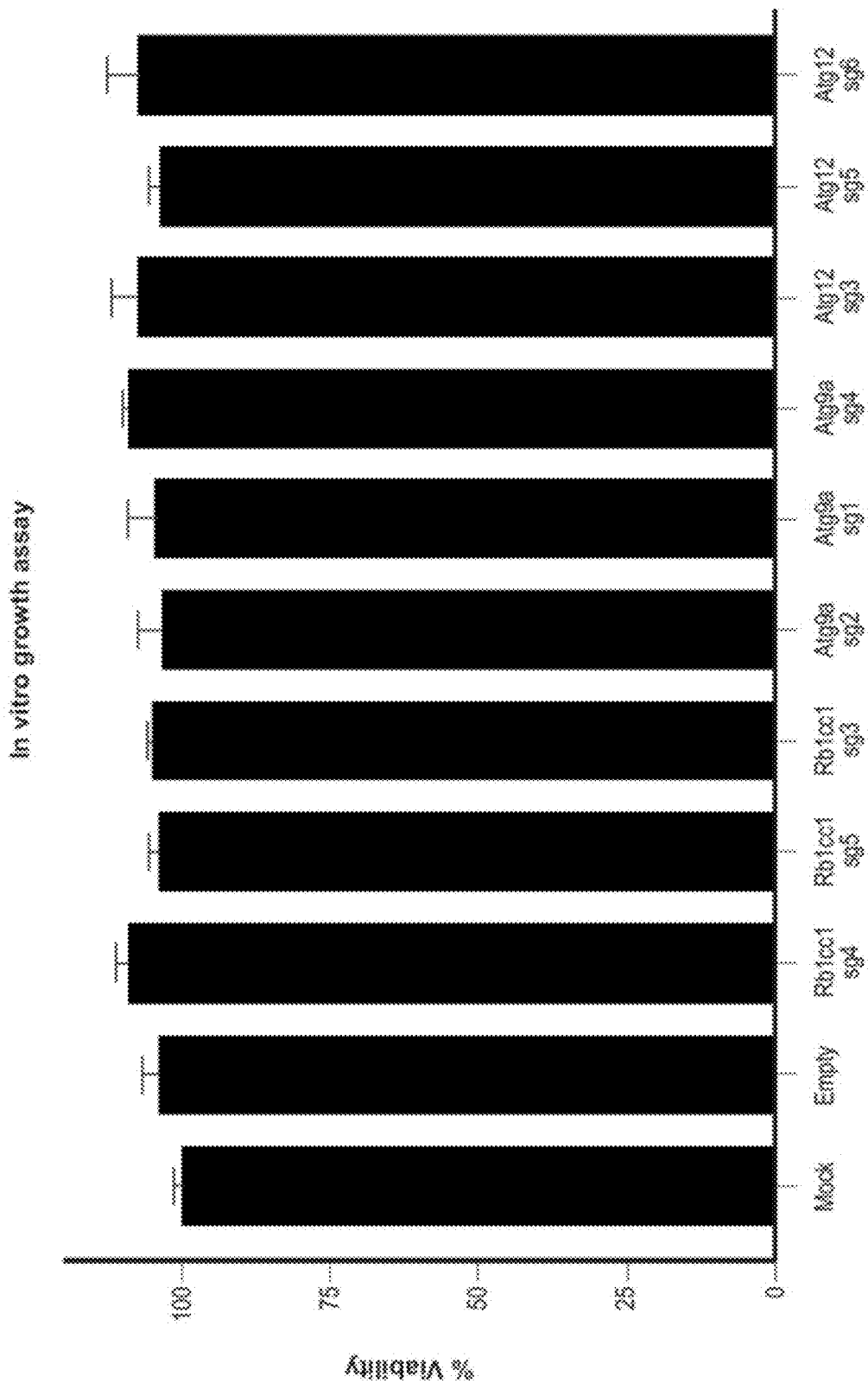
FIG. 12 shows genetic knockout of autophagy genes does not inhibit growth of MC38 cells. Viability assay after 12 population doublings in MC38 parental cells, cells expressing empty vector or cells expressing multiple sgRNAs targeting indicated autophagy genes.

Interestingly, multiple sgRNAs targeting genes in the autophagy pathway (Rb1cc1, Pik3c3, Nrbf2, Atg13, Atg14), transfer of membrane material (Atg9a, Atg2a, Tax1bp1) or autophagosome expansion (Atg5, Atg12, Atg10) were significantly depleted (FIG. 1, Parts F and G). These data indicate that autophagic activity in tumor cells has a protective role in the context of T cell killing. While autophagy is known to limit cell death in other settings (for example, nutrient deprivation), this is the first indication that it plays an important role in the context of T cell-induced tumor cell apoptosis. Importantly, sgRNAs targeting NF-κB pathway genes or autophagy genes were not depleted in the parallel cell growth screen and follow up experiments confirmed that KO of autophagy genes in MC38 cells does not impair cell growth (FIG. 12), indicating that KO of these genes decreases cell fitness specifically in the context of T cell-mediated killing. A protective role for autophagy is consistent with the observation that sgRNAs targeting multiple genes in the mTOR pathway were enriched in the screen (FIG. 1, Part B), since mTOR signaling has a well-established role in the inhibition of autophagy.

TNFα-Induced Apoptotic Signaling has an Important Role in Tumor Cell Killing by T Cells The CRISPR screen indicated a prominent role for T cell-derived TNFα in the killing of tumor cells. While killing by cytotoxic T cells is thought to result primarily from the release of perforin and granzyme from T cell granules, a role for TNFα (and other death receptor ligands) in this process has been previously proposed. While TNFα can promote cell death by either apoptosis (caspase-8 dependent) or necroptosis, several molecular checkpoints (including NF-κB activation) function to inhibit TNFα-induced cell death. Thus, the default response of most cells to TNFα is thought to be survival and induction of pro-inflammatory genes. See FIG. 2, Part A for a simplified model of TNFα/NF-κB signaling.

Figure 2:
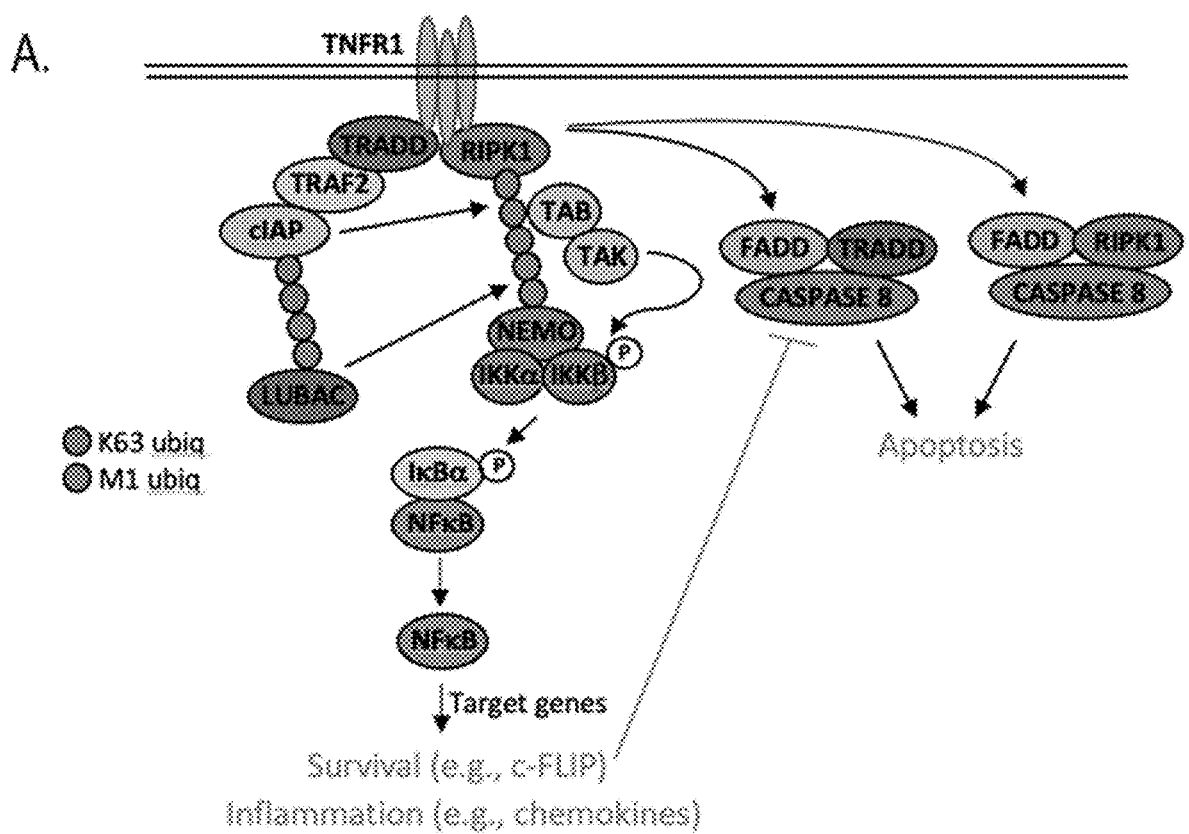
FIG. 2 has seven parts, A-G, and shows TNFα-mediated apoptosis is an important component of tumor cell killing by T cells. Part A shows a simplified model of TNFα/NF-κB signaling. Part B shows controls (MC38-mGeCKO) or B2m KO cells were pulsed with Ova peptide and incubated with T cells from OT-1 mice in the presence of 10 μg/ml TNFα blocking antibody or isotype control. Cell viability was measured after 24 hours. Bar graph shows the relative cell viability±SD (n=3) compared to cells incubated in the absence of T cells. P<0.005, *P<0.0005, ****P<0.0001, versus MC38-mGeCKO+control Ab, one-way ANOVA with Tukey's multiple comparisons test. +P<0.05, versus MC38-B2m KO+control Ab. Part C shows effects of caspase inhibition (25 μM z-VAD-FMK), Tnfrsf1a KO, Fadd KO or Ripk1 KO on viability of MC38 cells treated with 10 ng/ml TNFα for 24 hours. Bar graphs show the relative cell viability±SD (n=3). Western blots confirming target protein depletion are shown below the graphs. * indicates the Ripk1 KO used in the assay. Part D shows TNFα at the indicated concentrations was added to tumor cell lines and cell viability was measured after 24 hours, n=3. Part E shows western blots showing the levels of the indicated proteins 24 hours after addition of 10 ng/ml TNFα to each cell line. Parts F and G show western blots showing the levels of the indicated proteins in MC38 or B16F10 cells following treatment with 10 ng/ml TNFα for the indicated times.
Figure 2:
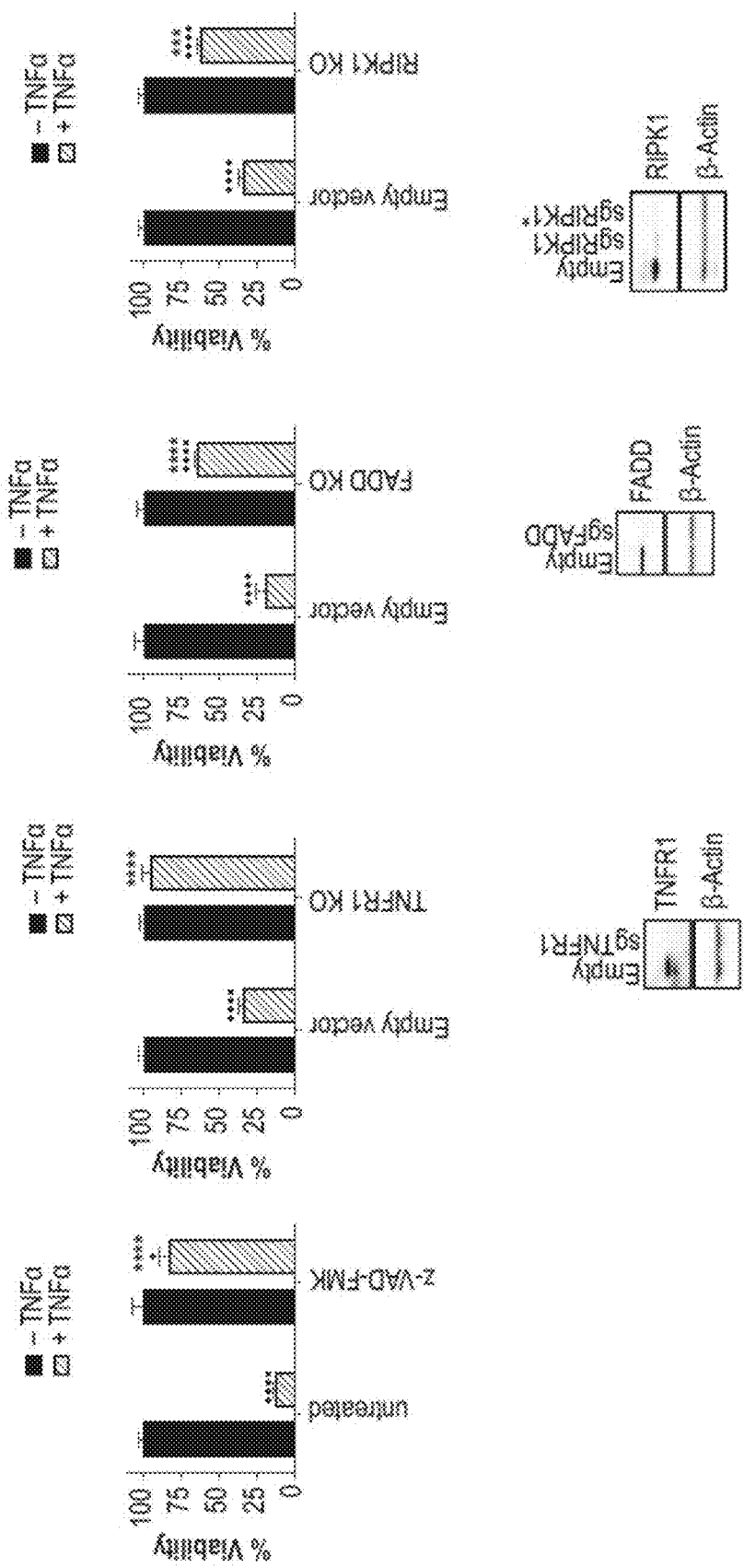
Figure 2:
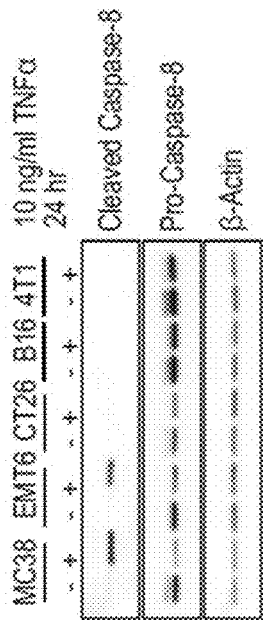
Figure 2:
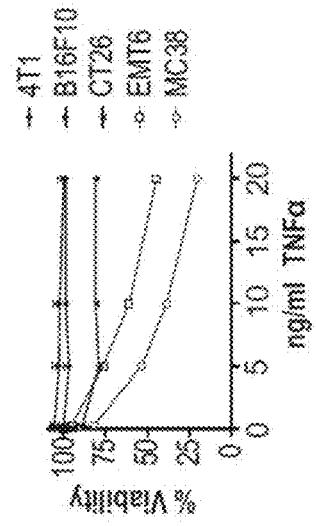
Figure 2:
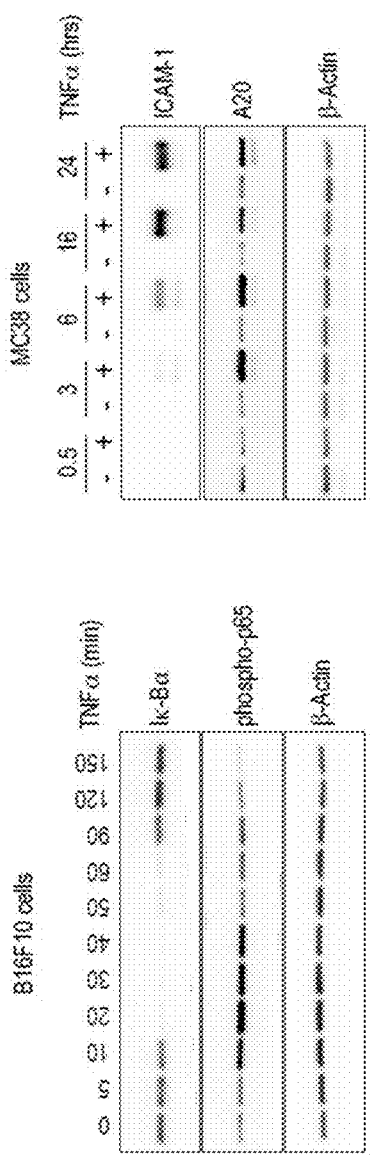
Figure 2:
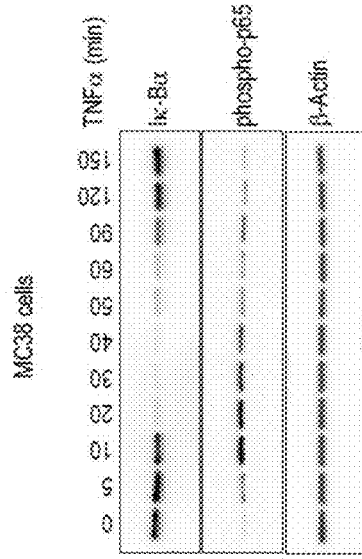
Figure 13:
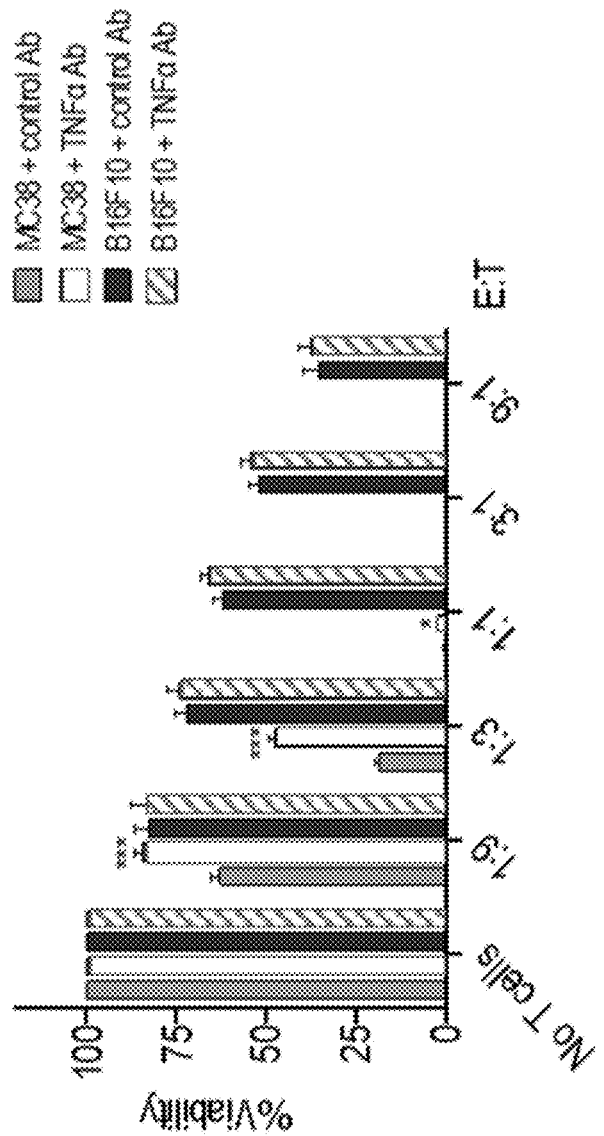
FIG. 13 shows the cytotoxic function of pre-activated T cells is not limited by TNFα blockade. MC38 (TNFα sensitive) or B16F10 (TNFα resistant) cells were pulsed with Ova peptide and incubated with T cells from OT-1 mice at the indicated E:T ratios, in the presence of 20 µg/ml TNFα blocking antibody or isotype control antibody. Cell viability was measured after 24 hours. Bar graph shows the relative cell viability±SD (n=3) compared to tumor cells incubated without T cells. *P<0.05, ***P<0.0005, versus MC38 cells with control antibody, one-way ANOVA with Tukey's multiple comparisons test.

As shown in FIG. 2, Part B, addition of a TNFα blocking antibody to the T cell killing assay significantly decreased MC38 cell death (to the same extent as CRISPR/Cas9-mediated inactivation of B2m), confirming the role of TNFα signaling. It is important to note that the effect of TNFα blockade on tumor cell killing in the assays (which use pre-activated T cells) is not attributable to inhibition of T cell function, since TNFα blockade does not limit killing of TNFα-insensitive tumor cells (FIG. 13). Consistent with a significant contribution of TNFα to T cell killing of MC38 cells, soluble TNFα promoted MC38 cell death via an apoptotic mechanism (i.e., killing was blocked by the caspase inhibitor z-VAD-FMK) (FIG. 2, Part C). Furthermore, generation of KO cell lines using CRISPR/Cas9 confirmed that TNFα-mediated killing of MC38 cells is completely dependent on TNFR1 and partially dependent on FADD (an adapter protein important for assembly of caspase-8 activation complexes) and RIPK1 (a kinase that interacts with caspase-8 to promote apoptosis (FIG. 2, Part C).

Figure 14:
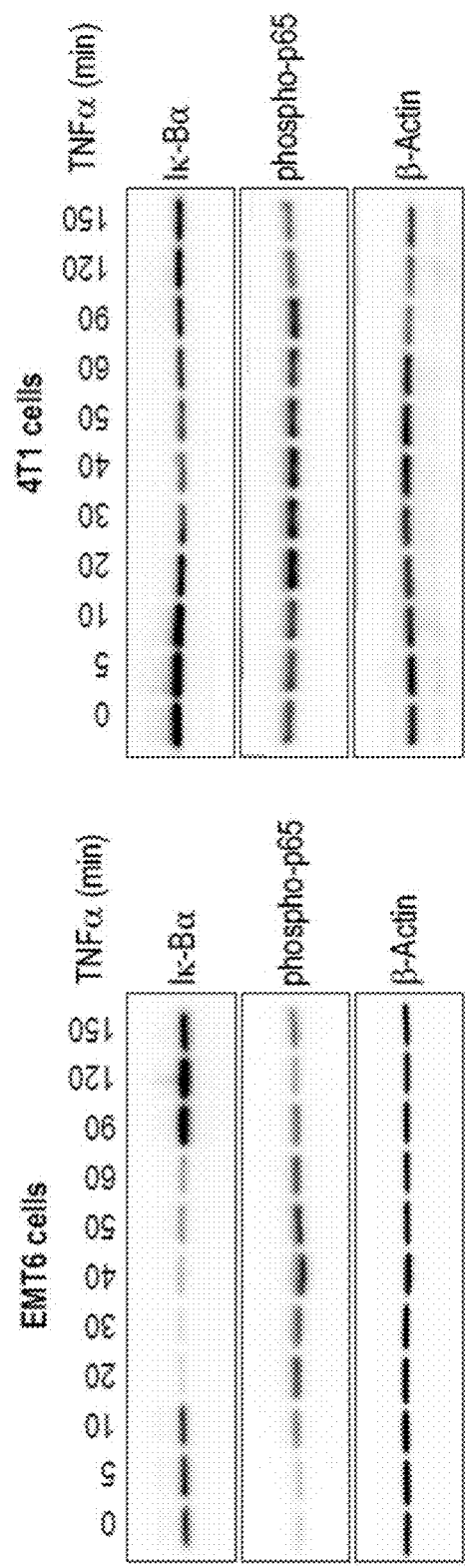
FIG. 14 shows that the NF-κB signaling pathway is active in cell lines resistant to TNFα-mediated killing. Western blots showing the levels of the indicated proteins in EMT6 or 4T1 cells after treatment with 10 ng/ml TNFα for the indicated times.

The ability of TNFα to induce caspase-8 activation and apoptosis in a panel of tumor cell lines was assessed and it was found that while the majority of these cell lines (CT26, B16F10, 4T1) were not killed by TNFα, EMT6 cells (along with MC38) exhibited TNFα-induced caspase-8 activation and apoptosis (FIG. 2, Part D and E). (See FIG. 22 for examples of human cancer cell lines that are sensitive to killing by TNFα.) As noted above, NF-κB signaling is thought to play a prominent role in limiting TNFα-dependent apoptosis. However, it was found that no apparent differences in NF-κB activation in TNFα-sensitive versus resistant cell lines. TNFα-sensitive MC38 and EMT6 cells exhibited efficient degradation of Iκ-Bα (which inhibits NF-κB by sequestering it in the cytoplasm) and phosphorylation of the NF-κB subunit p65/Rela, similar to that observed in TNFα-resistant B16F10 and 4T1 cells (FIG. 2, Part F, FIG. 14). In addition, MC38 cells exhibited strong TNFα-induced expression of two NF-κB target genes, A20 and ICAM-1 (FIG. 2, Part G). Therefore, while the NF-κB pathway clearly limits TNFα-dependent, sensitivity to TNFα-induced killing can apparently result from factors other than defective NF-κB activation.

NF-κB Signaling Limits Tumor Cell Killing by T Cells and TNFα

Figure 3:
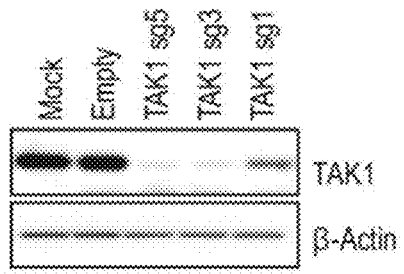
FIG. 3 has seven parts, A-G, and shows NF-κB signaling limits tumor cell killing by T cells. Part A shows western blots showing Map3k7 (aka Tak1) and β-actin protein levels in MC38 parental cells (mock), MC38-Cas9 cells transduced with an empty vector or cells expressing Map3k7-targeted sgRNAs (sg5 and sg3 were depleted most significantly in the screen; sg1 was depleted least significantly). Part B shows control or Map3k7 KO cells were pulsed with Ova peptide and incubated with OT-1 T cells at the indicated E:T ratios for 24 hours. Bar graph shows the relative cell viability±SD (n=3) compared to cells incubated in the absence of T cells. P<0.005, *P<0.0005, ****P<0.0001, versus parental MC38 cells, one-way ANOVA with Tukey's multiple comparisons test. ++P<0.005, ++++P<0.0001, versus Map3k7 sg5. Part C shows T cell killing of the indicated cell lines was performed in the presence of 20 μg/ml TNFα blocking antibody. Part D shows cells were treated with the indicated concentrations of TNFα and cell viability was measured after 24 hours, n=3. Part E shows western blots showing the levels of the indicated proteins 2 hours after treatment with 10 ng/ml TNFα. Parts F and G shows cells were treated with the indicated amounts of doxorubicin or paclitaxel and cell viability was measured after 24 hours, n=3.
Figure 3:
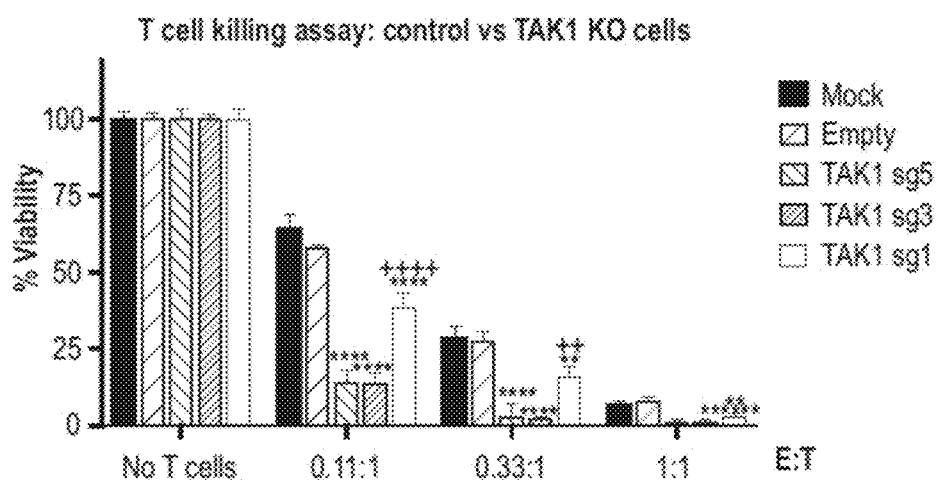
Figure 3:
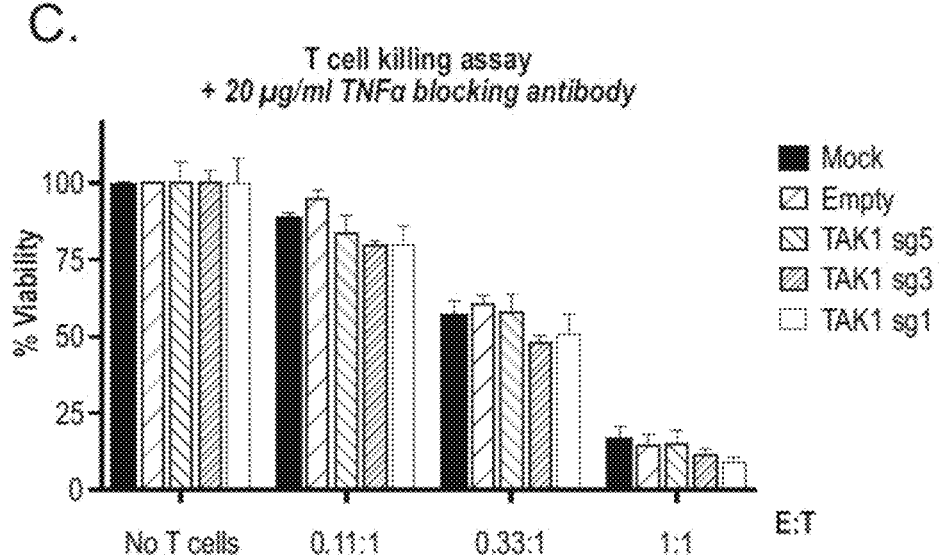
Figure 3:
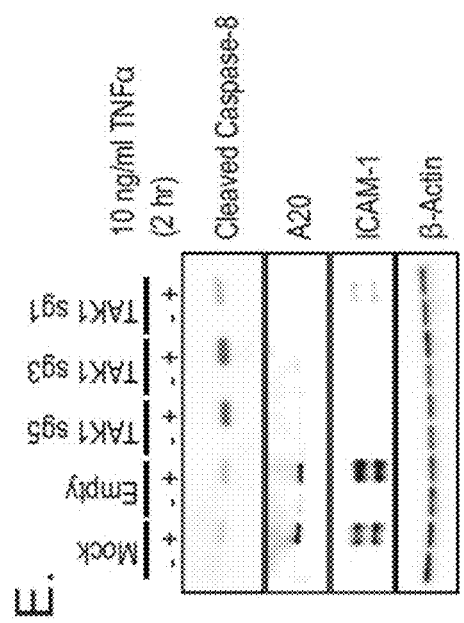
Figure 3:
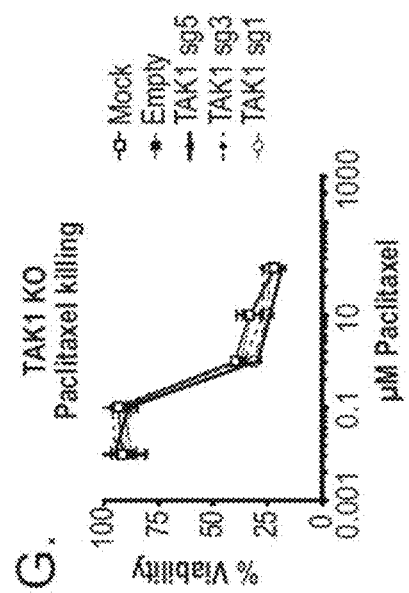
Figure 3:
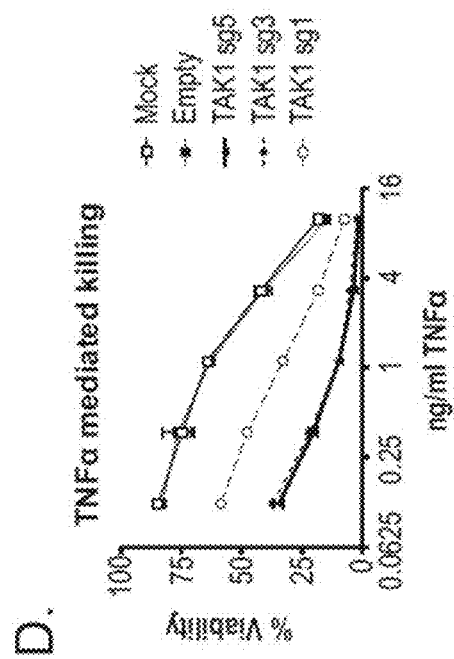
Figure 3:
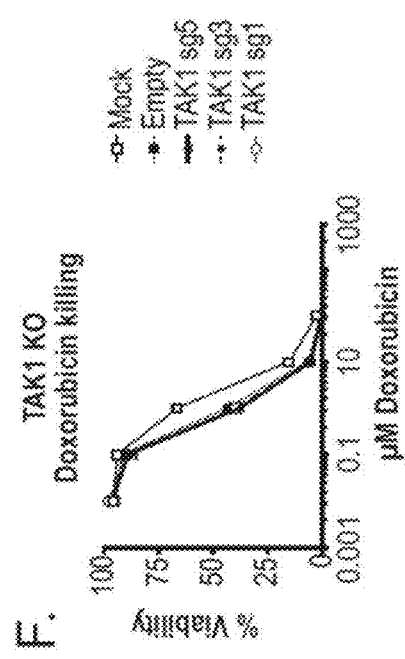

To confirm screen data indicating a role for the NF-κB pathway in limiting killing of MC38 cells by T cells, three critical NF-κB pathway genes (Map3k7/Tak1, Rbck1 and Rela) were inactivated using sgRNAs that were depleted in the screen. Inactivation of Map3k7 by multiple sgRNAs sensitized MC38 cells to T cell killing and the extent of Map3k7 protein depletion by different sgRNAs correlated with the degree of sensitization, indicating that these effects are on target (FIG. 3, Parts A and B). Map3k7 KO significantly inhibited the induction of the NF-κB target genes A20 and ICAM-1 by TNFα, confirming that Map3k7 KO disables the NF-κB pathway (FIG. 3, Part E). Similar effects on T cell killing were observed upon knockout of Rbck1 (FIG. 15) and the NF-κB subunit p65 (Rela) (FIG. 16), further validating the protective effect of NF-κB signaling.

Figure 15:
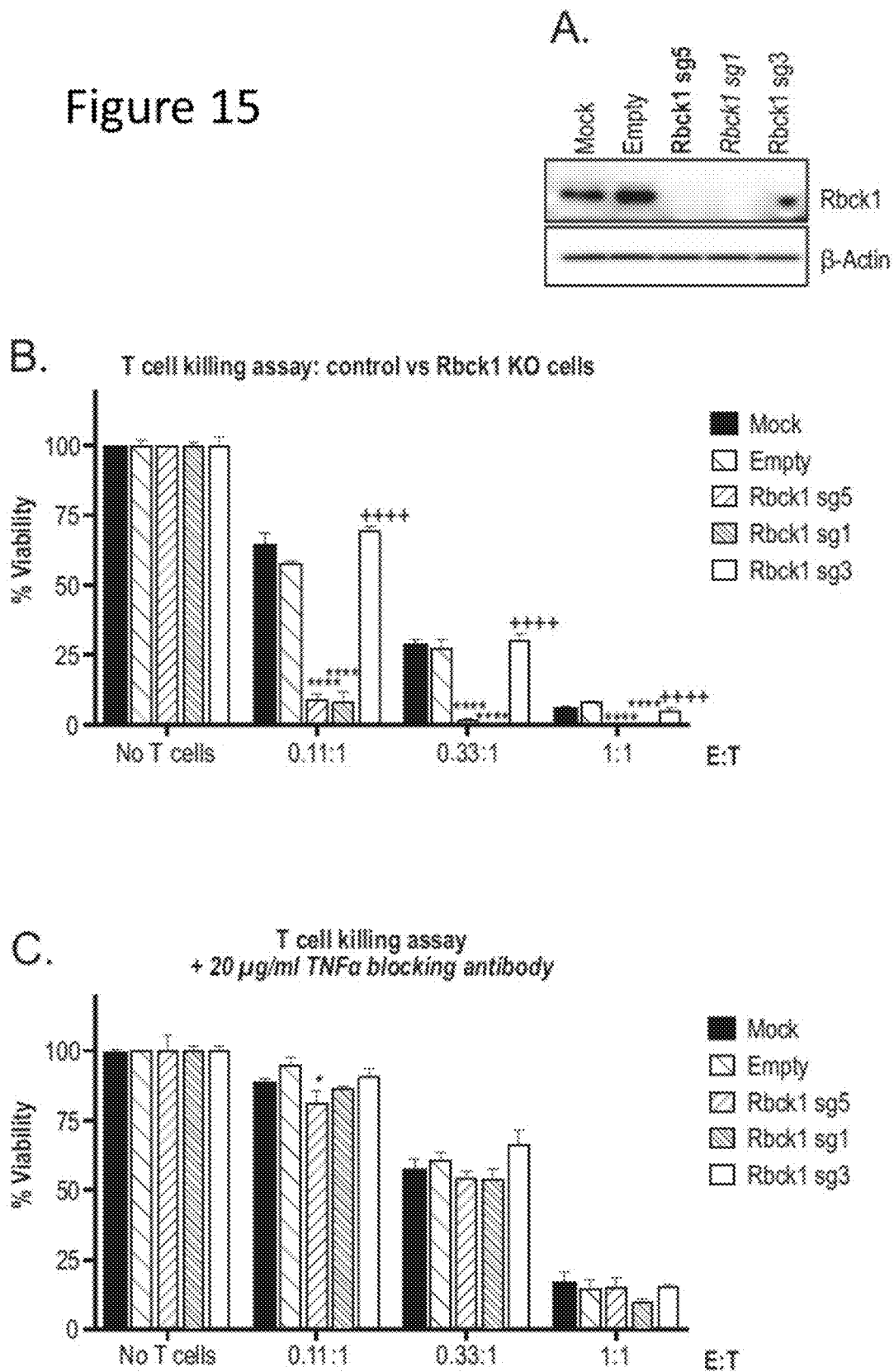
FIG. 15 has seven parts, Parts A-G, and shows Rbck1 KO increases tumor cell killing by T cells. Part A shows western blots showing Rbck1 and β-actin levels in MC38 parental cells (mock), MC38-Cas9 cells transduced with empty vector or cells expressing Rbck1-targeted sgRNAs (sg5 and sg1 were depleted most significantly in the screen; sg3 was depleted least significantly). Part B shows control or Rbck1 KO cells were pulsed with Ova peptide and incubated with OT-1 T cells at the indicated E:T ratios for 24 hours. Bar graph shows the relative cell viability±SD (n=3) compared to cells incubated in the absence of T cells. ****$P<0.0001$, versus parental MC38 cells, one-way ANOVA with Tukey's multiple comparisons test. ++++$P<0.0001$, versus Rbck1 sg5. Part C shows T cell killing of the indicated cell lines was performed in the presence of 20 µg/ml TNFα blocking antibody. *$P<0.05$, versus parental MC38 cells. Part D shows cells were treated with the indicated concentrations of TNFα and cell viability was measured after 24 hours, n=3. Part E shows western blots showing the levels of the indicated proteins 2 hours after treatment with 10 ng/ml TNFα. Part F And G shows cells were treated with the indicated amounts of doxorubicin or paclitaxel and cell viability was measured after 24 hours, n=3.
Figure 15:
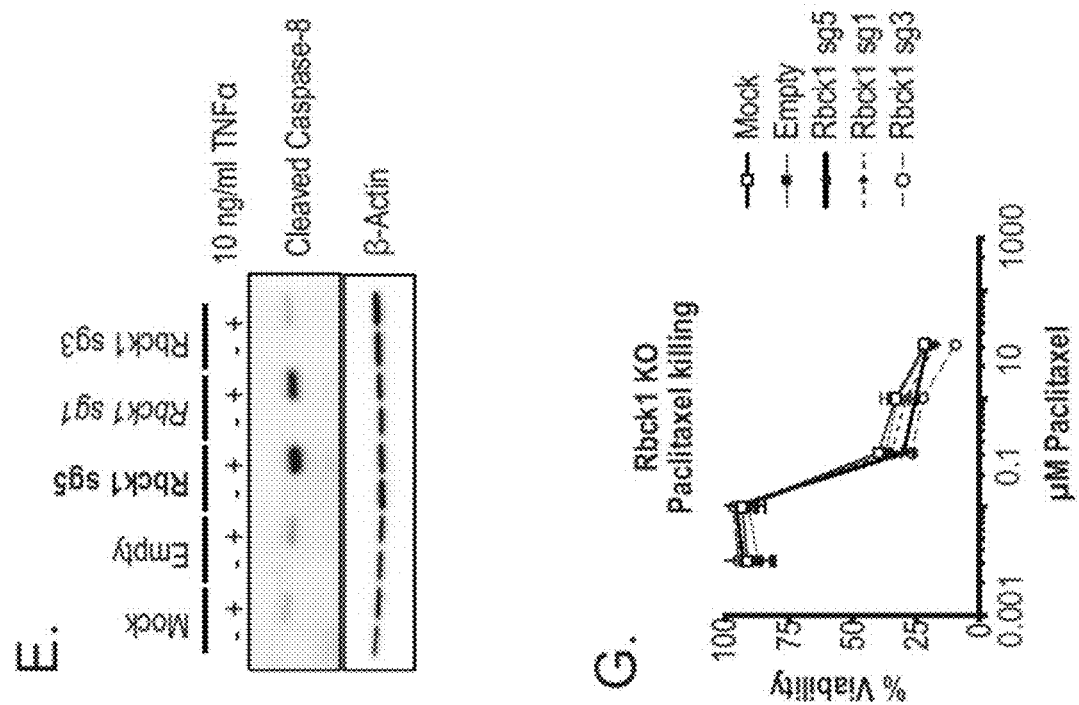
Figure 15:
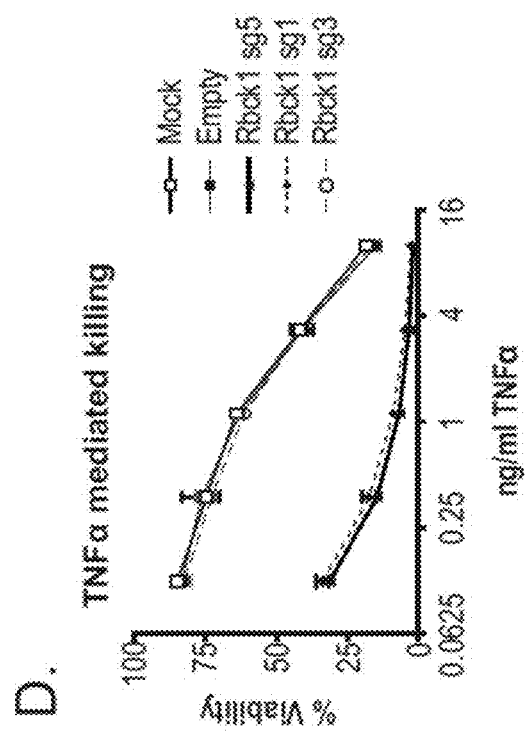
Figure 15:
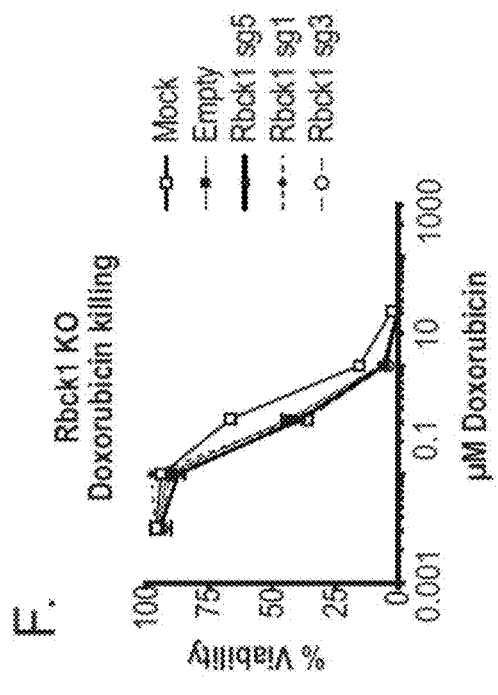
Figure 16:
FIG. 16 has seven parts, A-G, and shows Rela KO increases tumor cell killing by T cells. Part A shows that western blots showing Rela and β-actin levels in MC38 parental cells (mock), MC38-Cas9 cells transduced with empty vector or cells expressing Rela-targeted sgRNAs (sg2 and sg3 were depleted most significantly in the screen; sg6 was depleted least significantly). Part B shows that control or Rela KO cells were pulsed with Ova peptide and incubated with OT-1 T cells at the indicated E:T ratios for 24 hours. Bar graph shows the relative cell viability±SD (n=3) compared to cells incubated in the absence of T cells. $P<0.005$, **$P<0.0001$, versus parental MC38 cells, one-way ANOVA with Tukey's multiple comparisons test. ++$P<0.005$, +++$P<0.0005$, versus Rela sg2. Part C shows T cell killing of the indicated cell lines was performed in the presence of 20 µg/ml TNFα blocking antibody. Part D shows cells were treated with the indicated concentrations of TNFα and cell viability was measured after 24 hours, n=3. Part E shows western blots showing the levels of the indicated proteins 2 hours after treatment with 10 ng/ml TNFα. Part F and G shows cells were treated with the indicated amounts of doxorubicin or paclitaxel and cell viability was measured after 24 hours, n=3.
Figure 16:
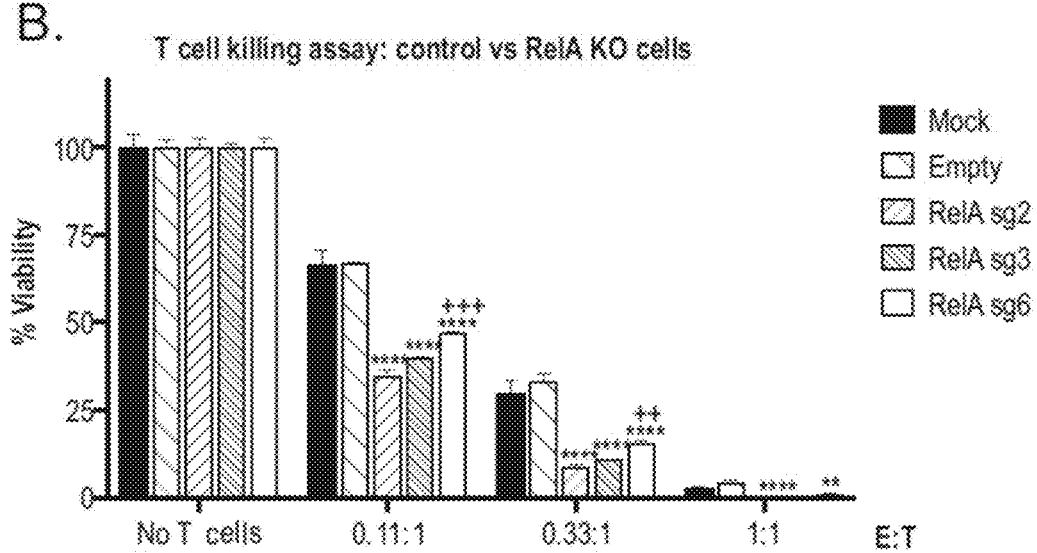
Figure 16:
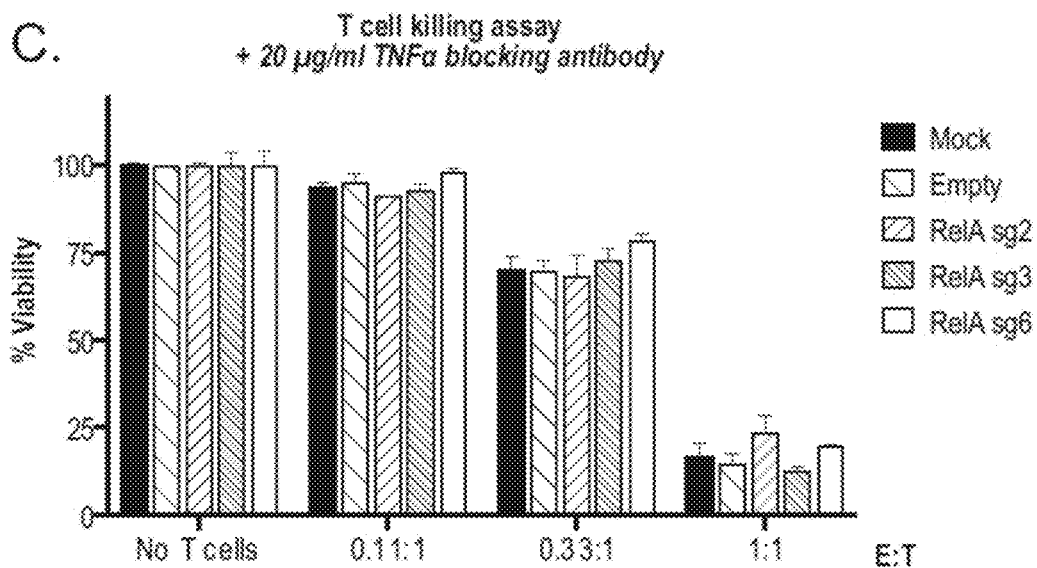
Figure 16:
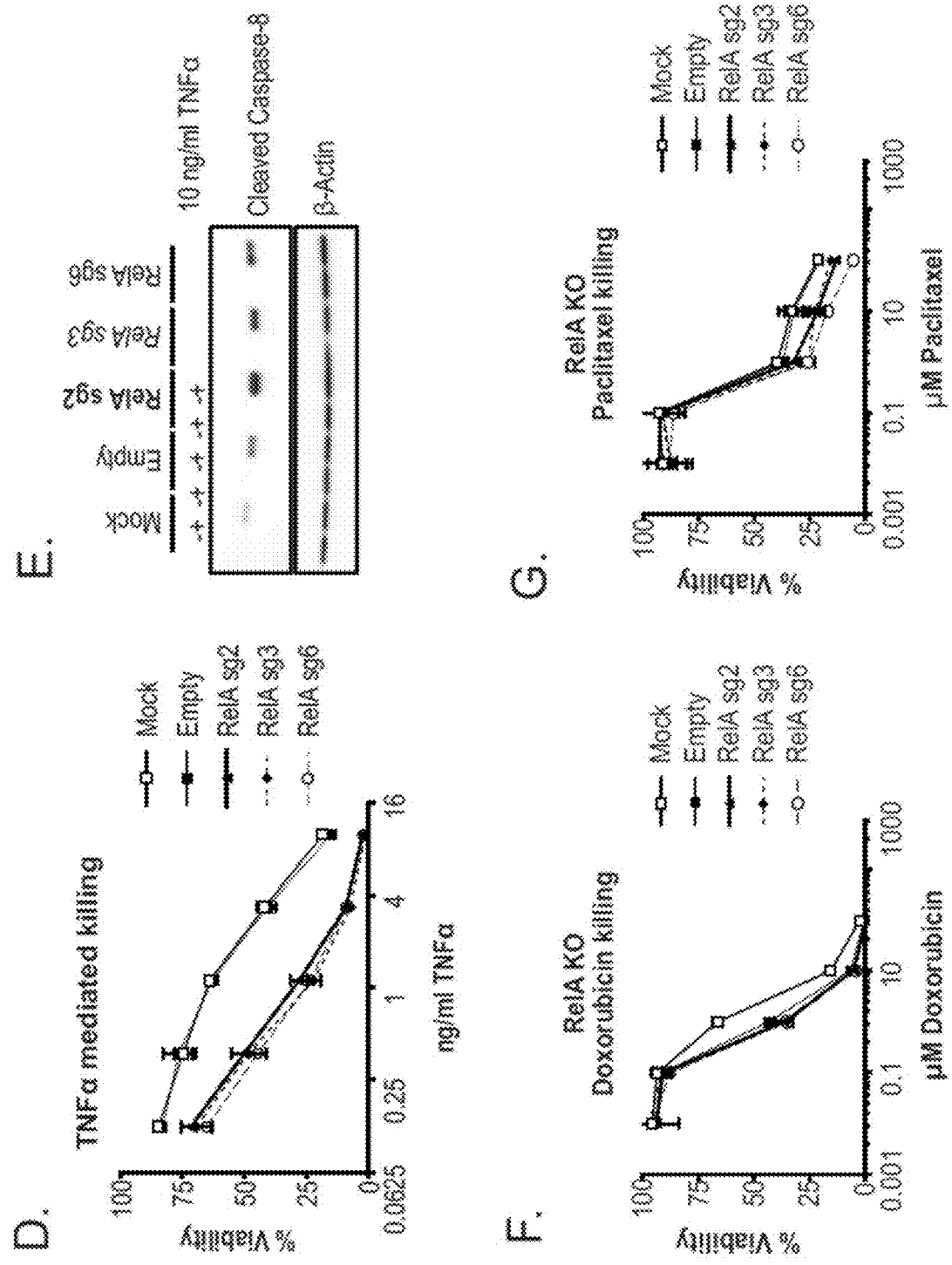

Importantly, in the presence of saturating amounts of TNFα blocking antibody, Map3k7 KO (as well as Rbck1 and Rela KO) no longer enhanced killing of MC38 cells by T cells (FIG. 3, Part C, and FIGS. 15 and 16), indicating that the protective effect of the NF-κB pathway reflects inhibition of TNFα-mediated apoptosis (rather than of perforin/granzyme-mediated killing). Consistent with this hypothesis, KO of Map3k7, Rbck1 and Rela significantly increased TNFα-induced caspase-8 activation and cell death (FIG. 3, Part D and E, FIGS. 15 and 16). In contrast to the effect on TNFα-dependent apoptosis, Map3k7 KO (as well as Rbck1 and Rela KO) had no effect on killing of MC38 cells by the chemotherapeutics doxorubicin and paclitaxel, indicating that the NF-κB pathway does not broadly protect these cells from any apoptosis-inducing stimulus (FIG. 3, Part F, and FIGS. 15 and 16).

Autophagy Limits Tumor Cell Killing by T Cells and TNFα

Figure 4:
FIG. 4 has six parts, A-F, and shows autophagy limits tumor cell killing by T cells. Part A shows western blots showing Rb1cc1 and β-actin protein levels in MC38 parental cells (mock), MC38-Cas9 cells transduced with an empty vector or cells expressing Rb1cc1-targeted sgRNAs (sg4 and sg5 were depleted most significantly in the screen; sg3 was depleted least significantly). Part B shows control or Rb1cc1 KO cells were pulsed with Ova peptide and incubated with OT-1 T cells at the indicated E:T ratios for 24 hours. Bar graph shows the relative cell viability±SD (n=3) compared to cells incubated in the absence of T cells. P<0.005, **P<0.0001, versus parental MC38 cells, one-way ANOVA with Tukey's multiple comparisons test. ++++ P<0.0001, versus Rb1cc1 sg4. Part C shows that T cell killing of the indicated cell lines was performed in the presence of 20 μg/ml TNFα blocking antibody. *P<0.05, ***P<0.0005, versus parental MC38 cells. Part D shows cells were treated with the indicated concentrations of TNFα and cell viability was measured after 24 hours. Parts E and F shows cells were treated with the indicated amounts of doxorubicin or paclitaxel and cell viability was measured after 24 hours, n=3.
Figure 4:
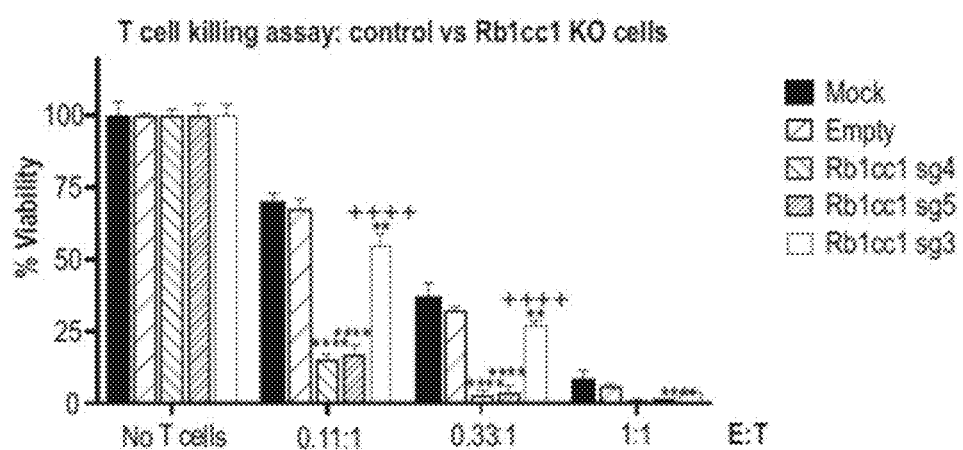
Figure 4:
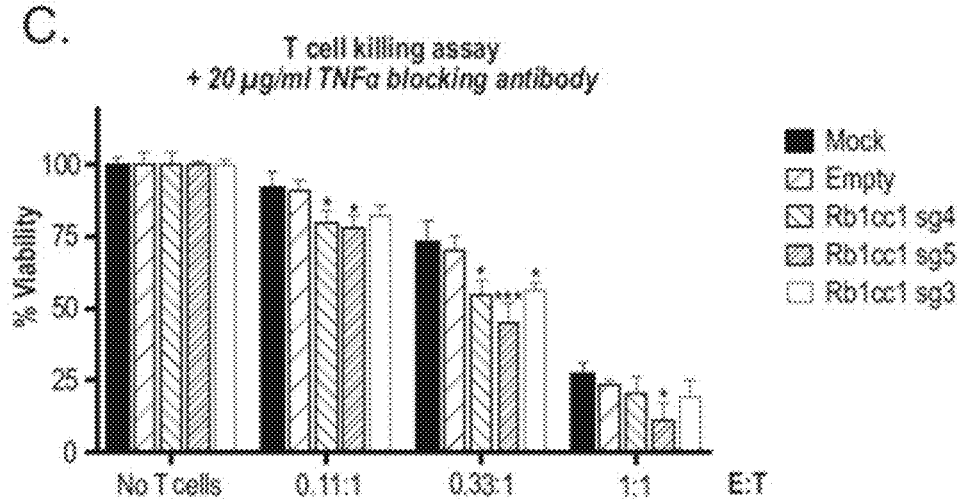
Figure 4:
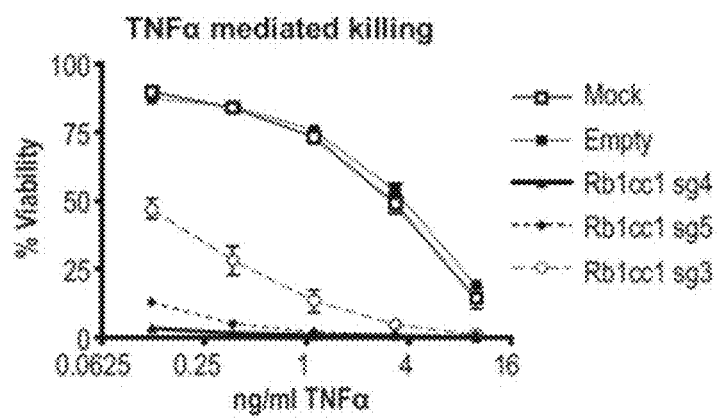
Figure 4:
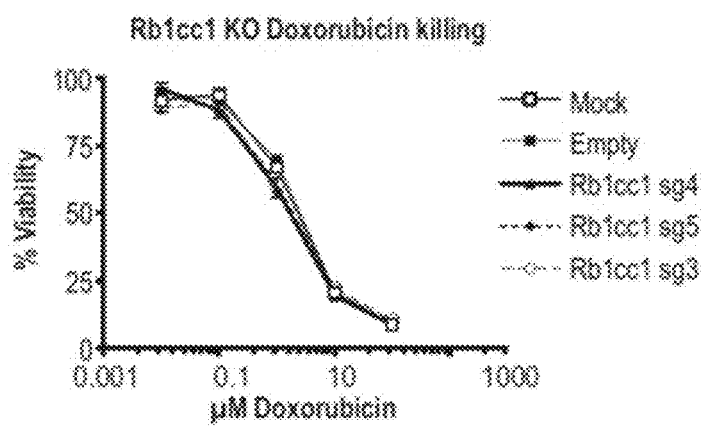
Figure 4:
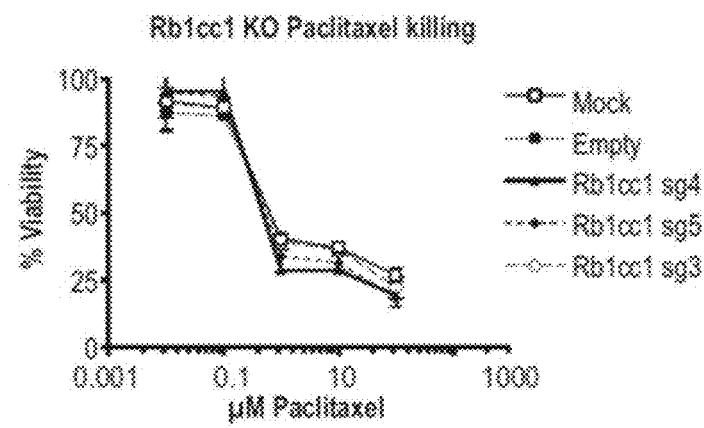
Figure 17:
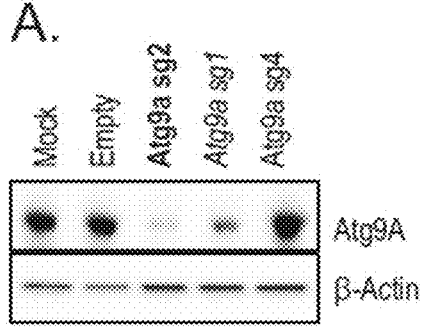
FIG. 17 has seven parts, A-G, and shows Atg9a KO increases tumor cell killing by T cells. Part A shows western blots showing Atg9a and β-actin levels in MC38 parental cells (mock), MC38-Cas9 cells transduced with empty vector or cells expressing Atg9a-targeted sgRNAs (sg2 and sg1 were depleted most significantly in the screen; sg4 was depleted least significantly). Part B shows control or Atg9a KO cells were pulsed with Ova peptide and incubated with OT-1 T cells at the indicated E:T ratios for 24 hours. Bar graph shows the relative cell viability±SD (n=3) compared to cells incubated in the absence of T cells. $P<0.005$, *$P<0.0005$, ****$P<0.0001$, versus parental MC38 cells, one-way ANOVA with Tukey's multiple comparisons test. +$P<0.05$, ++++$P<0.0001$, versus Atg9a sg2. Part C shows T cell killing of the indicated cell lines was performed in the presence of 20 µg/ml TNFα blocking antibody. *$P<0.05$, $P<0.005$, *$P<0.0005$, versus parental MC38 cells. +$P<0.05$, versus Atg9a sg2. Part D shows cells were treated with the indicated concentrations of TNFα and cell viability was measured after 24 hours, n=3. Part E shows western blots showing the levels of the indicated proteins 8 hours after treatment with 10 ng/ml TNFα. Part F shows cells were treated with the indicated amounts of doxorubicin or paclitaxel and cell viability was measured after 24 hours, n=3.
Figure 17:
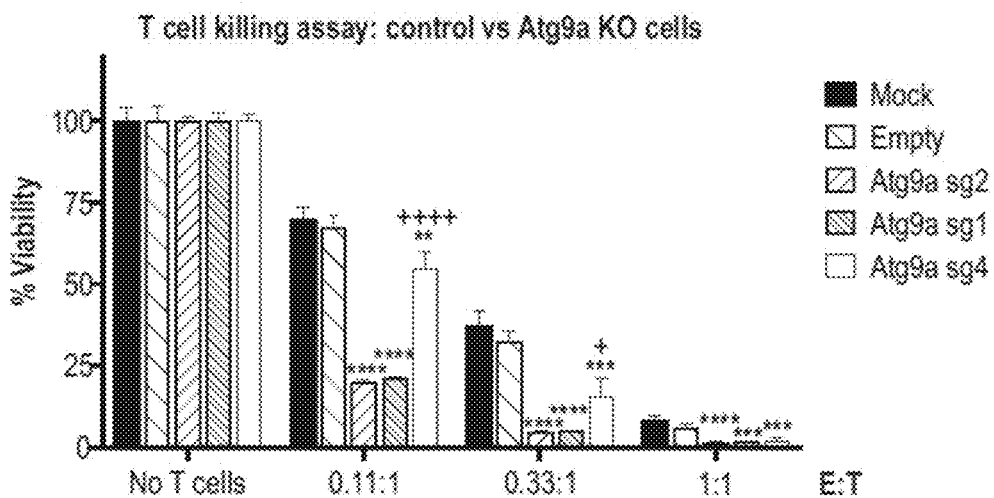
Figure 17:
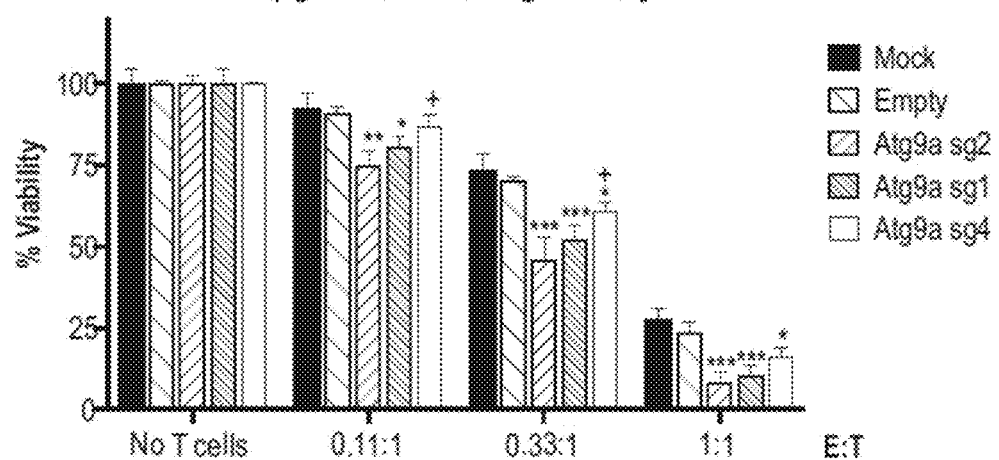
Figure 17:
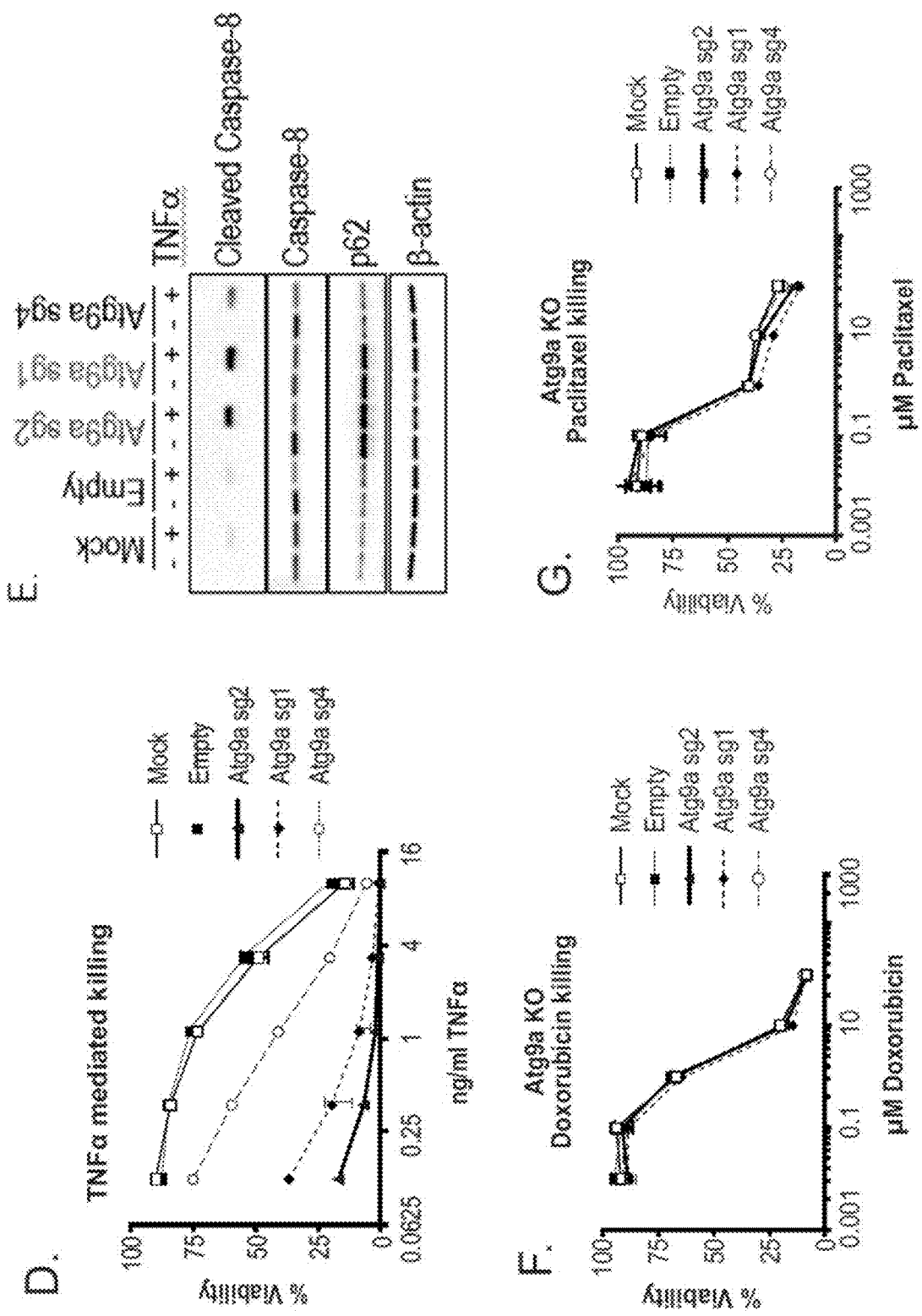
Figure 18:
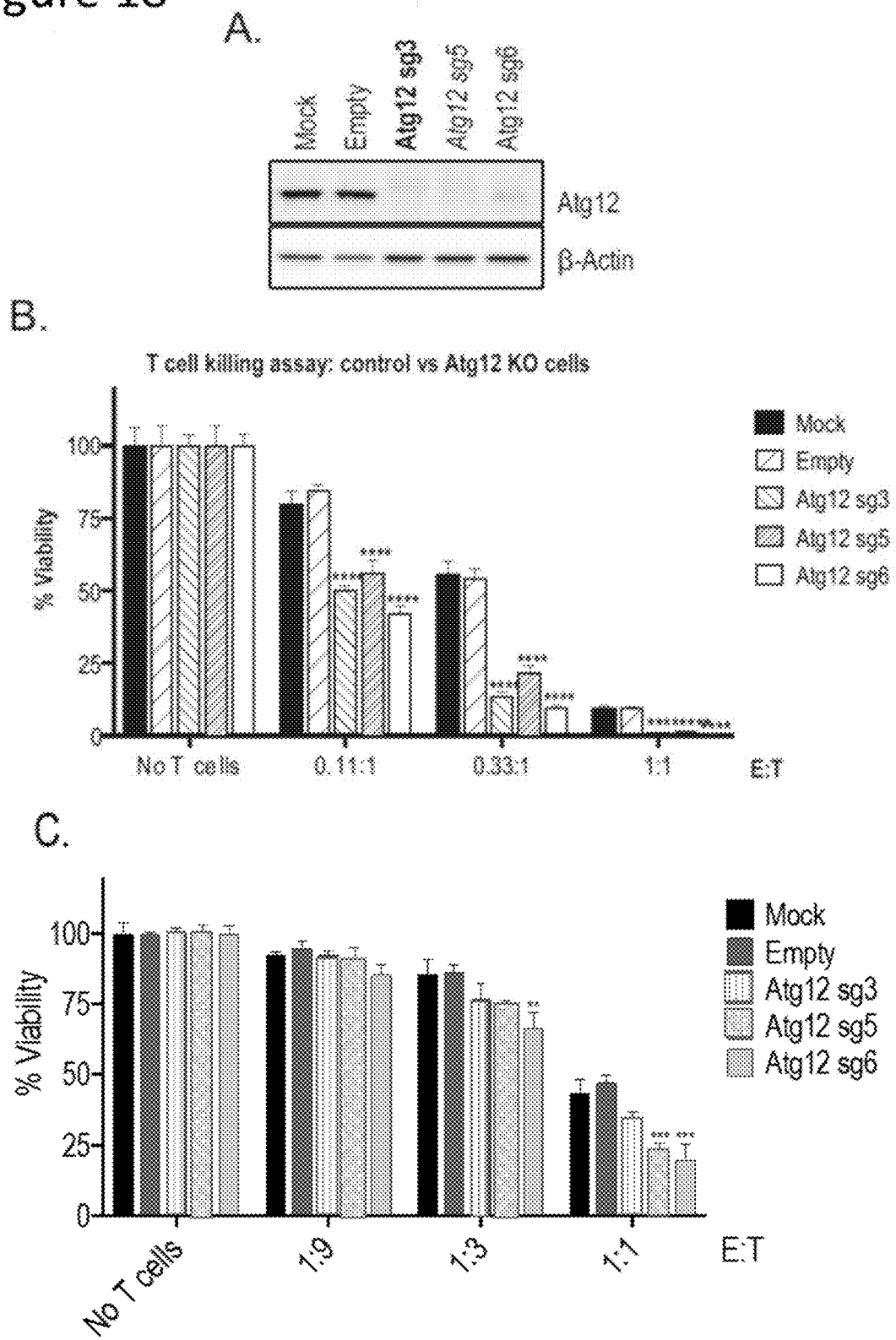
FIG. 18 has seven parts, A-G, and shows Atg12 KO increases tumor cell killing by T cells. Part A shows western blots showing Atg12 and β-actin levels in MC38 parental cells (mock), MC38-Cas9 cells transduced with empty vector or cells expressing Atg12-targeted sgRNAs (sg3 and sg5 were depleted most significantly in the screen; sg6 was depleted least significantly). Part B shows control or Atg12 KO cells were pulsed with Ova peptide and incubated with OT-1 T cells at the indicated E:T ratios for 24 hours. Bar graph shows the relative cell viability±SD (n=3) compared to cells incubated in the absence of T cells. **$P<0.0001$, versus parental MC38 cells, one-way ANOVA with Tukey's multiple comparisons test. Part C shows that T cell killing of the indicated cell lines was performed in the presence of 20 µg/ml TNFα blocking antibody. $P<0.005$, ***$P<0.0005$, versus parental MC38 cells. Part D shows that cells were treated with the indicated concentrations of TNFα and cell viability was measured after 24 hours, n=3. Part E shows western blots showing the levels of the indicated proteins 8 hours after treatment with 10 ng/ml TNFα. Part F and G shows cells were treated with the indicated amounts of doxorubicin or paclitaxel and cell viability was measured after 24 hours, n=3.
Figure 18:
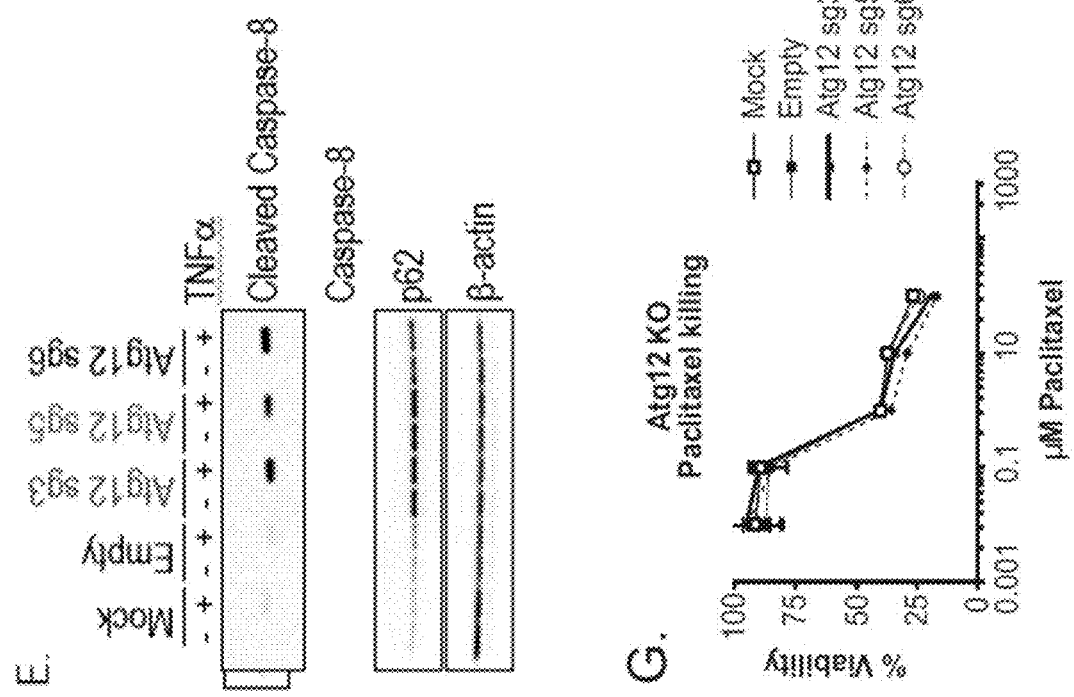
Figure 18:
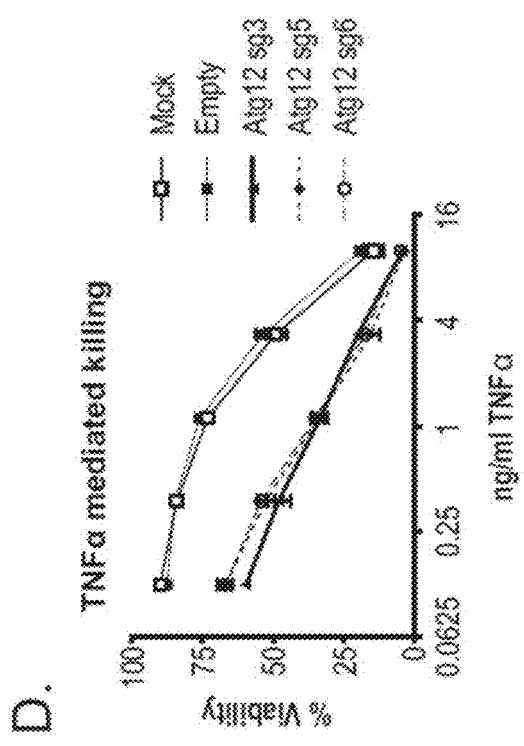
Figure 19:
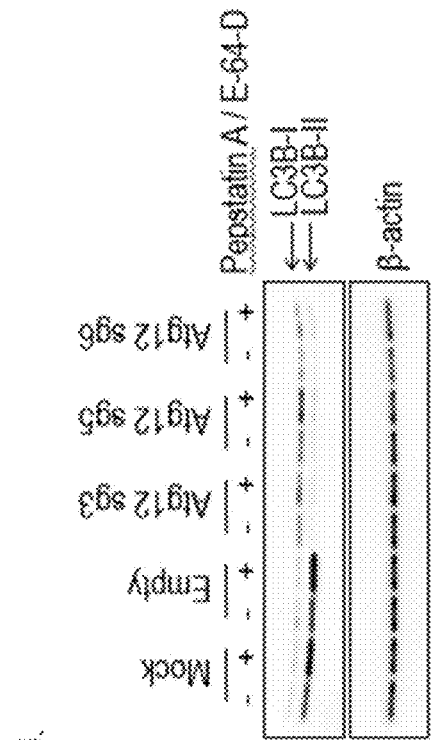
FIG. 19 has two parts, A-B, and shows Rb1cc1 and Atg12 KO cells exhibit impaired autophagic activity. Part A shows western blots showing LC3B and β-actin protein levels in MC38 parental cells (mock), MC38-Cas9 cells transduced with an empty vector or MC38-Cas9 cells expressing Rb1cc1-targeted sgRNAs (Rb1cc1 sg3 was less effective at depleting Rb1cc1 protein than sg4 or sg5—see FIG. 4). Part B shows western blots showing LC3B and β-actin levels in MC38 parental cells (mock), MC38-Cas9 cells transduced with empty vector or MC38-Cas9 cells expressing Atg12-targeted sgRNAs. Cells were treated with 10 µg/ml pepstatin A and 10 µg/ml E-64-D for 4 hours to inhibit lysosomal proteases, which results in LC3B-II accumulation unless autophagy is inhibited upstream. LC3B-II represents the lipidated form of the protein (conjugated to phosphatidylethanolamine).
Figure 19:
Figure 19:
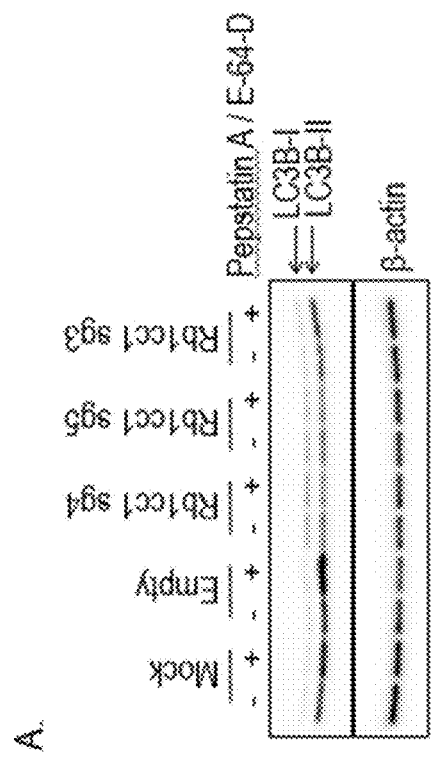

To validate a role for autophagy in limiting tumor cell killing by T cells, three essential autophagy genes (Rb1cc1, Atg9a and Atg12) were inactivated using sgRNAs that were depleted in the screen. Inactivation of Rb1cc1 (also known as FIP200) with multiple sgRNAs sensitized MC38 cells to T cell killing and the extent of Rb1cc1 protein depletion correlated with the degree of sensitization, confirming that these effects are on target (FIG. 4, Parts A and B). Similar results were seen with KO of Atg9a (FIG. 17) and Atg12 (FIG. 18), further validating the protective role of autophagy. Importantly, knockout of these three key autophagy components does in fact impair autophagic activity in MC38 cells, as demonstrated by a significant increase in the levels of the autophagy cargo receptor p62 (also known as sequestosome 1; sqstm1) (FIG. 5, Part A and FIGS. 17 and 18) and a decrease in levels of LC3-II, the lipidated form of the autophagosomal protein LC3 (FIG. 18). Since p62 links ubiquitinated proteins to autophagosomes, and is itself degraded by autophagy, its level increases when autophagy is inhibited. LC3-I is converted to LC3-II via conjugation to phosphatidylethanolamine, which initiates formation and lengthening of the autophagosome. Therefore, inhibition of autophagy upstream of this conversion will inhibit LC3-II formation (Deretic, 2008).

Figure 23:
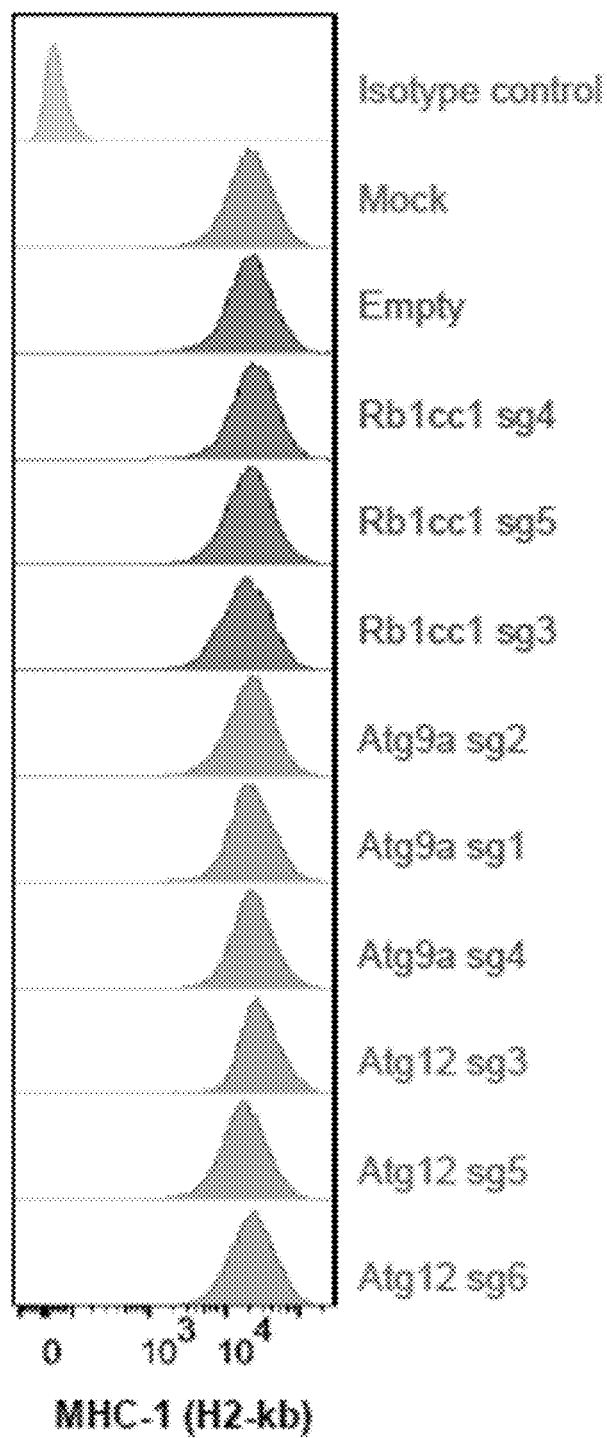
FIG. 23 has two parts, A-B, and shows that KO of autophagy genes in MC38 cells does not affect cell surface MHC-I levels or presentation of OVA peptide. Part A shows flow cytometry histograms showing MHC-1 (H2-kb) cell surface expression in MC38 parental cells (mock), MC38-Cas9 cells transduced with an empty vector or cells expressing Rb1cc1-, Atg9a-, or Atg12-targeted sgRNAs. Part B shows flow cytometry histograms showing MHC-1 (H2-kb)—Ova (SIINFEKL) expression in MC38 parental cells (mock), MC38-Cas9 cells transduced with an empty vector or cells expressing Rb1cc1-targeted sgRNAs. Cells were pulsed with Ova (SIINFEKL) peptide or scrambled peptide, as indicated, before staining.
Figure 23:
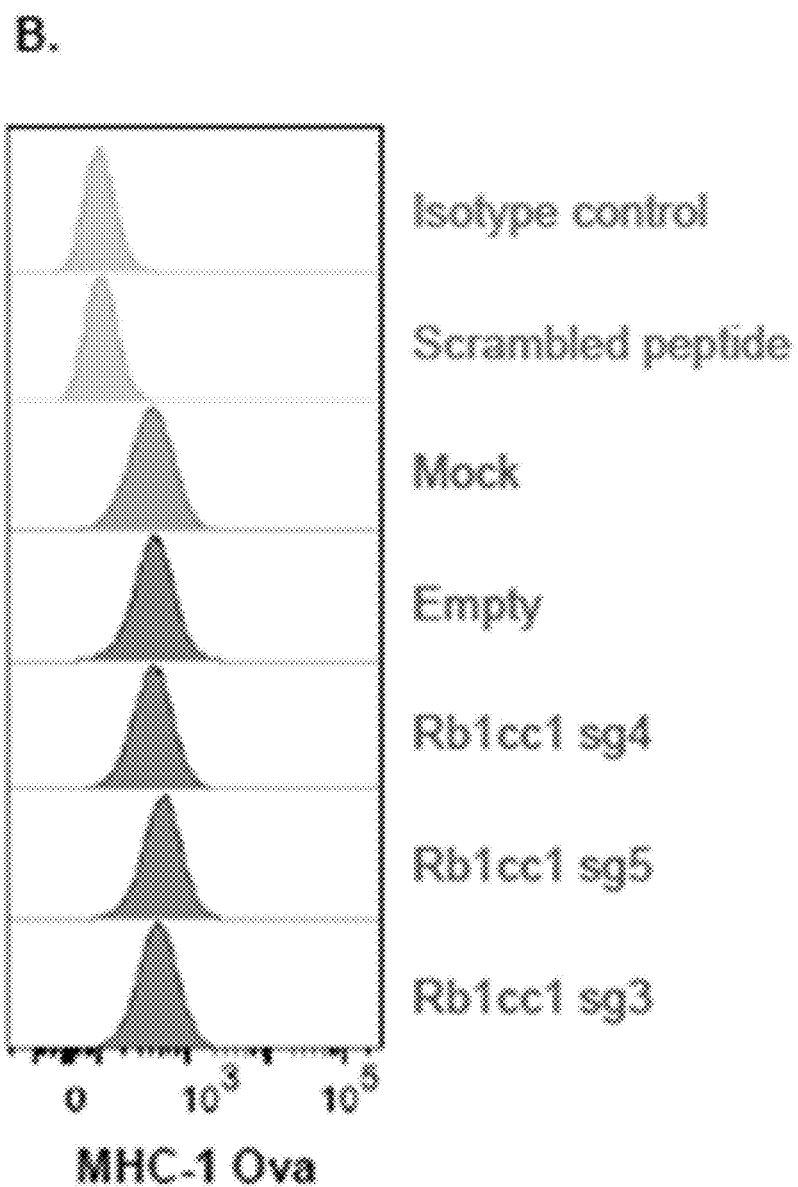

Autophagy has been proposed to inhibit apoptosis by multiple mechanisms, for example via mitophagy—the removal of damaged mitochondria that might be particularly susceptible to outer membrane permeabilization and to triggering the apoptotic cascade. A series of experiments aimed at gaining insight into the mechanism by which autophagy limits tumor cell killing by T cells was performed. Genetic inactivation of autophagy had little or no effect on cell surface MHC-I expression or on presentation of the Ova peptide in MC38 cells (FIG. 23).

As shown in FIG. 4, Part C, Rb1cc1 KO had only a small effect on MC38 cell killing in the presence of a TNFα blocking antibody, indicating that the protective effect of autophagy in the context of T cell killing is mediated primarily through inhibition of TNFα-dependent apoptosis. Similar results were seen with Atg9a and Atg12 KO cells (FIGS. 17 and 18). Consistent with these observations, KO of Rb1cc1, Atg9a or Atg12 significantly increased TNFα-dependent caspase 8 activation and apoptosis (FIG. 4, Part D, FIG. 5, Part A, and FIGS. 17 and 18). Thus, autophagy appears to modulate an early step in the TNFα signaling cascade, at the level of caspase 8 activation (upstream of any mitochondrial involvement). Consistent with a specific signaling function of autophagy in this setting, KO of autophagy genes did not sensitize MC38 cells to killing by the chemotherapeutics doxorubicin or paclitaxel (FIG. 4, Part E, FIGS. 17 and 18).

Figure 5:
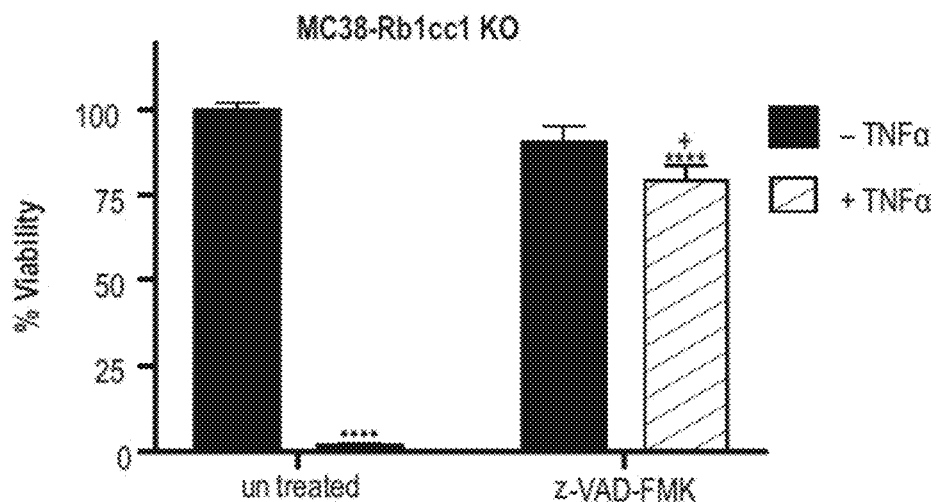
FIG. 5 has nine parts, A-I, and shows inhibition of autophagy enhances TNFα-mediated caspase-8 activation independent of an effect on NF-κB signaling. Part A shows western blots showing levels of the indicated proteins in control or Rb1cc1 KO MC38 cells 4 hours after treatment with 10 ng/ml TNFα. Part B shows western blots showing levels of the indicated proteins in control or Rb1cc1 KO cells 30 minutes (1k-Ba) or 4 hours (A20) after treatment with 10 ng/ml TNFα. Part C shows western blots showing the levels of the indicated proteins in control or Map3k7 (Tak1) KO cells. Part D shows soluble TNFα was added to Rb1cc1 KO cells in the presence or absence of 25 μM z-VAD-FMK (caspase inhibitor) for 24 hours. Bar graph shows the relative cell viability±SD (n=3) compared to control cells (no TNFα, no caspase inhibitor). Groups were compared by one-way ANOVA with Tukey's multiple comparisons test. Part E shows MC38 cells were untreated or treated with 10 ng/ml TNFα in the absence or presence of 5 μM autophinib for 16 hours. Bar graph shows the relative cell viability±SD (n=3) compared to control cells (no TNFα, no autophinib). Part F shows western blots showing the levels of the indicated proteins in cells that were untreated or treated with 10 ng/ml TNFα for 30 minutes (1k-Ba) or 4 hours (caspase-8, p62) in the absence or presence of 5 μM autophinib. Part G shows control, Tnfrsf1a KO, Fadd KO or Ripk1 KO cells were untreated or treated with 10 ng/ml TNFα in the absence or presence of 5 μM autophinib or 1 μM LCL-161 (Smac mimetic) for 24 hours. Bar graphs show the relative cell viability±SD (n=3) compared to control cells (empty vector cells with no TNFα or inhibitor). ****P<0.0001, versus empty vector cells treated with TNFα. Part H shows TNFα was added to Rb1cc1 KO cells in the absence or presence of 50 μM Nec-1 (necroptosis inhibitor) for 24 hours. Bar graph shows the relative cell viability±SD (n=3) compared with control cells (no TNFα, no caspase inhibitor). Part I shows Western blots showing phospho-MLKL, total MLKL and β-actin levels in L929 mouse fibroblast cell line and MC38 parental cells (mock), MC38-Cas9 cells transduced with an empty vector or cells expressing Rb1cc1-targeted sgRNAs. Cells were treated in the presence or absence of 10 ng/ml TNFα, 50 µM Nec-1s, and 20 µM Z-VAD-FMK for 30 min.
Figure 5:
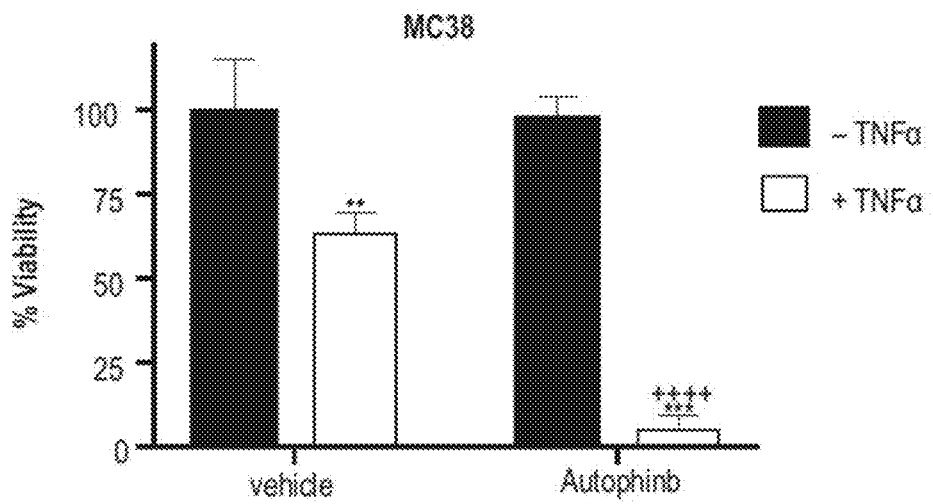
Figure 5:
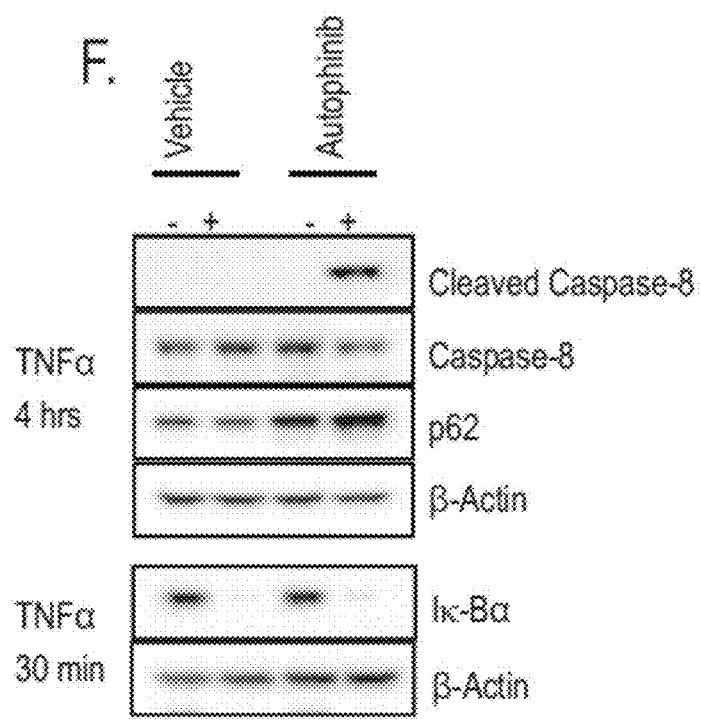
Figure 5:
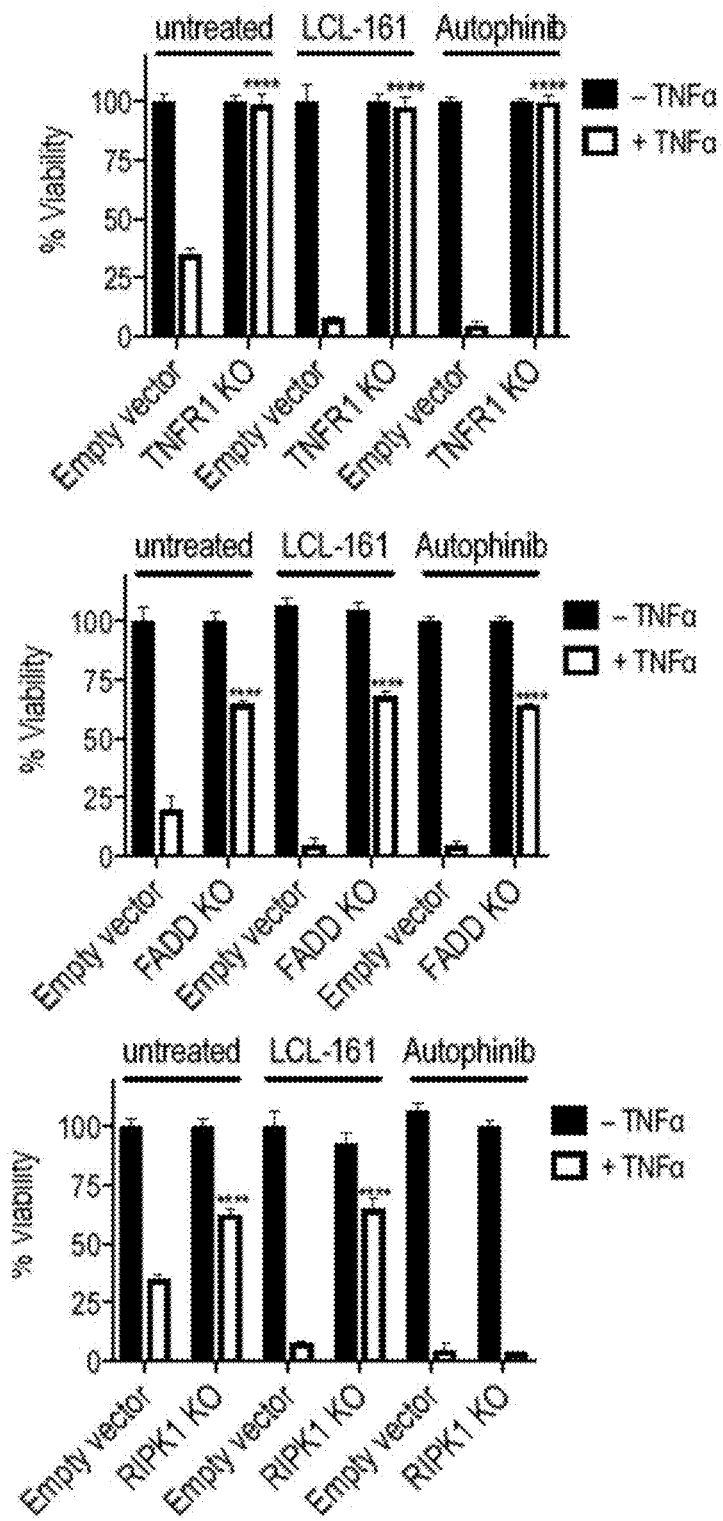
Figure 5:
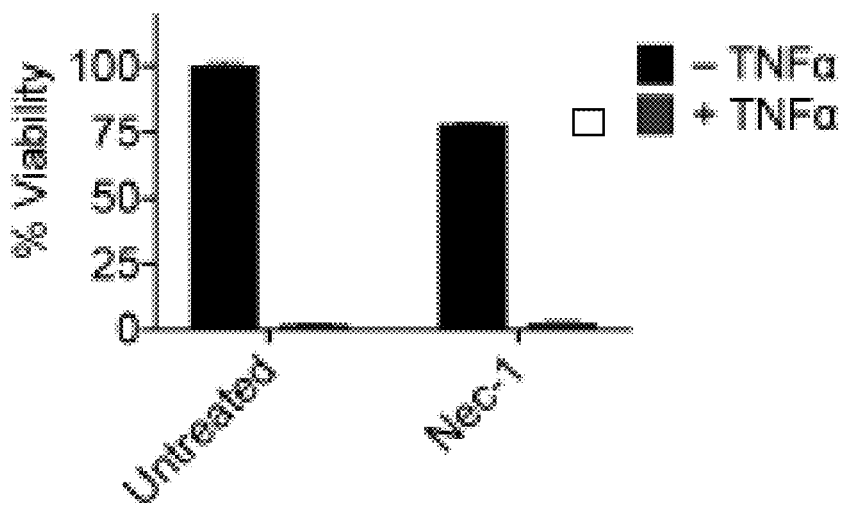
Figure 5:
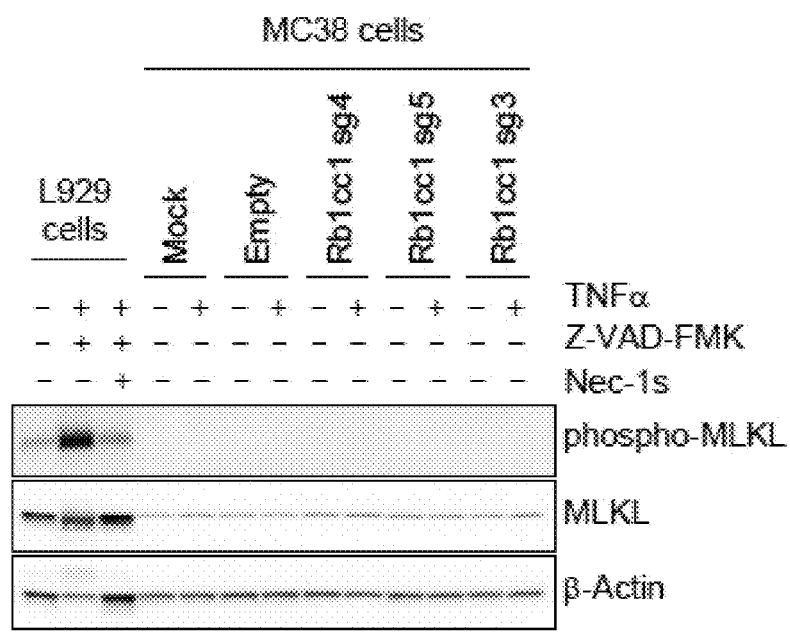
Figure 20:
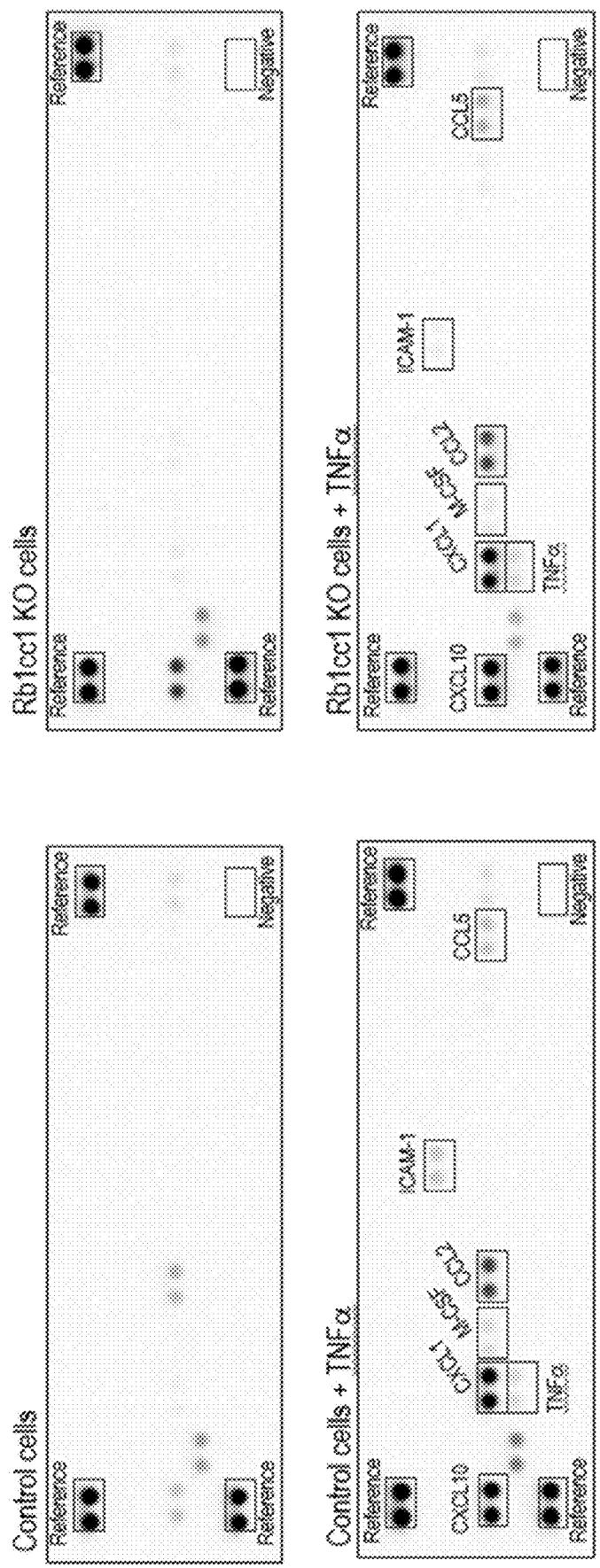
FIG. 20 shows inactivation of autophagy does not impair TNFα-mediated induction of NF-κB target genes. Control or Rb1cc1 KO MC38 cells were either untreated or treated with 10 ng/ml TNFα for 4 hours. Cell lysates were then assayed on a mouse cytokine array to determine the levels of 40 mouse cytokines. Cytokines upregulated by TNFα are labeled.

Given that both the NF-κB and autophagy pathways limit tumor cell killing by T cells, it was investigated whether possible mechanistic connections between these pathways. One possibility is that inactivation of autophagy somehow results in a defect in NF-κB signaling, thereby sensitizing to TNFα-mediated apoptosis. However, KO of the autophagy gene Rb1cc1 did not affect TNFα-mediated degradation of Iκ-Bα, induction of the NF-κB target gene A20 or induction of several chemokines that require NF-κB for expression (e.g., CXCL10 and CCL2) (FIG. 5, Part B, FIG. 20). Thus, autophagy does not limit TNFα-mediated apoptosis in MC38 cells as a result of a required role in NF-κB activation. Conversely, levels of the autophagy receptor p62 were not affected by Map3k7 KO (FIG. 5, Part C), suggesting that an intact NF-κB pathway is not required for autophagic activity.

Next, the mechanism by which TNFα kills cells when autophagy is inhibited was explored. The observation that inactivation of Rb1cc1 increases TNFα-induced caspase-8 activation suggests that in the context of an impaired autophagy pathway, TNFα kills cells via apoptosis rather than necroptosis. In support of this contention, a pan-caspase inhibitor blocked TNFα-mediated killing in Rb1cc1 KO cells (FIG. 5, Part D), whereas a necropsis inhibitor had no effect (FIG. 5, Part H). In accord with these observations, TNFα did not induce phosphorylation of mixed lineage kinase domain—like protein (MLKL), a mediator of necroptosis, in Rb1cc1 KO cells (FIG. 5, Part I).

TNFα-induced apoptosis can occur via multiple molecular mechanisms, distinguished by the involvement of the kinase RIPK1. To enable genetic dissection of TNFα signaling in the context of autophagy inhibition, autophinib, a selective small molecule inhibitor of the lipid kinase Vps34, was employed. It is essential for autophagosome formation. Treatment of MC38 cells with autophinib increased TNFα-mediated caspase-8 activation and killing (and significantly increased the levels of p62, confirming autophagy blockade) (FIG. 5, Parts E and F). Importantly, autophinib did not affect TNFα-mediated degradation of Iκ-Bα (FIG. 5, Part F), indicating that impaired autophagy does not lead to a defect in the NF-κB pathway (consistent with the Rb1cc1 KO data shown above).

Figure 24:
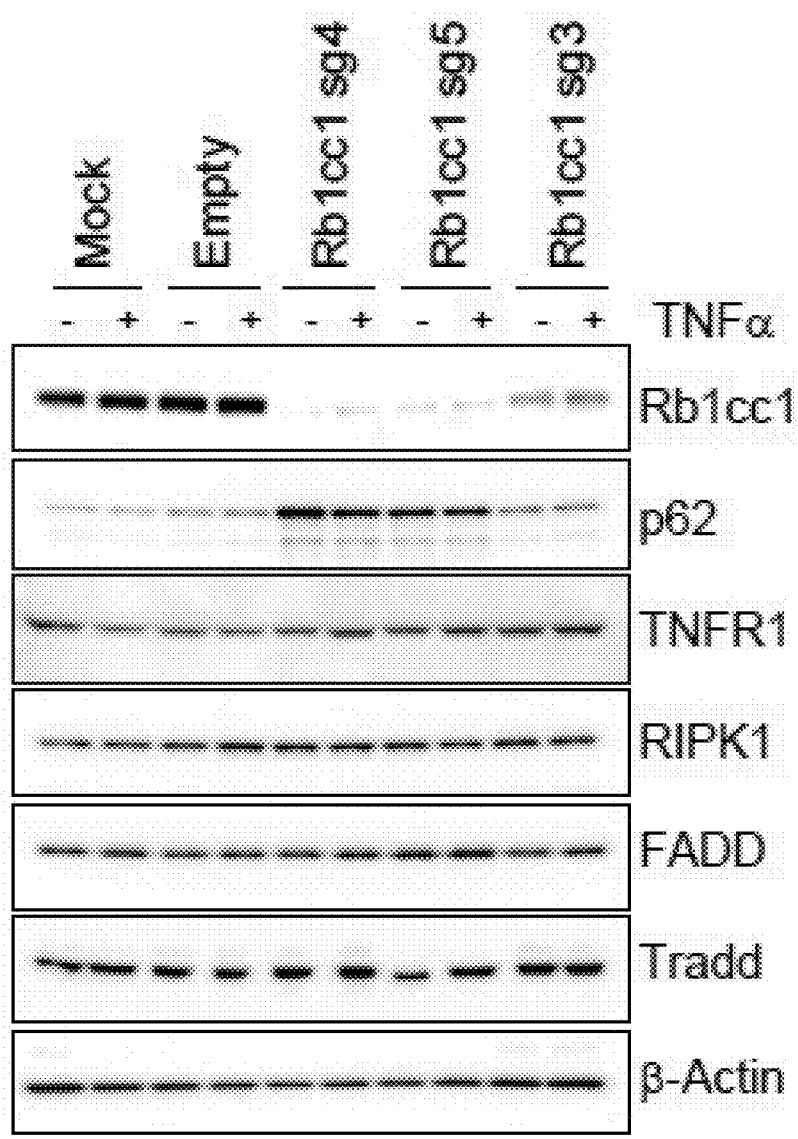
FIG. 24 shows that tiactivation of autophagy does not increase the levels of key TNFα pathway components. Western blots showing levels of indicated proteins in MC38 parental cells (mock), MC38-Cas9 cells transduced with an empty vector or cells expressing Rb1cc1-targeted sgRNAs, 30 minutes after treating with 10 ng/ml TNFα.
Figure 25:
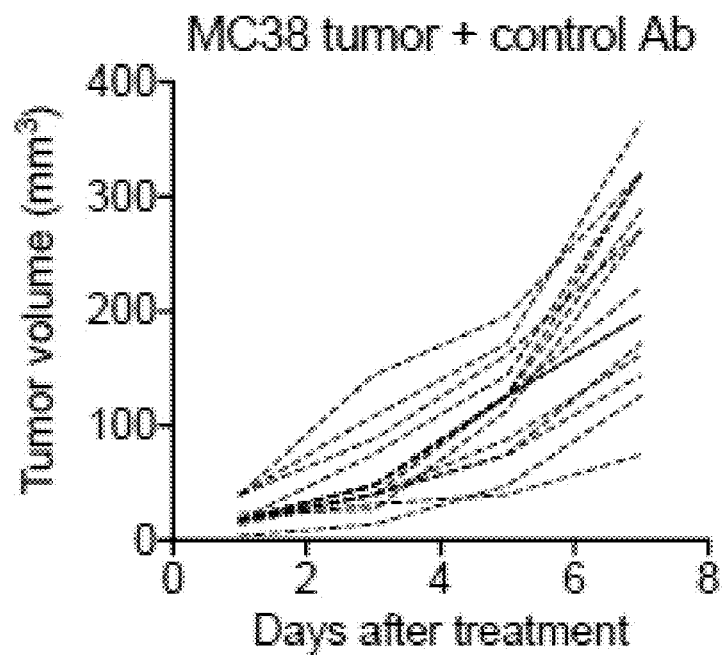
FIG. 25 shows that treating MC38 tumors early with PD-1/CTLA-4 antibodies results in complete tumor regression. MC38 cells were implanted into C57/BL6 mice. Three days after implantation, mice were treated with either isotype control or PD-1 plus CTLA-4 blocking antibodies. Individual tumor growth curves for each mouse are shown, n=15.
Figure 25:
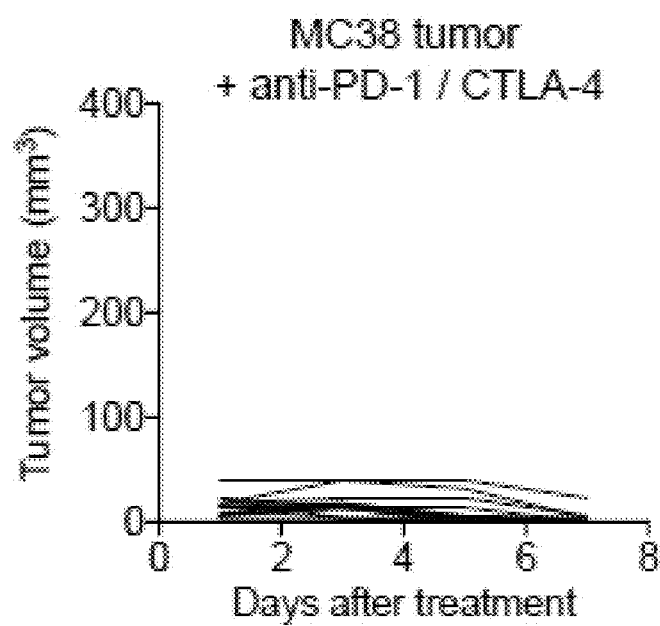

It is well-established that one important mechanism through which cells limit TNFα-induced killing is inhibition of the apoptotic activity of RIPK1. Among the molecular events that contribute to this "early checkpoint" in the TNFR1 signaling pathway is the ubiquitination of RIPK1 by cIAP. Thus, inhibition of cIAP function with Smac mimetics promotes FADD/RIPK1/caspase-8 dependent apoptosis (see model in FIG. 2, Part A). Consistent with this model, CRISPR-mediated inactivation of Ripk1, Fadd or Tnfrsf1a significantly decreased killing by TNFα in the presence of Smac mimetic (FIG. 5, Part G). However, while inactivation of Ripk1, Tnfrsf1a or Fadd also significantly decreased killing by TNFα in the presence of autophinib, inactivation of Ripk1 had no effect (FIG. 5, Part G). Therefore, in cells with impaired autophagy, TNFα-induced apoptosis is FADD/caspase-8 dependent but RIPK1 independent, suggesting that the early checkpoint in the TNFR1 signaling pathway remains functional. Thus, autophagy appears to inhibit TNFα-induced apoptosis by limiting the formation and/or activity of the FADD/caspase-8 complex and not by limiting RIPK1 activity. Inactivation of autophagy did not affect the total protein levels of TNFR1, TRADD (TNFR1-associated death domain protein), or FADD, indicating that potentiation of TNFα-induced apoptosis is not driven simply by elevated levels of these key pathway components (FIG. 24).

Given that both the NF-κB and autophagy pathways limit tumor cell killing by T cells, possible mechanistic connections between these pathways were investigated. One possibility is that inactivation of autophagy results in a defect in NF-κB signaling, thereby sensitizing to TNFα-mediated apoptosis. However, KO of Rb1cc1 did not affect TNFα-mediated degradation of Iκ-Bα, induction of the NF-κB target gene A20, or induction of several chemokines that require NF-κB for expression (e.g., CXCL10 and CCL2) (FIG. 4G and FIG. 20). Thus, impaired autophagy does not result in defective NF-κB activation. Conversely, levels of the autophagy receptor p62 were not affected by Map3k7 KO (FIG. 4H), suggesting that an intact NF-κB pathway is not required for autophagic activity.

Figure 21:
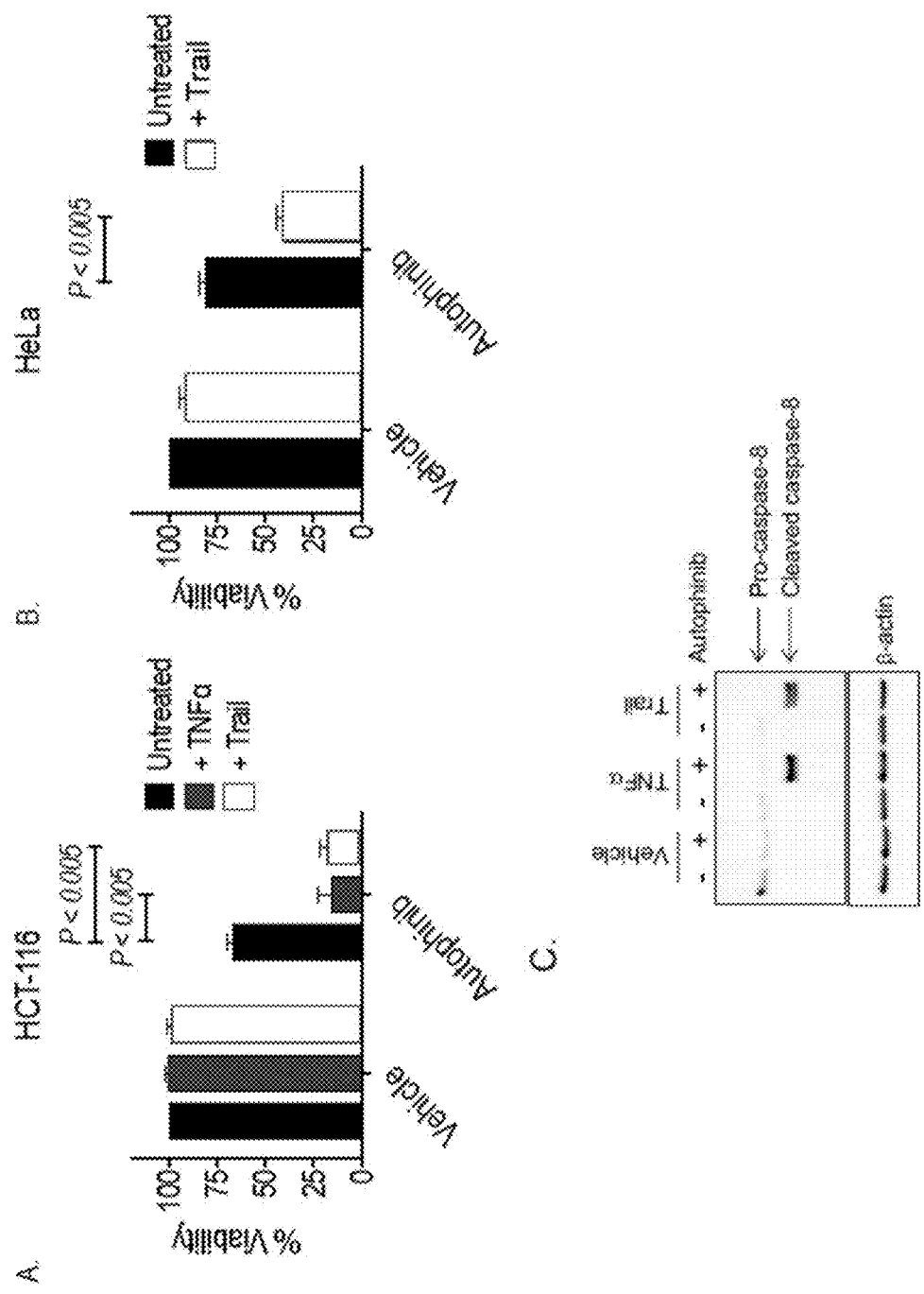
FIG. 21 has three parts, A-C, and shows pharmacologic blockade of autophagy sensitizes human cancer cells to TNFα- and TRAIL-mediated killing. Part A shows HCT-116 human colon cancer cells were untreated or treated with 10 ng/ml TNFα or 10 ng/ml TRAIL in the absence or presence of 5 µM autophinib. Cell viability was measured after 24 hours. Part B shows HeLa human cervical cancer cells were untreated or treated with 50 ng/ml TRAIL in the absence or presence of 5 µM autophinib. Cell viability was measured after 24 hours. Bar graphs show the relative cell viability±SD (n=3). Treatment groups were compared by one-way ANOVA with Tukey's multiple comparisons test. Part C shows western blots showing levels of indicated proteins in HCT-116 cells 24 hours after treatment with 10 ng/ml TNFα or 10 ng/m Trail in the absence or presence of 5 mM autophinib. Part D shows western blots showing levels of indicated proteins in HeLa cells 24 hours after treatment with 50 ng/ml TRAIL in the absence or presence of 5 µM autophinib. Part E is graph summarizing results observed for MC38 cells that were untreated or treated with 10 ng/ml TNFα or 10 ng/ml TRAIL in the absence or presence of 5 µM SAR405 or autophinib. Cell viability was measured after 24 hours. Part F is a graph summarizing results for EMT6 cells that were untreated or treated with 10 ng/ml TNFα or 10 ng/ml TRAIL in the absence or presence of 5 µM SAR405 or autophinib. Cell viability was measured after 24 hours. Bar graphs show the relative cell viability±SD (n=3). ****P<0.0001, versus untreated cells, one-way ANOVA with Tukey's multiple comparisons test.
Figure 21:
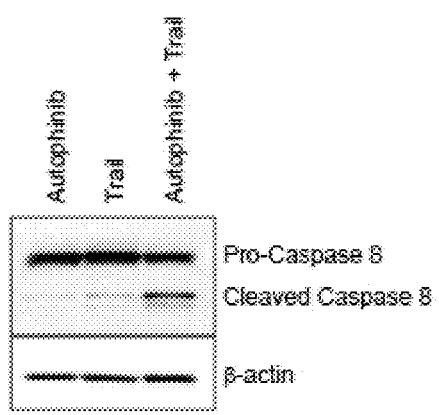
Figure 21:
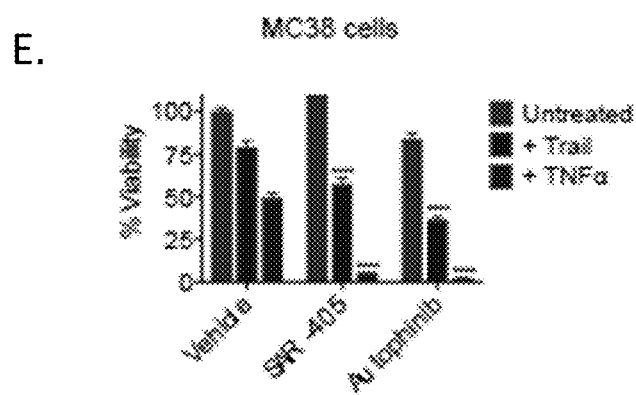
Figure 21:
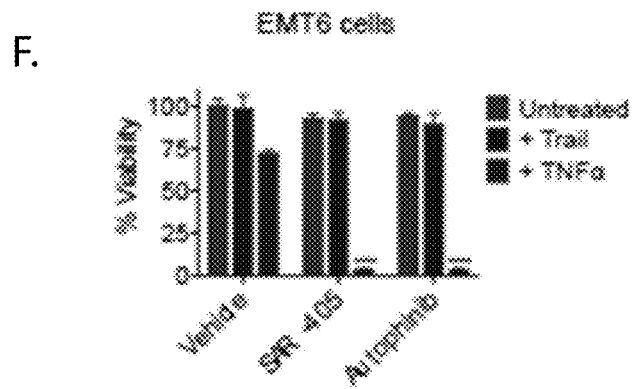

TRAIL promotes apoptosis through activation of two TNFRSF family receptors, TRAIL-R1 and TRAIL-R2. To determine whether autophagy can also limit apoptotic signaling downstream of TRAIL-R, cancer cells were challenged with TRAIL in the absence or presence of autophinib. As shown in FIG. 21, Parts A-C, activation of caspase-8 and induction of apoptosis by TRAIL in human cancer cells was increased when autophagy was blocked, suggesting that autophagy can limit apoptotic signaling by multiple death receptors (possibly via an effect on the activity of the FADD/caspase-8 complex, which is integral to the induction of apoptosis by both TNFα and TRAIL). Although autophagy inhibition sensitized MC38 cells to TRAIL, these cells are killed much more effectively by TNFα (FIG. 21, Parts A-F).

Tumor Cell mTOR Signaling Increases Sensitivity to T Cell/TNFα-Mediated Killing

Multiple sgRNAs targeting genes in the mTOR pathway (e.g., Mlst8, Mtor, Rictor, Mapkap1) were enriched in the screen, suggesting that mTOR signaling is required for efficient tumor cell killing. The mTOR pathway is an essential regulator of cell metabolism, linking nutrient levels and growth factors to cell growth and proliferation. Consistent with its role in promoting cell growth, mTOR signaling inhibits autophagic activity via multiple mechanisms. Given the findings on the protective role of autophagy, it seems that mTOR might increase tumor cell susceptibility to T cell-mediated killing through inhibition of autophagy.

Figure 6:
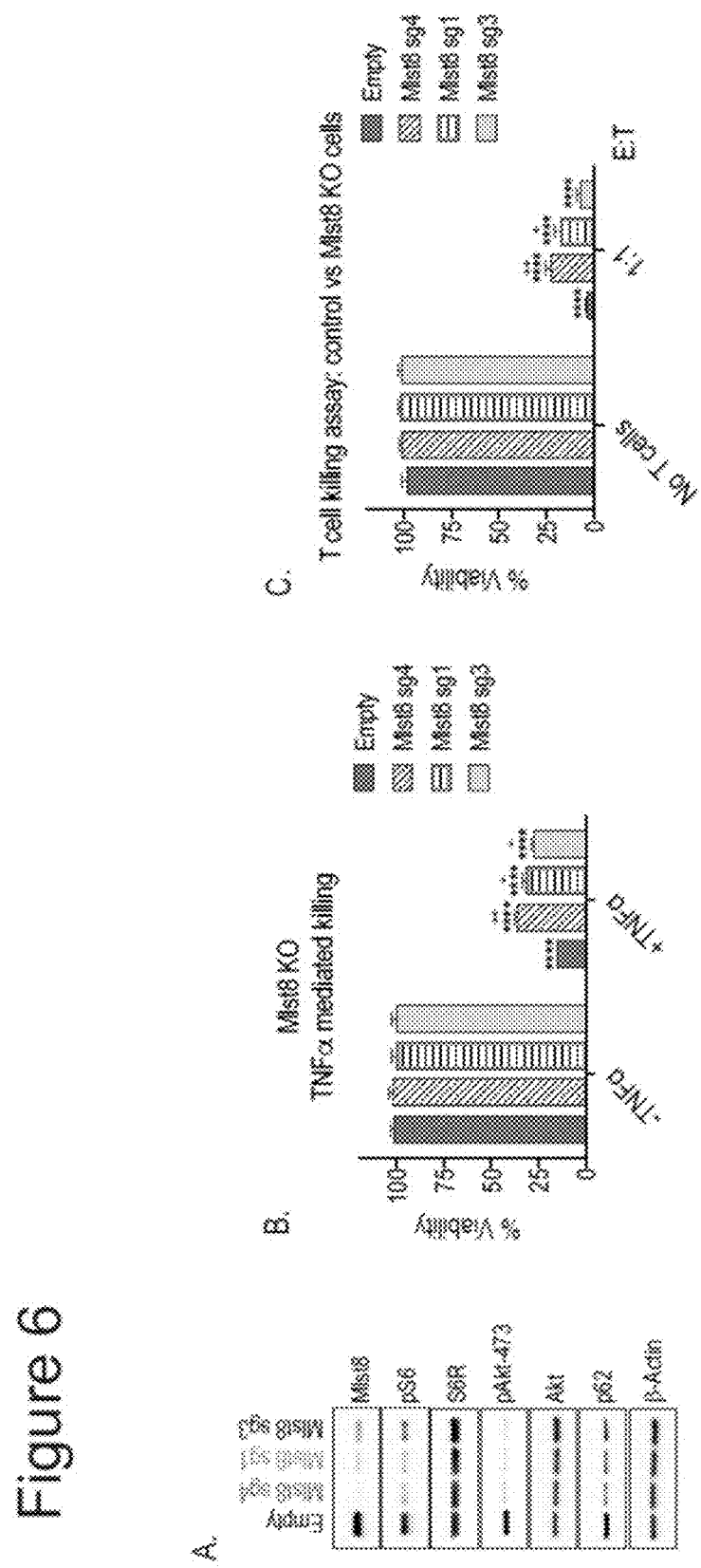
FIG. 6 has seven parts, A-G, and shows mTOR signaling in tumor cells is required for maximal TNFα- and T cell-mediated killing. Part A shows western blots showing levels of the indicated proteins in MC38 cells transduced with an empty vector or cells expressing Mlst8-targeted sgRNAs (sg4 and sg1 were enriched most significantly in the screen; sg3 was enriched least significantly). Part B shows control or Mlst8 KO cells were untreated or treated with 10 ng/ml TNFα for 24 hours. Bar graph shows the relative cell viability±SD (n=3) compared to control cells (no TNFα). *P<0.05, **P<0.005, versus empty vector cells treated with TNFα, one-way ANOVA with Tukey's multiple comparisons test. Part C shows control or Mlst8 KO cells were pulsed with Ova peptide and incubated with OT-1 T cells for 24 hours. Bar graph shows the relative cell viability±SD (n=3) compared to control cells (no T cells). *P<0.05, **P<0.005, versus empty vector cells incubated with T cells. Part D shows western blots showing levels of the indicated proteins in MC38 cells treated with 200 nM rapamycin for the indicated times. Part E shows wells pretreated with vehicle or 200 nM rapamycin were then either untreated or treated with 10 ng/ml TNFα for 24 hours. Bar graph shows the relative cell viability±SD (n=3) compared to control cells (vehicle, no TNFα). Part F shows cells pretreated with vehicle or rapamycin were pulsed with either scrambled control peptide or Ova peptide and incubated with OT-1 T cells for 24 hours. Bar graph shows the relative cell viability±SD (n=3) compared to control cells (no T cells, scrambled peptide). Part G shows diagram depicting tumor cell pathways that modulate killing by T cells.
Figure 6:
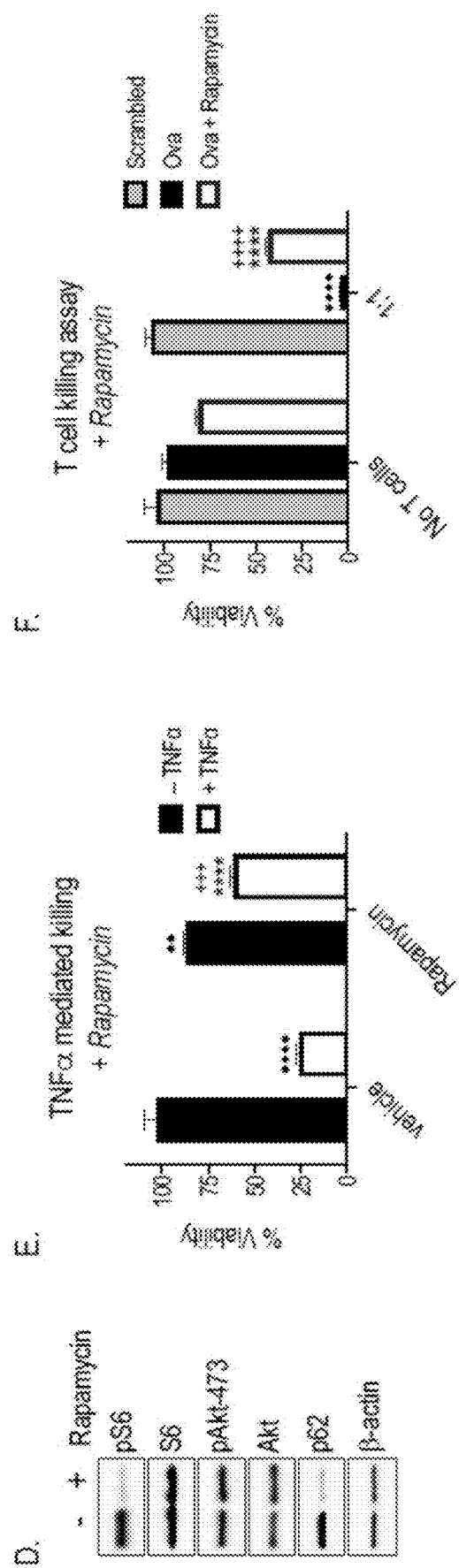
Figure 6:
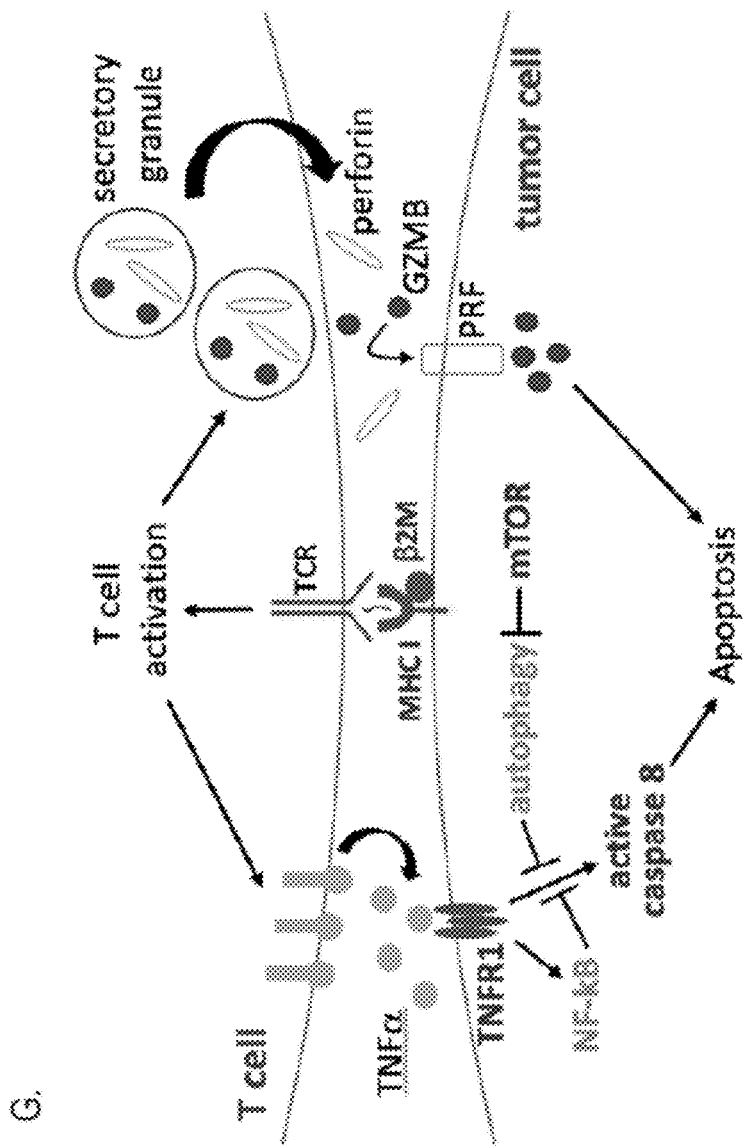

To confirm the screen results, Mlst8 (an essential component of both of the mTOR signaling complexes, mTORC1 and mTORC2) was inactivated using sgRNAs enriched in the screen. Inactivation of Mlst8 inhibited both mTORC1 and mTORC2 activity as evidenced by decreased phospho-S6 (mTORC1-dependent) and decreased phospho-Akt levels (mTORC2-dependent) (FIG. 6A). Consistent with inhibition of autophagy by mTOR signaling, Mlst8 KO cells exhibited decreased p62 levels, confirming increased autophagic activity (FIG. 6, Part A). Elevated autophagy in Mlst8 KO cells was associated with decreased sensitivity to both TNFα- and T cell-mediated killing (FIG. 6, Part B and C). Importantly, the magnitude of the effect of each Mlst8 sgRNA on tumor cell killing correlated with the extent of Mlst8 protein depletion (FIG. 6, Part A), confirming that these effects are on target. To further illustrate the impact of the mTOR pathway on tumor cell killing, mTORC1 signaling was blocked with rapamycin, which results in decreased phospho-S6 and p62 levels (confirming elevated autophagic activity) (FIG. 6, Part D). Inhibition of mTORC1 with rapamycin, similar to Mlst8 KO, significantly decreased both TNFα- and T cell-mediated killing (FIG. 6, Part E and F).

These findings on the effects of mTOR modulation further support the importance of autophagy as a protective mechanism in tumor cells. A diagram depicting the modulation of T cell-mediated tumor cell killing by the various signaling pathways identified in the screen is presented in FIG. 6, Part G.

Figure 7:
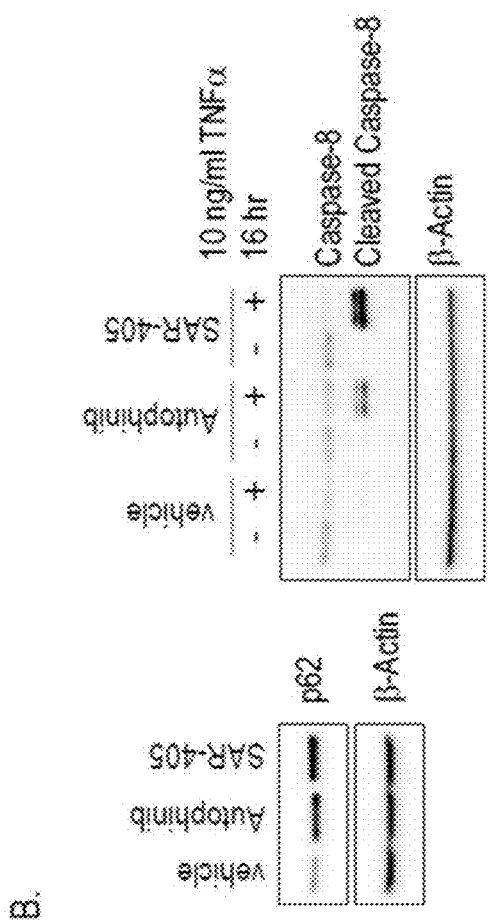
FIG. 7 has six parts, A-F, and shows autophagy limits CD3 bispecific antibody-induced killing of human cancer cells. Part A shows human ZR-75-1 breast cancer cells were untreated or treated with 10 ng/ml TNFα in the absence or presence of 5 µM autophinib or SAR-405 for 24 hours. Bar graph shows the relative cell viability±SD (n=3) compared to control cells (vehicle, no TNFα). Groups were compared by one-way ANOVA with Tukey's multiple comparisons test. Part B shows western blots showing levels of the indicated proteins after 16 hours treatment of ZR-75-1 cells with 5 µM autophinib or SAR-405 in the absence or presence of 10 ng/ml TNF**. Part D shows ZR-75-1 cells were incubated for 24 hours with activated human T cells at the indicated E:T ratio in the presence of 12 ng/ml control or breast tumor antigen×CD3 (TAAxCD3 (illustrated in Part C) bispecific antibodies in the absence or presence of 5 µM SAR-405. Bar graph shows the relative cell viability±SD (n=3) compared to control cells (no T cells, control bispecific antibody). Part E shows western blots showing levels of the indicated proteins in ZR-75-1 control or Rb1cc1 KO cells. Part F shows ZR-75-1 control or Rb1cc1 KO cells were incubated with T cells plus bispecific antibodies as above. Bar graph shows the relative cell viability±SD (n=3) compared to control cells+control bsAb. P<0.005, versus control cells. ****P<0.0001, versus control cells+CD3 bsAb. ++++P<0.0001, versus Rb1cc1 KO+CD3 bsAb.
Figure 7:
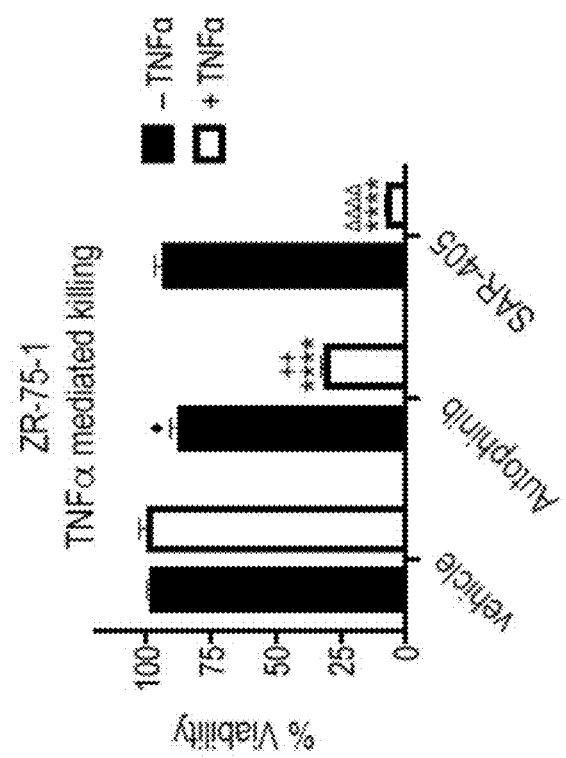
Figure 7:
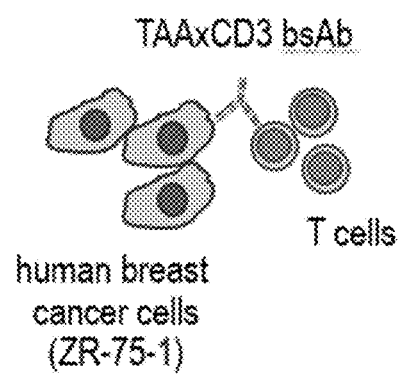
Figure 7:
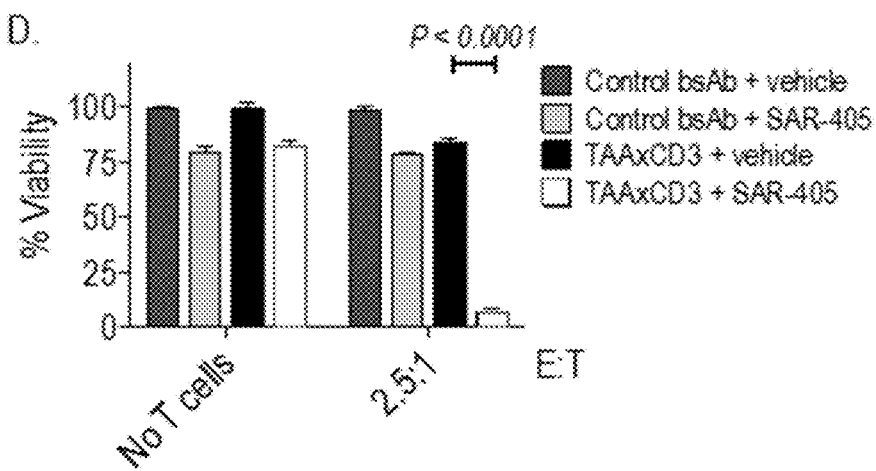
Figure 7:
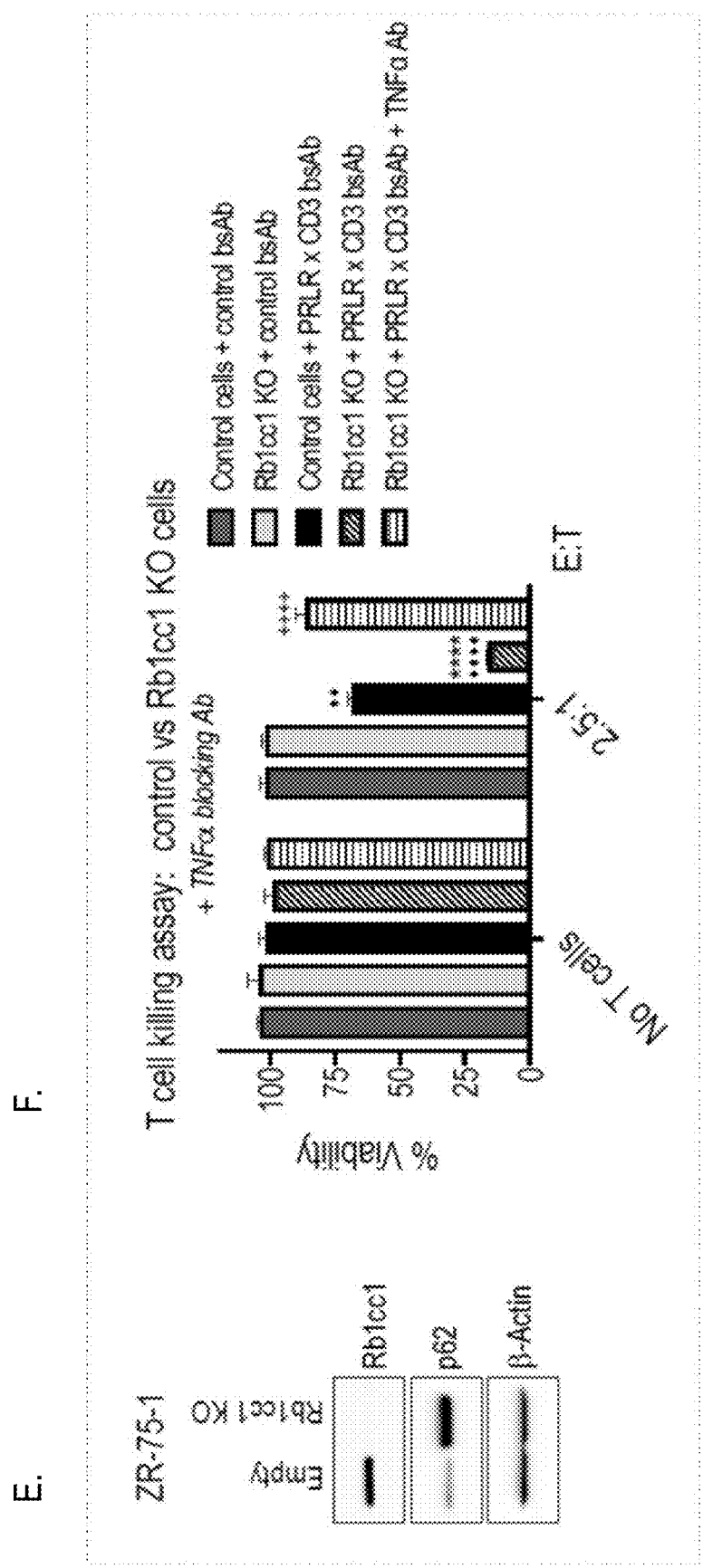
Figure 22:
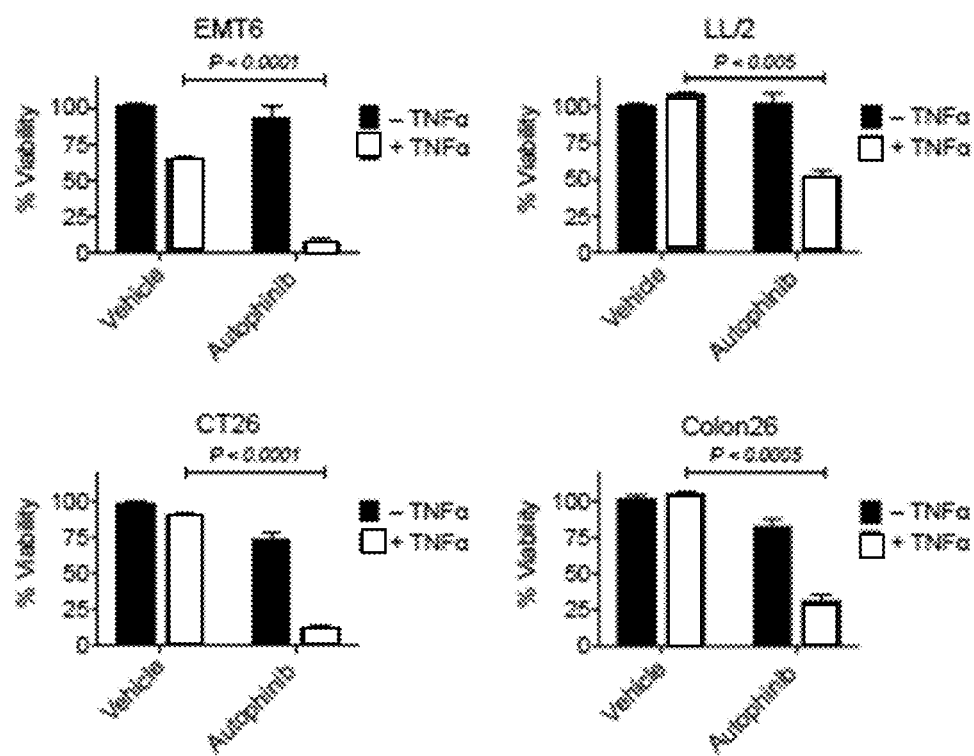
FIG. 22 has two parts, A-B, and shows pharmacologic blockade of autophagy sensitizes several mouse and human cancer cell lines to TNFα-mediated killing. Part A shows mouse tumor cell lines (EMT6, LL/2, CT26, Colon26) were untreated or treated with 10 ng/ml TNFα in the absence or presence of 5 µM autophinib and cell viability was measured after 24 hours. Part B shows human tumor cell lines (BT-20, Me-180, MDA-MB-361) were untreated or treated with 10 ng/ml TNFα in the absence or presence of 5 µM autophinib or 5 µM SAR-405 and cell viability was measured after 24 hours. Bar graphs show the relative cell viability±SD (n=3). Treatment groups were compared by one-way ANOVA with Tukey's multiple comparisons test.
Figure 22:
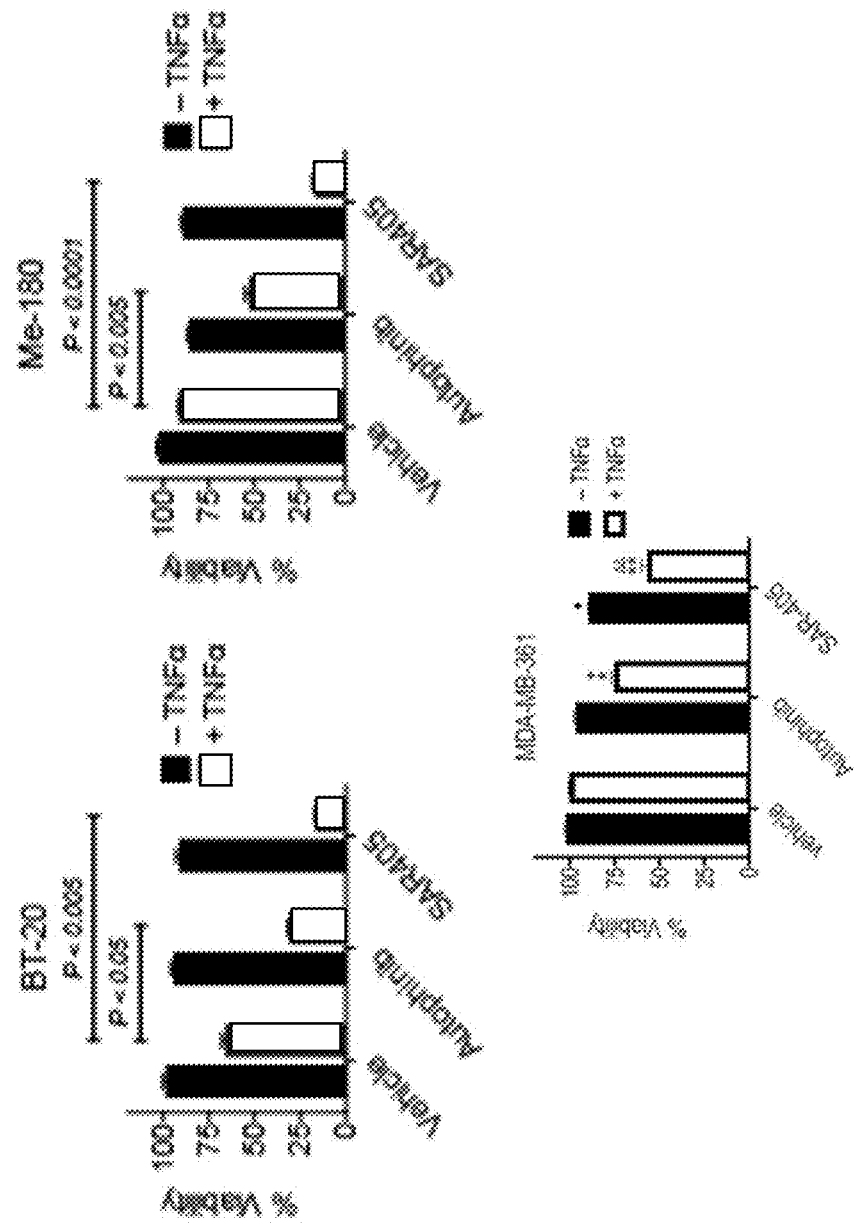

Autophagy Protects Cancer Cells of Various Lineages from T Cell- and TNFα-Mediated Killing To extend the findings on the protective role of autophagy, autophinib and SAR405 was used, another Vps34 blocker, to assess the effect of autophagy inhibition in a panel of cancer cell lines. While autophinib and SAR405 both target Vps34, these inhibitors are structurally distinct and are therefore likely to have different off-target effects. Both of the autophagy inhibitors significantly increased killing by TNFα in multiple mouse and human cancer cell lines from different lineages (e.g., colon, breast, lung), including cell lines that exhibit no sensitivity to TNFα at baseline (FIG. 7, Part A, FIG. 22). The autophagy inhibitors significantly increased p62 levels (confirming autophagy blockade) and enhanced TNFα-induced activation of caspase-8 in human breast cancer cells (FIG. 7, Part B). Therefore, a protective role for autophagy in the context of TNFα treatment appears to be broadly relevant.

Thus far it has been shown that TNFα contributes to tumor cell killing when T cells are activated through engagement of the T cell receptor by an MHC class I/peptide complex on the target cell. Under these conditions, it has been shown that tumor cell autophagy plays a substantial protective role. To further support the potential clinical relevance of the findings, it was asked whether autophagy also modulates tumor cell killing by T cells following stimulation with a CD3 bispecific antibody. These antibodies, a new and promising therapeutic class, bind to a tumor antigen with one arm and to CD3 on T cells with the other arm, thereby bridging tumor cells and cytotoxic T cells to enable tumor cell killing (FIG. 7, Part C). A breast tumor antigen×CD3 bispecific antibody (generated at Regeneron) was employed to promote killing of ZR-75-1 human breast cancer cells by human T cells. As shown in FIG. 7, Part C, inhibition of autophagy with SAR-405 significantly increased tumor cell killing. Consistent with the effect of pharmacologic blockade of autophagy, genetic inactivation of autophagy through Rb1cc1 KO enhanced CD3 bispecific antibody-induced killing (FIG. 7, Parts D and E). Taken together, these findings confirm the protective role of autophagy in the context of T cell killing induced by a CD3 bispecific antibody and the protective role of autophagy in human breast cancer cells.

Genetic Inactivation of Autophagy Sensitizes Tumors to Immunotherapy

Figure 8:
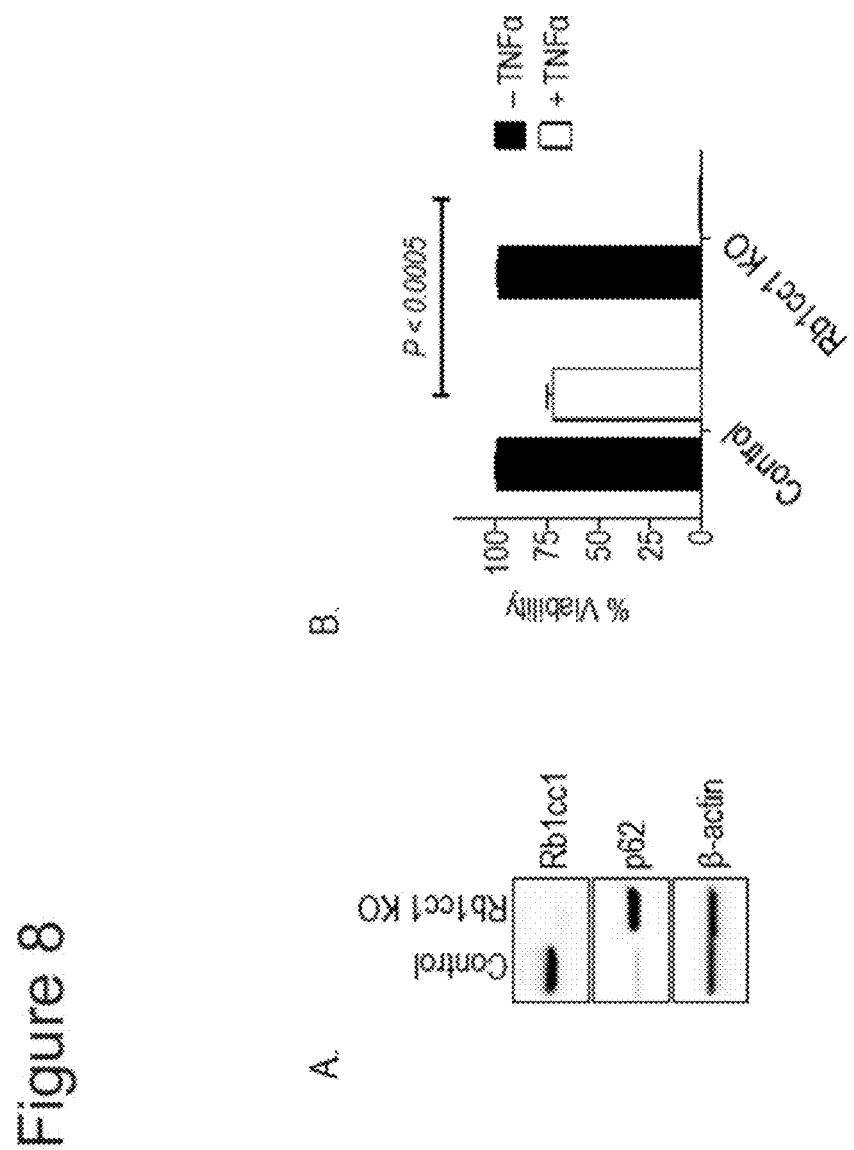
FIG. 8 has seven parts, A-G, and shows inactivation of autophagy sensitizes tumors to immunotherapy. Part A shows western blots showing the levels of the indicated proteins in EMT6 control (non-targeting sgRNA) or Rb1cc1 KO cells. Part B shows EMT6 control or Rb1cc1 KO cells were treated with 10 ng/ml TNFα and viability was measured after 24 hours. Bar graph shows the relative cell viability±SD (n=3) compared to control cells (control, no TNFα). Groups were compared by one-way ANOVA with Tukey's multiple comparisons test. Part C shows EMT-6 cells (control or Rb1cc1 KO) were implanted into Balb/c mice. Three days after implantation, mice were treated with either isotype control or PD-1 plus CTLA-4 blocking antibodies as described in the Methods (n=10 mice per group). The line graph depicts the average tumor volumes±SEM for each group. Groups were compared by two-way ANOVA with Tukey's multiple comparisons test. Part D shows individual tumor growth curves for each mouse. Part E shows western blots showing the levels of the indicated proteins in MC38 control (non-targeting sgRNA) or Rb1cc1 KO cells. Part F shows MC38 cells (control or Rb1cc1 KO) were implanted into C57/BL6 mice. Mice were randomized when tumors were ~70 mm$^3$ (7-12 mice per group) and treated with either isotype control or PD-1 plus CTLA-4 blocking antibodies. The line graph depicts the average tumor volumes±SEM for each group. Groups were compared by two-way ANOVA with Tukey's multiple comparisons test. Part G shows individual tumor growth curves for each mouse.
Figure 8:
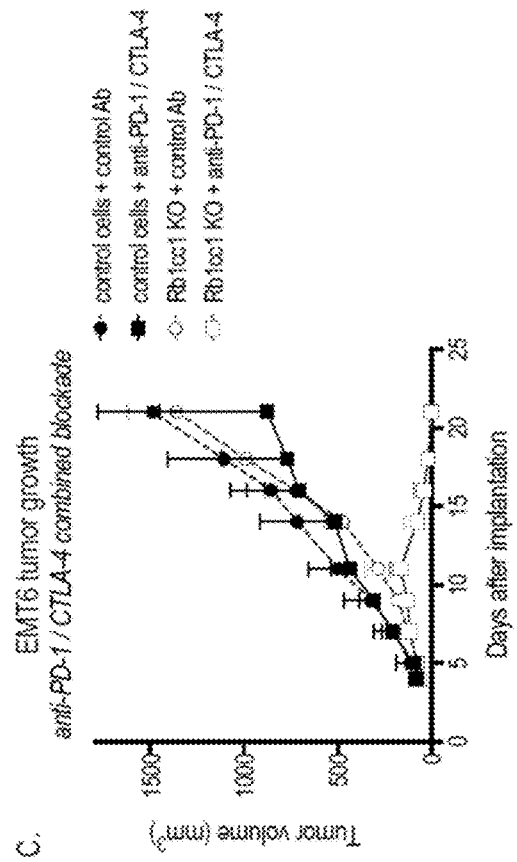
Figure 8:
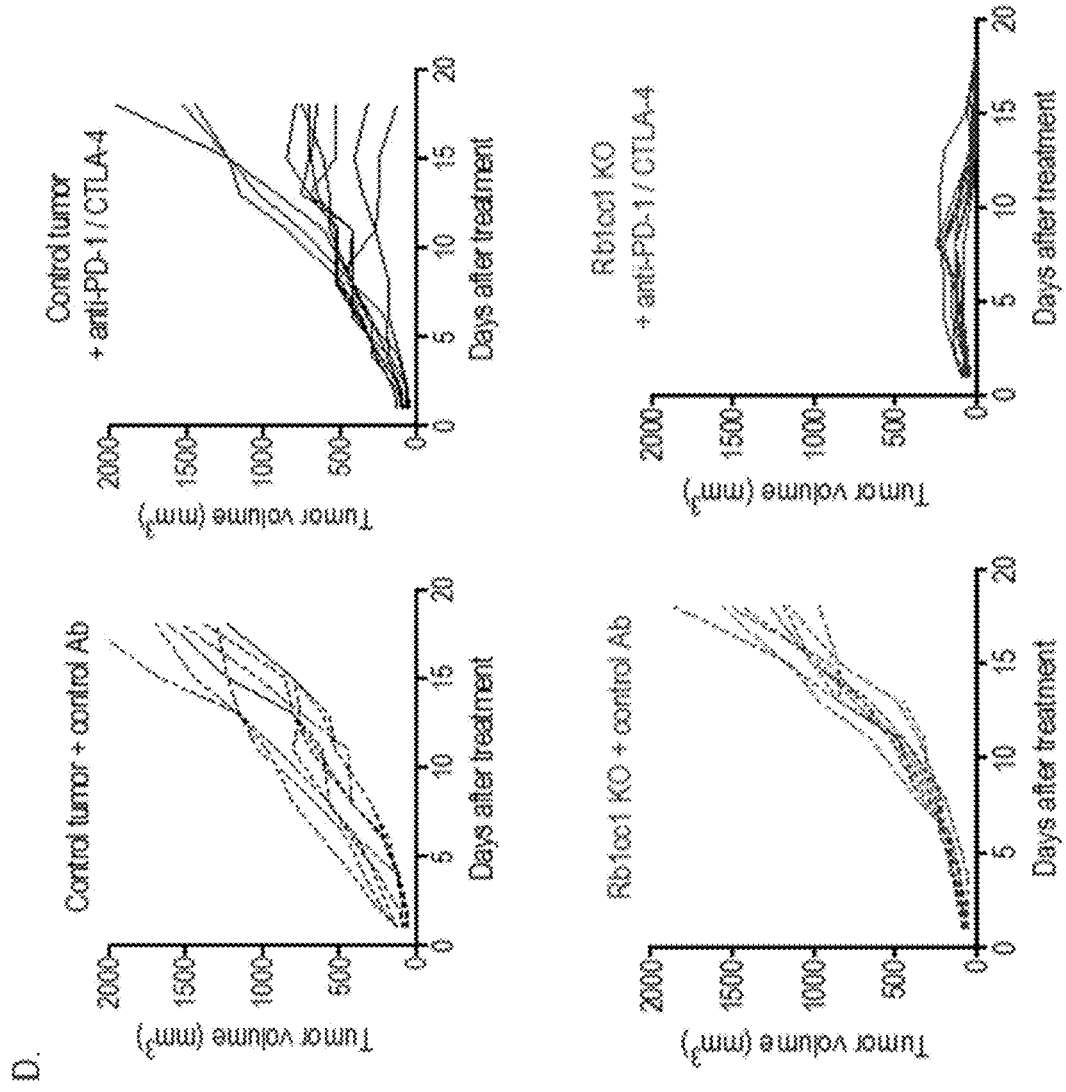
Figure 8:
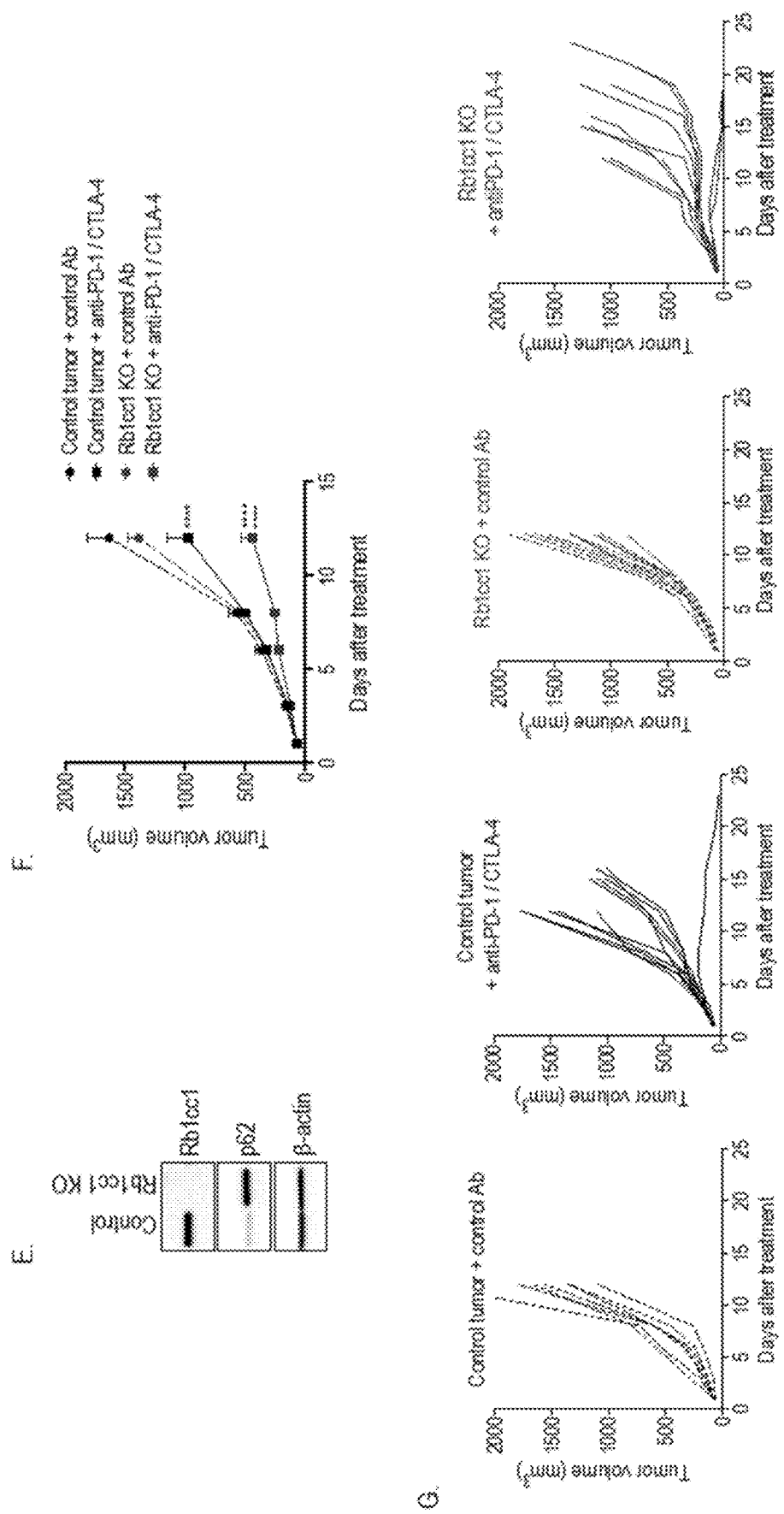

To further assess the clinical relevance of the findings, it was asked whether genetic inactivation of autophagy increases the responsiveness of tumors to T cell checkpoint inhibitors. KO of Rb1cc1 in EMT6 mouse breast cancer cells resulted in a substantial increase in p62 protein level, confirming a decrease in autophagic activity (FIG. 8, Part A), and increased the sensitivity of EMT6 cells to TNFα-induced apoptosis (FIG. 8, Part B). Control or Rb1cc1 KO cells were implanted into mice and at 3 days after implantation, mice were treated with control antibody or with a combination of PD-1 plus CTLA4 blocking antibodies. As shown in FIG. 8, Part C, combined blockade of PD-1 plus CTLA4 had only a modest growth inhibitory effect on control EMT6 tumors while promoting complete regression of Rb1cc1 KO tumors. Individual tumor growth curves show that 10/10 Rb1cc1 KO tumors completely regressed compared to 0/10 of the control tumors (FIG. 8, Part D).

A similar experiment with MC38 tumors was performed next. As shown in FIG. 8, Part E, KO of Rb1cc1 in MC38 cells resulted in impaired autophagy, as evidenced by a substantial increase in p62 protein level. While combined blockade of PD-1 plus CTLA4 reduced the growth of control MC38 tumors, the effect of checkpoint blockade on Rb1cc1 KO tumors was significantly greater (FIG. 8, Part F). The delated growth of Rb1cc1 KO tumors versus control tumors in response to immunotherapy is readily apparent from the individual tumor growth curves are shown in FIG. 8, Part G). Taken together, these findings show that tumors with impaired autophagy exhibit increased responsiveness to clinically-relevant T cell checkpoint inhibitors.

The effect of Tnfrsf1a (encodes TNFR1) KO in the context of Rb1cc1 KO tumors was tested. As disclosed herein, the increased TNFα-mediated apoptosis that is observed in Rb1cc1 KO cells was reversed in Rb1cc1/Tnfrsf1a double KO EMT6 cells (FIGS. 8, A and B). In vivo genetic inactivation of Tnfrsf1a limited the sensitization to immunotherapy that is observed in Rb1cc1 KO tumors (FIGS. 8, C and D). Thus, in the context of a tumor with impaired autophagy, Tnfrsf1a KO is protective. In control tumors with intact autophagy, Tnfrsf1a KO does not protect tumors from immune checkpoint blockade but actually sensitizes to treatment (FIG. 8C). It is apparent that Tnfrsf1a KO affects tumors in a context-dependent manner. Nevertheless, the data show that in the setting of impaired tumor cell autophagy, TNFα-induced apoptosis is an important component of antitumor immunity.

Figure 26:
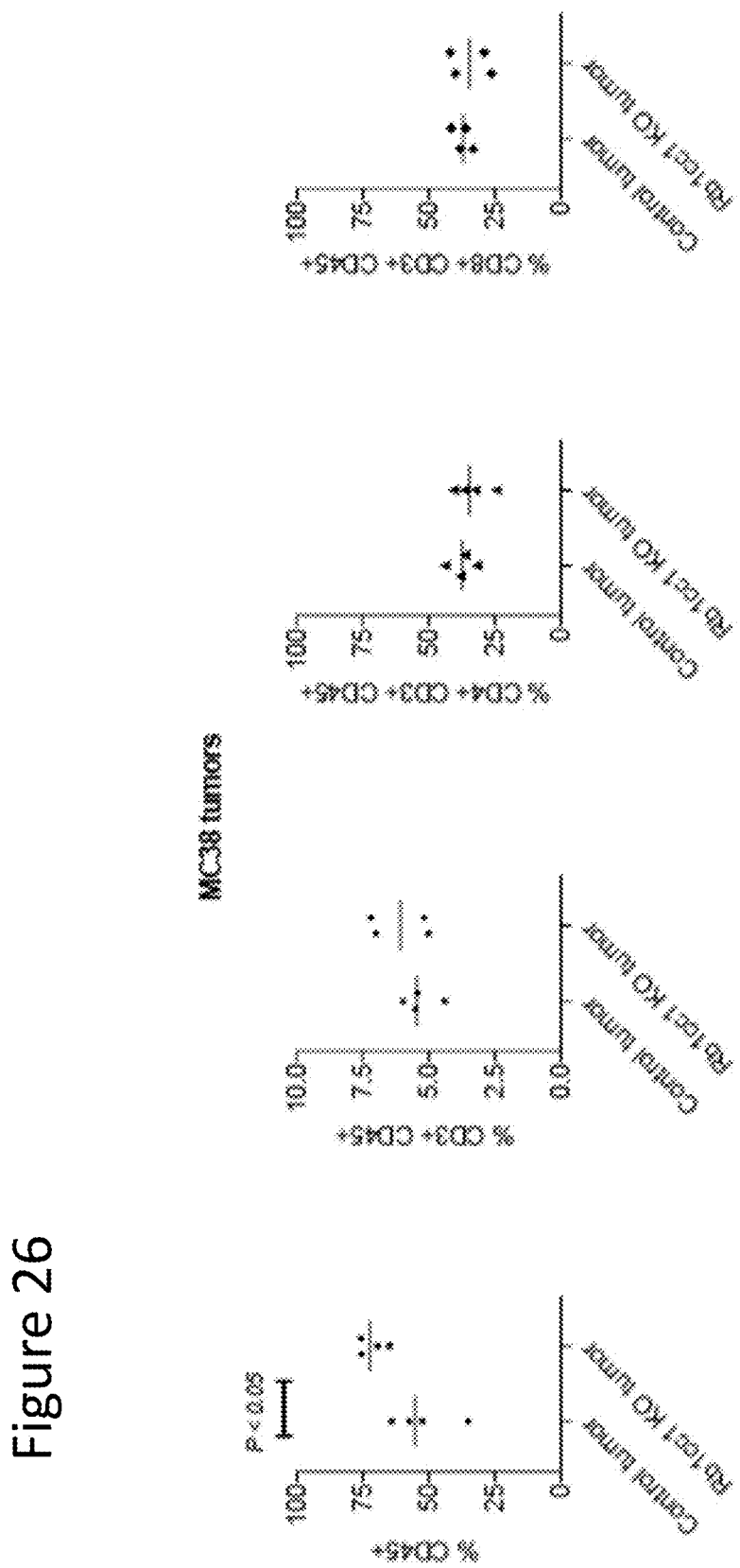
FIG. 26 shows that genetic inactivation of autophagy in tumors affects leukocyte infiltration. Depicted is flow cytometry analysis of CD45+, CD3+, CD4+ and CD8+ cells in MC38 and EMT6 parental or Rb1cc1 KO tumors. Graphs show individual tumors (n=4) with median values indicated. Groups were compared by one-way ANOVA with Tukey's multiple comparisons test.
Figure 26:
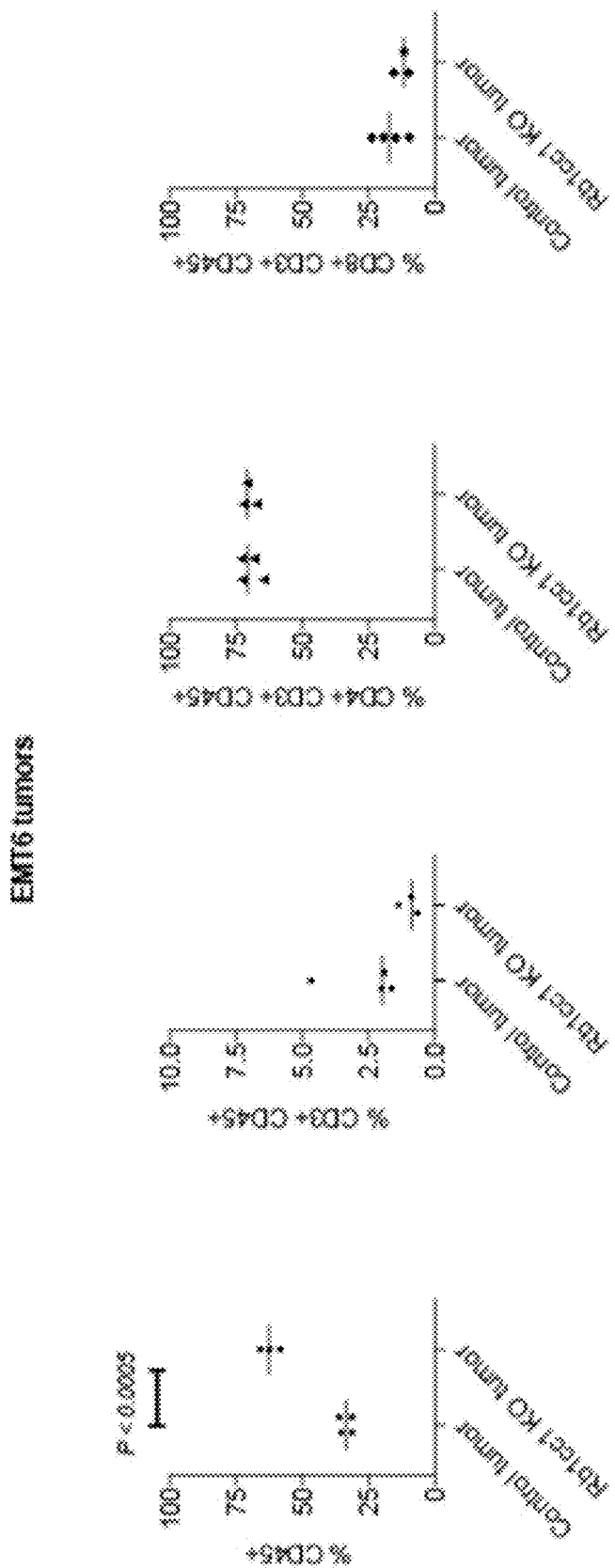

Leukocyte infiltration into Rb1cc1 KO tumors was assessed. In both the EMT6 and MC38 models, Rb1cc1 KO tumors had elevated numbers of CD45+ leukocytes, compared with control tumors (FIG. 26). However, although overall leukocyte infiltration was increased, a preferential infiltration of either CD4+ or CD8+ T cells was not observed. Nevertheless, it remains possible that both increased leukocyte infiltration and increased sensitivity to T cell-mediated killing contribute to the enhanced response to immunotherapy observed in the autophagy-impaired tumor models.

A genome-scale CRISPR screen was used to identify tumor cell TNFα signaling as an important component of T cell-mediated killing and, conversely, to identify protective roles for both the NF-κB and autophagy pathways. The data presented herein indicate that autophagy limits tumor cell killing by TNFα via inhibition of caspase-8 activation, upstream of mitochondrial involvement. More specifically, autophagy appears to inhibit the formation and/or activity of the FADD/caspase-8 complex, which is consistent with the observation that autophagy can limit tumor cell killing by TRAIL, which also induces cytotoxicity via FADD/caspase-8.

These in vivo studies show that genetic inactivation of autophagy in tumor cells enhances the efficacy of T cell checkpoint inhibitors, suggesting that pharmacologic inhibition of autophagy could also enhance the efficacy of such treatments. Although the role of autophagy in cancer has been widely studied, it remains unclear how important the process is to the growth/survival of tumor cells. Nevertheless, the data presented herein indicate that autophagy inhibitors, apart from potential modulation of tumor cell growth, could sensitize cancer cells to TNFα-induced apoptosis.

In summary, the analysis presented herein uncovered a role for autophagy in limiting tumor cell susceptibility to T cell-mediated killing. The identification of autophagy as a potential mechanism of tumor immune escape suggests the possibility that autophagy inhibitors could enhance the efficacy of T cell-engaging immunotherapies. Moreover, the data provided herein indicate that autophagy limits tumor cell killing by T cells and TNFα via inhibition of caspase-8 activation, upstream of mitochondrial involvement. Furthermore, inhibition of autophagy did not sensitize tumor cells to chemotherapy-induced apoptosis, suggesting a relatively specific role for autophagy in modulation of TNFα signaling rather than a more general anti-apoptotic function (e.g., mitophagy). Thus, the data provided herein suggest a novel therapeutic use of autophagy inhibitors, i.e., making cancer cells more susceptible to T cell killing, even if the cancer cells are not dependent on autophagy for growth/survival.

Materials and Methods

Cancer Cell Lines

MC38 mouse colon cancer cells were obtained from National Institutes of Health (NIH) repository. 4T1, B16F10, CT26, EMT6, and L929 mouse carcinoma cells and ZR75-1, HCT-116, HeLa, BT-20, Me-180, and MDA-MB-361 human carcinoma cells as well as human embryonic kidney (HEK) 293T human cells were from the American Type Culture Collection (ATCC). Colon26 mouse carcinoma cells were from the Division of Cancer Treatment and Diagnosis, National Cancer Institute (operated by Charles River Laboratories). All cells were cultured in the manufacturer's recommended media. All cell lines were authenticated by short tandem repeat profiling in 2016 (IDEXX BioResearch).

Mice

OT-1 C57BL/6-Tg(TcraTcrb)1100Mjb/J mice (003831), C57BL/6 mice (000664) and Balb/c mice (000651) were from Jackson Laboratory.

CRISPR Knockout sgRNA Library and Genome-Scale Screen

Mouse sgRNA libraries (GeCKO A and B; ~130,000 sgRNAs total) and pLentiCas9-Blast plasmid were purchased from GenScript. Genome-wide CRISPR/Cas9 screens were performed using MC38 cells engineered to express Cas9 nuclease by lentiviral infection (pLentiCas9-Blast) and selection with blasticidin (12 µg/ml). MC38-Cas9 cells were infected with the mouse GeCKO library (A and B combined) at a multiplicity of infection of 0.3 such that each sgRNA was introduced into ~200 cells. Cells were selected with 12 µg/ml puromycin for 3 days and approximately 130 million cells were set aside as a reference control sample. At 7 days post-infection, the T cell killing assay was set up in triplicate. Library engineered cells at ~2000× library representation were pulsed with Ova peptide and cells at ~200× library representation were pulsed with control peptide. After peptide pulsing, cells were co-cultured with activated CD8$^+$ T cells (isolated from OT-1 mice) at an E:T ratio of 1:3. After 24 hours of co-culture, when ~90% of the tumor cells had been killed, non-adherent cells were washed away with PBS and living tumor cells were harvested. Genomic DNA extraction was subsequently performed using the DNeasy Blood & Tissue Kit (Qiagen) and NGS libraries were prepared as described previously. The NGS libraries were subsequently multiplexed and run on the NextSeq 500 (Illumina) generating 80 base pair (bp) single-end reads. After demultiplexing with bcl2fastq software (Illumina), reads were screened for the 16 bp vector sequence adjacent to the sgRNA and the downstream 20 bp sgRNA reads were extracted for the sgRNA count. Subsequently, MAGeCK was used to count the reads and perform gene/sgRNA enrichment and statistical analysis. MC38 cells grown without addition of T cells were harvested one week post-infection to compare sgRNA representation to that in the reference control cells.

sgRNA sequences (gene name, sgRNA ID, sgRNA number when applicable and sequence) used for validation experiments were as follows (individual sgRNAs were cloned into either pLenti-Guide-Puro or pLentiCRISPR v2 plasmids):

```
Map3k7, MGLibA_30286, 1,
                                    (SEQ ID NO: 16)
GATGATCGAAGCGCCGTCGC;

Map3k7, MGLibA_30288, 3,
                                    (SEQ ID NO: 18)
GGGACTTACTGGATTCAGGC;

Map3k7, MGLibB_30278, 5,
                                    (SEQ ID NO: 20)
TTAACTCAGGTTGTCGGAAG;
```

-continued

```
Rbck1, MGLibA_44718, 1,
                                    (SEQ ID NO: 22)
AGTACGCCCGGATATGACAG;

Rbck1, MGLibA_44720, 3,
                                    (SEQ ID NO: 24)
CAGCTTACCGGTGGTGACTC;

Rbck1, MGLibB_44706, 5,
                                    (SEQ ID NO: 26)
CGGGCGTACTGTGAGCCAAA;

Rela, MGLibA_45073, 2,
                                    (SEQ ID NO: 29)
TCATCGAACAGCCGAAGCAA;

Rela, MGLibA_45074, 3,
                                    (SEQ ID NO: 30)
GCCCAGACCGCAGTATCCAT;

Rela, MGLibB_45061, 6,
                                    (SEQ ID NO: 33)
ACTTACCTGAGGGAAAGATG;

Rb1cc1, MGLibA_44690, 3,
                                    (SEQ ID NO: 36)
TCAAGATAGACCCAATGATG;

Rb1cc1, MGLibB_44675, 4,
                                    (SEQ ID NO: 37)
CTCCATTGACCACCAGAACC;

Rb1cc1, MGLibB_44676, 5,
                                    (SEQ ID NO: 38)
ATTTGAACAGTCCTCCAGAT;

Atg9a, MGLibA_05661, 1,
                                    (SEQ ID NO: 40)
CATAGTCCACACAGCTAACC;

Atg9a, MGLibA_05662, 2,
                                    (SEQ ID NO: 41)
TTGGGATCCGAAGAGCATGT;

Atg9a, MGLibB_05661, 4,
                                    (SEQ ID NO: 43)
TCTATAACATTTGCTGCTAT;

Atg12, MGLibA_05621, 3,
                                    (SEQ ID NO: 48)
GAGCGAACCCGGACCATCCA;

Atg12, MGLibB_05620, 5,
                                    (SEQ ID NO: 50)
CCTGCATTACTGCAAATCCC;

Atg12, MGLibB_05621, 6,
                                    (SEQ ID NO: 51)
TTCTGGCTCATCCCCATGCC;

Tnfrsf1a, MGLibA_55116,
                                    (SEQ ID NO: 52)
GTGTCTCACTCAGGTAGCGT;

Ripk1, MGLibA_45635, 3,
                                    (SEQ ID NO: 53)
GTACACGTCCGACTTCTCCG;

Fadd, MGLibA_16988, 2,
                                    (SEQ ID NO: 54)
TAGATCGTGTCGGCGCAGCG;

B2M, MGLibA_06111, 1,
                                    (SEQ ID NO: 55)
AGTATACTCACGCCACCCAC;

Rb1cc1, HGLibB_40366, 6,
                                    (SEQ ID NO: 56)
GGCTGCAATCATGGCCAACC;
```

-continued

Mlst8, MGLibA_31480, 1,
GACTCCGTCATAACTGATGA;
(SEQ ID NO: 57)

Mlst8, MGLibA_31482, 3,
CGAAGCATGATTGCTGCTGC;
(SEQ ID NO: 58)

Mlst8, MGLibB_31471, 4,
AGCACTCACGGCACTATTGA.
(SEQ ID NO: 59)

Lentiviral Packaging/Transduction and CRISPR-Mediated Gene Knockout

For validation experiments, sgRNAs targeting genes of interest were cloned into pLenti-Guide-Puro or pLentiCrispr v2 (GenScript). HEK293T cells were transfected with pLenti-Cas9-Blast or pLenti-Guide-Puro or pLentiCrispr v2 and the packaging plasmids psPAX and pMD2.G using Lipofectamine 2000. After 6 hours, medium was replaced with complete growth medium. After 72 hours, lentivirus-containing supernatant was harvested, filtered, concentrated by ultracentrifugation and stored at −80° C. For lentiviral transduction, tumor cells were seeded in complete medium with 5 ug/ml polybrene and lentivirus at MOI of 0.3. Mouse GeCKO A and B plasmid libraries were pooled and packaged into lentivirus in the same way, using a sufficient number of HEK293T cells to maintain library representation. After 24 hours, medium was replaced with complete growth medium containing DNase and lentivirus was concentrated as above.

Isolation and Activation of CD8+ T Cells

CD8$^+$ T cells were isolated from spleens and lymph nodes of 6-8 week old male OT-1 mice. These mice contain transgenic inserts for mouse Tcra-V2 and Tcrb-V5 genes. The transgenic T cell receptor was designed to recognize ovalbumin peptide residues 257-264 in the context of H-2Kb MHC class I protein. In some experiments, human CD8+ T cells were isolated from PBMCs. T cells were activated in vitro with CD3/CD28 beads at a 1:2 bead:cell ratio for 2-3 days. T cells were activated in RPMI-1640 medium containing 20 ng/ml mouse IL-2, 10% heat inactivated fetal bovine serum, 20 mM HEPES, 2 mM L-glutamine, 1 mM sodium pyruvate, 0.05 mM 2-mercaptoethanol and 50 U/ml penicillin/streptomycin. For human tumor cell killing experiments using CD3 bispecific antibody, human T cells were isolated from peripheral blood mononuclear cells (PBMCs) (ReachBio) using Dynabeads Untouched Human T Cells Kit (Thermo Fisher Scientific).

In Vitro Cytotoxicity Assays

MC38 cells were seeded at 34,000 cells per 24 well and pulsed with 1 ng/ml Ova or scrambled peptide 24 hours after seeding. Pulsed cells were cultured with activated CD8$^+$ T cells (isolated from OT-1 mice) at the indicated E:T ratios. After 24 hours, non-adherent tumor cells were washed away with PBS and cell viability was assessed. Where indicated, a neutralizing TNFα antibody or isotype control antibody were added at concentrations of 10 or 20 µg/ml.

Human ZR-75-1 cells were seeded at 100,000 cells per 24 well. After 24 hours, cells were incubated with activated CD8$^+$ T cells (isolated from human PBMCs) at the indicated E:T ratios for 24 hours in the presence of 12 ng/ml breast tumor antigen×CD3 or control (doesn't bind to ZR-75-1 cells) bispecific antibodies in the absence or presence of 5 µM autophagy inhibitor SAR-405.

The effects of TNFα, TRAIL, doxorubicin or paclitaxel on cell viability were assessed following 24 hour incubations at the indicated concentrations. The effects of 5 µM autophinib or SAR-405 on TNFα (10 ng/ml) or TRAIL (10 ng/ml or 50 ng/ml) induced killing were assessed following 24 hour incubations unless otherwise indicated. In all cases, cell viability was measured using CCK8 cell counting kit-8 (CCK-8) reagent, which is reduced by dehydrogenase activities in cells to give a yellow-colored formazan dye (Dojindo). The absorbance was measured using a SpectraMax M3 microplate reader (Molecular Devices).

Tumor Xenograft Studies

For EMT6 xenograft experiments, $5 \times 10^6$ cells were injected subcutaneously into the right flank of 6- to 8-week-old female BALB/c mice. Three days after implantation, mice were treated with either CTLA-4 plus PD-1 blocking antibodies or isotype control (n=10 mice per group). On the first day of treatment, CTLA-4 plus PD-1 blocking antibodies (5 mg/kg) were administered by intraperitoneal injection. On days 3 and 6 of treatment, CTLA-4 antibody (2.5 mg/kg) was administered. On days 4, 8, 11, and 15, PD-1 antibody at 5 mg/kg was administered. Tumor growth was monitored three times per week with calipers, and tumor volumes (mm3) were estimated using the following formula: ½× length×width.

For MC38 xenograft experiments, $3 \times 10^5$ cells were injected subcutaneously into the right flank of 6- to 8-week-old female C57BL/6 mice. Ten days after implantation, when tumor volumes were ~70 mm3, mice were randomized and treated with either CTLA-4 plus PD-1 blocking antibodies or isotype control as described above (n=7 to 12 mice per group). For tumor experiments using CRISPR-engineered cells, Cas9 protein and sgRNA were delivered to cells via transient transfection of ribonucleoproteins to overcome the increased immunogenicity associated with lentiviral modification. The sgRNA sequences were as follows: for Rb1cc1 KO, CUCCAUUGACCACCAGAACC; for Tnfrsf1a KO, UUCUCCCGGUCACCAAG; and nontargeting, AAAUGUGAGAUCAGAGUAAU. After transfection, clones were isolated and tested for gene KO. For MC38 cells, a pool of eight KO clones was used for tumor studies, and for EMT6 cells, a pool of four KO clones was used.

Antibodies and Reagents

PD-1 blocking antibody (clone RMP1-14) and rat IgG2a isotype control antibody were from BioXCell. An in-house version of the CTLA4 blocking antibody (clone 9D9), with isotype IgG2a, was generated using the published primary sequence. CD3 bispecific antibodies were generated at Regeneron using methods described previously (Murphy et al., 2014; Smith et al., 2015). Mouse-reactive TNFα neutralizing antibody (clone MP6-XT22) and rat IgG1 isotype control antibody were from Biolegend. Human-reactive TNFα neutralizing antibody (clone MAB1) and mouse IgG1 isotype control antibody were from Biolegend. Recombinant mouse and human TNFα and IFNγ were from PeproTech. Recombinant human TRAIL was from Enzo. Z-VAD-FMK pan-caspase inhibitor was from InvivoGen. Ova SIINFEKL (257-264) peptide and scrambled control peptide FILKSINE (257-264) were from AnaSpec. EasySep mouse CD8$^+$ T cell isolation kit was from Stemcell. Dynabeads mouse T-activator CD3/CD28 beads were from ThermoFisher. Dynabeads untouched human CD8 T Cells Kit was from ThermoFisher. Human PBMCs were purchased from ReachBio. Mouse cytokine array panel A was from R&D systems. Protease/phosphatase inhibitor and BCA reagent were from ThermoFisher. Autophinib was from Biovision, SAR-405 was from MedChemExpress and LCL-161 (Smac mimetic) was from Selleckchem. Nec-1s was from BioVision. Cas9 protein and trueguide synthetic gRNAs were from ThermoFisher. Doxorubicin and paclitaxel were from Selleckchem.

Immunoblotting

Whole cell lysates were prepared in tris-glycine SDS sample buffer (ThermoFisher) containing 5% 2-mercaptoethanol. Western blotting was performed by conventional techniques using tris-glycine polyacrylamide SDS gels (ThermoFisher) and PVDF membranes (BioRad). Blots were blocked in 5% milk powder and 0.5% Tween-20 in TBS and then incubated overnight with primary antibodies. After addition of secondary antibodies, membranes were incubated with SuperSignal West Pico Plus or Femto substrate (ThermoFisher) and luminescence was captured with a C300 imager (Azure Biosystems). Primary antibodies against TAK1, Rbck1, RelA p65, Rb1cc1, Atg12, cleaved caspase-8, procaspase-8, RIPK1, RIPK1 phospo-Ser321, RIPK1 phospho-Ser166, Iκ-Bα, A20, p62, phospho-p65, LC3B, TNFR1 (CST), Atg9a (Novus), cIAP1 (Enzo), β2M (ThermoFisher), FADD and ICAM (Abcam) were used. Horseradish peroxidase-conjugated β-Actin antibody and secondary antibodies against mouse IgG, rabbit IgG and goat IgG were from Santa Cruz Biotechnology.

Tumor xenograft studies. To overcome the increased immunogenicity associated with modifying cells with lentiviral vectors, Cas9 protein and sgRNA was delivered to cells via transient transfection of ribonucleoproteins. sgRNA sequence used for Rb1cc1 KO was CUCCAUUGAC-CACCAGAACC and non-targeting sgRNA sequence was AAAUGUGAGAUCAGAGUAAU. Following transfection, clones were isolated and tested for gene knockout. For MC38 cells, a pool of 8 KO clones was used for tumor studies and for EMT6 cells a pool of 4 KO clones was used.

Mouse Cytokine Array

Control or Rb1cc1 KO MC38 cells expressing Rb1cc1-targeting sgRNA were treated with 10 ng/ml mouse TNFα for 4 hours. After treatment, cells were washed twice with ice-cold PBS and lysed with 1 mL of 1% IGEPAL CA-630, 20 mM Tris-HCL pH 8.0, 137 mM NaCL, 10% Glycerol, 2 mM EDTA plus 1× Halt protease/phosphatase inhibitor cocktail. After 30 minutes of rotation at 4° C., the lysate was cleared by centrifugation at 14,000 g at 4° C. for 5 minutes and protein concentration was determined by standard BCA assay. To assess cytokine production, the proteome profiler mouse cytokine array panel A (R&D Systems) was used. The standard kit protocol was followed using 300 µg of cell lysate.

Tumor Immune Phenotyping and Flow Cytometry Analysis

Tumors were harvested, mechanically digested into fragments (>4 mm), and then enzymatically digested using a mouse tumor dissociation kit (Miltenyi Biotec) for 45 min at 37° C. Single-cell suspensions were prepared, and red blood cells were lysed with ACK buffer (Lonza). The cells were counted, blocked for 30 min on ice with Fc block (BioLegend), and stained with a viability dye and CD45, CD3, CD4, and CD8 antibodies (BioLegend) as indicated. MC38 parental and autophagy KO cells were stained with MHC-I (H2-kb) or isotype control (Invitrogen) antibodies or with MHC-I (H2-kb)-Ova (SIINFEKL) or isotype control (BioLegend) antibodies.

Quantification and Statistical Analysis

For analysis of the pooled CRISPR screen, the data were normalized by multiplying a scaling factor to each sample such that all the samples had the same total read counts. To compare groups, the normalized read count tables were used as inputs to MAGeCK (version 0.5.8), with one group assigned as the treatment and the other as the control (58). To compare data from cell-based assays with multiple treatment groups, one-way ANOVA with Tukey's multiple comparisons test was used. To compare the growth of tumors subjected to different treatments, two-way ANOVA with Tukey's multiple comparisons test was used. P value less than 0.05 was considered significant. Statistical comparisons were performed using GraphPad Prism.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of sensitizing a cancer cell to T cell-mediated killing, the method comprising contacting the cancer cell, in the presence of a T cell, with an agent that inhibits autophagy in the cancer cell, wherein the agent inhibits the expression or activity of the autophagy gene RB1CC1.

2. The method of claim 1, wherein the agent modifies the autophagy gene, wherein modifying the autophagy gene results in a decrease in the expression or activity of the autophagy gene.

3. The method of claim 1, wherein the agent is a composition comprising a guide RNA or a nucleic acid that encodes a guide RNA, and wherein the guide RNA comprises a DNA-targeting segment that targets a guide RNA target sequence within the autophagy gene and is effective to direct a Cas enzyme to cleave or bind a sequence in the autophagy gene.

4. The method of claim 3, wherein the guide RNA target sequence includes or is within about 100 nucleotides of the start codon of the autophagy gene.

5. The method of claim 3, wherein the composition further comprises a Cas protein or a nucleic acid sequence encoding the Cas protein.

6. The method of claim 5, wherein the Cas protein is a nuclease-active Cas protein or a nuclease-inactive Cas protein fused to a transcriptional repressor domain.

7. The method of claim 6, wherein the Cas protein is a Cas9 protein.

8. The method of claim 5, wherein the agent is a composition comprising a nucleic acid that comprises a first nucleotide sequence that encodes a guide RNA and a second nucleotide sequence that encodes a Cas protein.

9. The method of claim 1, wherein the agent is a TALEN nuclease, a Zinc-finger nuclease, or an interfering nucleic acid.

10. The method of claim 9, wherein the agent is an interfering nucleic acid selected from an siRNA, an shRNA, a miRNA, or an antisense oligonucleotide.

11. The method of claim 1, wherein the cancer cell is a lung cancer cell, a breast cancer cell, a colon cancer cell, a cervical cancer cell, a pancreatic cancer cell, a renal cancer cell, a stomach cancer cell, a GI cancer cell, a liver cancer cell, a bone cancer cell, a hematological cancer cell, a neural tissue cancer cell, a melanoma cell, a thyroid cancer cell, a ovarian cancer cell, a testicular cancer cell, a prostate cancer cell, a cervical cancer cell, a vaginal cancer cell, or a bladder cancer cell.

12. A method of sensitizing a cancer cell in a subject to T cell-mediated killing or increasing T cell-mediated killing of a cancer cell in a subject, the method comprising administering to the subject an agent that inhibits autophagy in the cancer cell, wherein the agent inhibits the expression or activity of the autophagy gene RB1CC1.

13. The method of claim 12, wherein the agent modifies the autophagy gene, wherein modifying the autophagy gene results in a decrease in the expression or activity of the autophagy gene.

14. The method of claim 12, wherein the agent is a composition comprising a guide RNA (gRNA) or a nucleic acid that encodes a guide RNA, and wherein the guide RNA comprises a DNA-targeting segment that targets a guide RNA target sequence within the autophagy gene and is effective to direct a Cas enzyme to cleave or bind a sequence in the autophagy gene.

15. The method of claim 14, wherein the guide RNA target sequence includes or is within about 100 nucleotides of the start codon of the autophagy gene.

16. The method of claim 14, wherein the composition further comprises a Cas protein or a nucleic acid sequence encoding the Cas protein.

17. The method of claim 16, wherein the Cas protein is a nuclease-active Cas protein or a nuclease-inactive Cas protein fused to a transcriptional repressor domain.

18. The method of claim 16, wherein the Cas protein is a Cas9 protein.

19. The method of claim 16, wherein the agent is a composition comprising a nucleic acid that comprises a first nucleotide sequence that encodes a guide RNA and a second nucleotide sequence that encodes a Cas protein.

20. The method of claim 12, wherein the agent is a TALEN nuclease, a Zinc-finger nuclease, or an interfering nucleic acid.

21. The method of claim 20, wherein the agent is an interfering nucleic acid selected from an siRNA, an shRNA, a miRNA, or an antisense oligonucleotide.

22. The method of claim 12, wherein the cancer cell is a lung cancer cell, a breast cancer cell, a colon cancer cell, a cervical cancer cell, a pancreatic cancer cell, a renal cancer cell, a stomach cancer cell, a GI cancer cell, a liver cancer cell, a bone cancer cell, a hematological cancer cell, a neural tissue cancer cell, a melanoma cell, a thyroid cancer cell, a ovarian cancer cell, a testicular cancer cell, a prostate cancer cell, a cervical cancer cell, a vaginal cancer cell, or a bladder cancer cell.

23. The method of claim 12, wherein the subject has a tumor, and the at least one agent is administered locally to the tumor or tumor microenvironment.

24. The method of claim 12, wherein the method further comprises administering an additional anti-cancer therapy to the subject.

25. The method of claim 24, wherein the additional anti-cancer therapy is a cancer immunotherapy.

26. The method of claim 25, wherein the cancer immunotherapy comprises autologous or allogenic T cell therapy, autologous or allogenic CAR T cell therapy, or administering TNF-α, an immune checkpoint inhibitor, or a cancer vaccine to the subject.

27. A method of treating cancer in a subject, the method comprising administering to the subject an agent that inhibits autophagy in a cancer cell in the subject and a cancer immunotherapy that induces T cell-mediated killing of cancer cells, wherein the agent inhibits the expression or activity of the autophagy gene RB1CC1.

28. The method of claim 27, wherein the cancer immunotherapy comprises autologous or allogenic T cell therapy, autologous or allogenic CAR T cell therapy, or administering TNF-α, an immune checkpoint inhibitor, or a cancer vaccine to the subject.

29. The method of claim 28, wherein the agent modifies the autophagy gene, wherein modifying the autophagy gene results in a decrease in the expression or activity of the autophagy gene.

30. The method of claim 28, wherein the agent is a composition comprising a guide RNA or a nucleic acid that encodes a guide RNA, and wherein the guide RNA comprises a DNA-targeting segment that targets a guide RNA target sequence within the autophagy gene and is effective to direct a Cas enzyme to cleave or bind a sequence in the autophagy gene.

31. The method of claim 30, wherein the composition further comprises a Cas protein or a nucleic acid sequence encoding the Cas protein.

32. The method of claim 31, wherein the Cas protein is a nuclease-active Cas protein or a nuclease-inactive Cas protein fused to a transcriptional repressor domain.

33. The method of claim 31, wherein the Cas protein is a Cas9 protein.

34. The method of claim 31, wherein the agent is a composition comprising a nucleic acid that comprises a first nucleotide sequence that encodes a guide RNA and a second nucleotide sequence that encodes a Cas protein.

35. The method of claim 27, wherein the agent is a TALEN, a Zinc-finger nuclease, or an interfering nucleic acid.

36. The method of claim 35, wherein the agent is an interfering nucleic acid selected from an siRNA, an shRNA, a miRNA, or an antisense oligonucleotide.

37. The method of claim 27, wherein the cancer cell is a lung cancer cell, a breast cancer cell, a colon cancer cell, a cervical cancer cell, a pancreatic cancer cell, a renal cancer cell, a stomach cancer cell, a GI cancer cell, a liver cancer cell, a bone cancer cell, a hematological cancer cell, a neural tissue cancer cell, a melanoma cell, a thyroid cancer cell, a ovarian cancer cell, a testicular cancer cell, a prostate cancer cell, a cervical cancer cell, a vaginal cancer cell, or a bladder cancer cell.

38. A combination therapy comprising an agent that inhibits autophagy in a cancer cell and a cancer immunotherapy that induces T cell-mediated killing of cancer cells for use in treating cancer, wherein the agent inhibits the expression or activity of the autophagy gene RB1CC1.

39. The method of claim 25, wherein the cancer immunotherapy comprises a T cell therapy.

40. The method of claim 27, wherein the cancer immunotherapy comprises a T cell therapy.

41. The combination therapy of claim 38, wherein the cancer immunotherapy comprises a T cell therapy.

42. The method of claim 1, wherein the method does not comprise administration of isolated tumor necrosis factor-alpha (TNF-α).

43. The method of claim 12, wherein the method does not comprise administration of isolated tumor necrosis factor-alpha (TNF-α).

44. The method of claim 27, wherein the method does not comprise administration of isolated tumor necrosis factor-alpha (TNF-α).

45. The combination therapy of claim 38, wherein the therapy does not comprise isolated tumor necrosis factor-alpha (TNF-α).

* * * * *

UNITED STATES PATENT AND TRADEMARK OFFICE
CERTIFICATE OF CORRECTION

| | | |
|---|---|---|
| PATENT NO. | : 11,965,161 B2 | |
| APPLICATION NO. | : 17/191466 | |
| DATED | : April 23, 2024 | |
| INVENTOR(S) | : Young et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
Sixth Day of January, 2026

John A. Squires
*Director of the United States Patent and Trademark Office*

SEQUENCE LISTING

```
<160> NUMBER OF SEQ ID NOS: 57

<210> SEQ ID NO 1
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
guuuuagagc uaugcu                                                      16

<210> SEQ ID NO 2
```

-continued

<400> SEQUENCE: 2

000

<210> SEQ ID NO 3
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
agcauagcaa guuaaaauaa ggcuaguccg uuaucaacuu gaaaaagugg caccgagucg    60
gugcuuu                                                              67

<210> SEQ ID NO 4
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aaacagcaua gcaaguuaaa auaaggcuag uccguuauca acuugaaaaa guggcaccga    60
gucggugcuu uu                                                        72

<210> SEQ ID NO 5
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
guuggaacca uucaaaacag cauagcaagu uaaauaagg cuaguccguu aucaacuuga     60
aaaaguggca ccgagucggu gc                                             82

<210> SEQ ID NO 6
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guuuuagagc uagaaauagc aaguuaaaau aaggcuaguc cguuaucaac uugaaaaagu    60
ggcaccgagu cggugcu                                                   77

<210> SEQ ID NO 7
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
guuggaacca uucaaaacag cauagcaagu uaaaauaagg cuaguccguu aucaacuuga    60
aaaaguggca ccgagucggu gc                                             82

<210> SEQ ID NO 8
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
guuuuagagc uagaaauagc aaguuaaaau aaggcuaguc cguuaucaac uugaaaaagu    60
ggcaccgagu cggugc                                                  76

<210> SEQ ID NO 9
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
guuuaagagc uaugcuggaa acagcauagc aaguuuaaau aaggcuaguc cguuaucaac    60
uugaaaaagu ggcaccgagu cggugc                                       86

<210> SEQ ID NO 10
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
guuuuagagc uagaaauagc aaguuaaaau aaggcuaguc cguuaucaac uugaaaaagu    60
ggcaccgagu cggugcuuuu uuu                                          83

<210> SEQ ID NO 11
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
guuuuagagc uagaaauagc aaguuaaaau aaggcuaguc cguuaucaac uugaaaaagu    60
ggcaccgagu cggugcuuuu                                              80

<210> SEQ ID NO 12
<211> LENGTH: 92
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
guuuaagagc uaugcuggaa acagcauagc aaguuuaaau aaggcuaguc cguuaucaac    60
uugaaaaagu ggcaccgagu cggugcuuuu uu                                92

<210> SEQ ID NO 13
<211> LENGTH: 23

```
<212> TYPE: DNA
<213> ORGANISM: Unknown
<220> FEATURE:
<223> OTHER INFORMATION: Description of Unknown:
      Guide RNA target sequence
<220> FEATURE:
<221> NAME/KEY: modified_base
<222> LOCATION: (2)..(21)
<223> OTHER INFORMATION: a, c, t, g, unknown or other

<400> SEQUENCE: 13
gnnnnnnnnn nnnnnnnnnn ngg                                             23

<210> SEQ ID NO 14
<211> LENGTH: 23
<212> TYPE: DNA
<213> ORGANISM: Unknown
<220> FEATURE:
<223> OTHER INFORMATION: Description of Unknown:
      Guide RNA target sequence
<220> FEATURE:
<221> NAME/KEY: modified_base
<222> LOCATION: (1)..(21)
<223> OTHER INFORMATION: a, c, t, g, unknown or other

<400> SEQUENCE: 14
nnnnnnnnnn nnnnnnnnnn ngg                                             23

<210> SEQ ID NO 15
<211> LENGTH: 25
<212> TYPE: DNA
<213> ORGANISM: Unknown
<220> FEATURE:
<223> OTHER INFORMATION: Description of Unknown:
      Guide RNA target sequence
<220> FEATURE:
<221> NAME/KEY: modified_base
<222> LOCATION: (3)..(23)
<223> OTHER INFORMATION: a, c, t, g, unknown or other

<400> SEQUENCE: 15
ggnnnnnnnn nnnnnnnnnn nnngg                                           25

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatgatcgaa gcgccgtcgc                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cggcgcttcg atcatctcac                                                 20

<210> SEQ ID NO 18
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 18
gggacttact ggattcaggc                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gagtagtttg caaagctaag                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttaactcagg ttgtcggaag                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaggggggct cattgtataa                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agtacgcccg gatatgacag                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acgtgttgcg ggctgacagc                                                  20

<210> SEQ ID NO 24
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 24
cagcttaccg gtggtgactc                                                  20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aacctgtcct tccgaagccc                                                  20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cgggcgtact gtgagccaaa                                                  20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctgctatcaa gtatgccacc                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgattccgc tataaatgcg                                                  20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tcatcgaaca gccgaagcaa                                                  20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 30
gcccagaccg cagtatccat                                           20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctgccgggat ggctactatg                                           20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
accgtgaaag gggttattgt                                           20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acttacctga gggaaagatg                                           20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
agagtgtgta cttacagcgc                                           20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ctgaacgtgg caaagaactt                                           20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcaagataga cccaatgatg                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctccattgac caccagaacc                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atttgaacag tcctccagat                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctttaggaat agcaggtgca                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
catagtccac acagctaacc                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttgggatccg aagagcatgt                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 42
ctgcccaagt ctgtagtgcc                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tctataacat ttgctgctat                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tacatgtgaa gccattcttc                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aggatattcg agagaagaag                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgcagtttcg cccggaacgg                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctctggaagg ctctcgccgc                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
```
gagcgaaccc ggaccatcca                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcatcatacc aactgttccg                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cctgcattac tgcaaatccc                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttctggctca tccccatgcc                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gtgtctcact caggtagcgt                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtacacgtcc gacttctccg                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

```
tagatcgtgt cggcgcagcg                                               20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agtatactca cgccacccac                                               20

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ile Ile Asn Phe Glu Lys Leu
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Ile Leu Lys Ser Ile Asn Glu
1               5
```